US011440879B2

(12) United States Patent
Kruegel

(10) Patent No.: US 11,440,879 B2
(45) Date of Patent: *Sep. 13, 2022

(54) METHODS OF TREATING MOOD DISORDERS

(71) Applicant: Gilgamesh Pharmaceuticals, Inc., New York, NY (US)

(72) Inventor: Andrew Carry Kruegel, Secaucus, NJ (US)

(73) Assignee: Gilgamesh Pharmaceuticals, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/510,080

(22) Filed: Oct. 25, 2021

(65) Prior Publication Data

US 2022/0041551 A1 Feb. 10, 2022

Related U.S. Application Data

(63) Continuation of application No. 17/404,923, filed on Aug. 17, 2021, which is a continuation-in-part of application No. PCT/US2021/018534, filed on Feb. 18, 2021.

(60) Provisional application No. 62/978,075, filed on Feb. 18, 2020.

(51) Int. Cl.
*C07D 209/16* (2006.01)
*A61P 25/24* (2006.01)

(52) U.S. Cl.
CPC ............ *C07D 209/16* (2013.01); *A61P 25/24* (2018.01)

(58) Field of Classification Search
CPC .................................................. C07D 209/16
See application file for complete search history.

(56) References Cited

U.S. PATENT DOCUMENTS

| 8,288,406 B2 | 10/2012 | Frormann et al. |
| 2012/0095217 A1 | 4/2012 | Ritter et al. |
| 2012/0122948 A1 | 5/2012 | Soubhye et al. |
| 2018/0021326 A1 | 1/2018 | Stamets |
| 2018/0221396 A1 | 8/2018 | Chadeayne |

FOREIGN PATENT DOCUMENTS

| CA | 1100516 A | 5/1981 |
| CA | 1105938 A | 7/1981 |
| CN | 104276993 A | 1/2015 |
| CN | 110343050 A | 10/2019 |
| CN | 112174851 A | 1/2021 |
| CN | 113234036 A | 8/2021 |
| DE | 1668550 A1 | 7/1971 |
| DE | 2723937 A1 | 12/1977 |
| EP | 1956016 A1 | 8/2008 |
| GB | 853775 A | 11/1960 |
| KR | 20190120859 A | 10/2019 |
| WO | WO-2004000205 A2 | 12/2003 |
| WO | WO-2004000845 A1 | 12/2003 |
| WO | WO-2004000849 A2 | 12/2003 |
| WO | WO-2004043949 A1 | 5/2004 |
| WO | WO-2004043967 A1 | 5/2004 |
| WO | WO-2005063769 A1 | 7/2005 |
| WO | WO-2007017289 A2 | 2/2007 |
| WO | WO-2008071455 A1 | 6/2008 |
| WO | WO-2010081036 A2 | 7/2010 |
| WO | WO-2010136546 A1 | 12/2010 |
| WO | WO-2012013343 A1 | 2/2012 |
| WO | WO-2018064465 A1 | 4/2018 |
| WO | WO-2019077332 A1 | 4/2019 |
| WO | WO-2019081764 A1 | 5/2019 |
| WO | WO-2019129815 A1 | 7/2019 |
| WO | WO-2019160057 A1 | 8/2019 |
| WO | WO-2019/192602 A1 | 10/2019 |
| WO | WO-2019220139 A1 | 11/2019 |
| WO | WO-2020120539 A1 | 6/2020 |
| WO | WO-2020181194 A1 | 9/2020 |
| WO | WO-2021134086 A1 | 7/2021 |

OTHER PUBLICATIONS

Soubhye Jalal et al., "Conclusions", Pharmaceutical and Clinical Research, vol. 66(8) 1122-1132 (2014).
Brandt Simon D. et al., "Analytical chemistry of synthetic routes to psychoactive tryptamines : Part II. Characterisation of the Speeter and Anthony synthetic route to N,N-dialkylated tryptamines using GC-EI-ITMS, ESI-TQ-MS-MS and NMR", Analyst, vol. 130(3) 330 (2005).
Adamowicz Piotr et al., "Simple and rapid screening procedure for 143 new psychoactive substances by liquid chromatography-tandem mass spectrometry : Simple and rapid screening procedure for 143 new psychoactive substances", Drug Testing and Analysis, vol. 8 (7) 652-667 (2016).
Valentin Magne et al., "Synthesis of Spiroindolenines via Regioselective Gold(I)-Catalyzed Cyclizations of N-Propargyl Tryptamines", Advanced Synthesis and Catalysis, vol. 359 (22) 4036-4042 (2017).
Abolghasem Moghimi et al., "Synthesis of 2-(2-Fluorophenyl)-2-methylamino-Cyclohexanone as a New Ketamine Derivative", Synthetic Communications, vol. 44(14) 2021-2028 (2014).
Cozzi, Nicholas V, and Paul F Daley. "Receptor binding profiles and quantitative structure-affinity relationships of some 5-substituted-N,N-diallyltryptamines." *Bioorganic & medicinal chemistry letters* vol. 26,3 (2016): 959-964.
Davidsen et al. "Ketamine analogues: Comparative toxicokinetic in vitro-in vivo extrapolation and quantification of 2-fluorodeschloroketamine in forensic blood and hair samples", J. Pharm Biomed Anal. 180:113049 (2020).
Dinger, Julia et al. "Cytochrome P450 inhibition potential of new psychoactive substances of the tryptamine class." Toxicology Letters vol. 241 (2016): 82-94.

(Continued)

*Primary Examiner* — Shawquia Jackson
(74) *Attorney, Agent, or Firm* — Scully, Scott, Murphy & Presser, P.C.

(57) ABSTRACT

Methods of treating mood disorders with compounds disclosed herein. Also provided are pharmaceutical compositions that include those compounds.

2 Claims, 8 Drawing Sheets

(56) References Cited

OTHER PUBLICATIONS

Folprechtova Denisa et al., "Enantioselective potential of teicoplanin- and vancomycin-based superficially porous particles-packed columns for supercritical fluid chromatography", Journal of Chromatography A, vol. 1612 (2019).
Folprechtova et al. "Enantioselective potential of teicoplanin- and vancomycin-based superficially porous particles-packed columns for supercritical fluid chromatography" Journal of Chromatography A, 1612, 460687 (2020).
Geoffroy P. et al., "Arynic condensation of ketone enolates 19. Synthesis of polycyclic phenylethanolamines", Tetrahedron Letters, vol. 29(12) 1385-1388(1988).
Han Yixin et al., "Method for the Direct Enantioselective Synthesis of Chiral Primary [alpha]-Amino Ketones by Catalytic [alpha]-Amination", Organic Letters, vol. 21(1) 283-286 (2019).
Han, Yixin et al. "Simple Enantioselective Syntheses of (2R,6R)-Hydroxynorketamine and Related Potential Rapid-Onset Antidepressants." *Organic letters* vol. 19,19 (2017): 5224-5227.
Hägele et al. "Enantioselective separation of Novel Psychoactive Substances using a Lux® AMP 3μm column and HPLC-UV", Journal of Pharmaceutical and Biomedical Analysis, vol. 179 (2019).
Hagele, JS, Hubner, E-M, Schmid, MG. Determination of the chiral status of different novel psychoactive substance classes by capillary electrophoresis and β-cyclodextrin derivatives. Chirality. 2020; 32 1191- 1207.
Kadkhodaei Kian et al., "Separation of enantiomers of new psychoactive substances by high-performance liquid chromatography", Journal of Separation Science, vol. 41(6) 1274-1286 (2018).
Kamenka Jean Marc et al., "Recherche de differences conformationnelles et biochimiques entre phencyclidine et ketamine—[Studies on the conformational and biochemical differences between phencyclidine and ketamine]", European Journal of Medicinal Chemistry, vol. 20(5) 419-424 (1985).
Krotulski et al. "Sample Mining and Data Mining: Combined Real-Time and Retrospective Approaches for the Identification of Emerging Novel Psychoactive Substances", Journal of Forensic Sciences 65(2), 550-562 (2020).
Lednicer D, VonVoigtlander PF, Emmert DE "4-Amino-4-arylcyclohexanones and their derivatives, a novel class of analgesics. 1. Modification of the aryl ring" J Med Chem vol. 23(4): 424-30 (1980).
Mestria et al. "Method development for the identification of methoxpropamine, 2-fluoro-deschloroketamine and deschloroketamine and their main metabolites in blood and hair and forensic application", Forensic Sci Int. 323:110817 (2021).
Michely, Julian A et al. "Biotransformation and detectability of the new psychoactive substances N,N-diallyltryptamine (DALT) derivatives 5-fluoro-DALT, 7-methyl-DALT, and 5,6-methylenedioxy-DALT in urine using GC-MS, LC-MSn, and LC-HR-MS/MS." *Analytical and bioanalytical chemistry* vol. 409,6 (2017): 1681-1695.
Michely, Julian A et al. "Dried urine spots—A novel sampling technique for comprehensive LC-MSn drug screening." *Analytica chimica acta* vol. 982 (2017): 112-121.
N-Ethyl-N-methyl-1H-indole-3-ethanamine. Accessed on SciFinder. 1 page.
Pelchowicz, Z. et al. "N-Alkylated 5-fluorotryptamines." Journal of the Chemical Society (1961): 5418-21.
Pelletier et al. "New psychoactive substance cocktail in an intensive care intoxication case elucidated by molecular networking", Clinical Toxicology (2021).
Porpiglia, Nadia et al. "Chiral separation and determination of ketamine and norketamine in hair by capillary electrophoresis." *Forensic science international* vol. 266 (2016): 304-310.
Ryosuke et al. "Studies on generic analytical conditions of illicit drugs using supercritical fluid chromatography-mass spectrometry", Masashi Kanzei Chuo Bunsekishoho, 58, 45-79 (2019).
Schotten et al. "A machine-assisted approach for the preparation of follow-on pharmaceutical compound libraries" Reaction Chemistry & Engineering vol. 3(2), 210-215 (2018).
Shao et al. "Presence of the ketamine analog of 2-fluorodeschloroketamine residues in wastewater" Drug Test Anal. Sep. 13(9):1650-1657 (2021).
Soubhye, Jalal et al. "Hybrid molecules inhibiting myeloperoxidase activity and serotonin reuptake: a possible new approach of major depressive disorders with inflammatory syndrome." *The Journal of pharmacy and pharmacology* vol. 66,8 (2014): 1122-32.
Soubhye, Jalal et al. "Structure-based design, synthesis, and pharmacological evaluation of 3-(aminoalkyl)-5-fluoroindoles as myeloperoxidase inhibitors." *Journal of medicinal chemistry* vol. 53,24 (2010): 8747-59.
Stefanescu, Paul "Syntheses of new indole compounds analogous to bufotenine", Revistade Chimie (Bucharest, Romania), 19(11), 639-42 (1968).
Stevens Cal Vin L et al., "Amino Ketone Rearrangements. VI. Synthesis of 2-Alkylamino-2-phenylcyclohexanones 1 a", Journal of Organic Chemistry, vol. 31 (8) 2593-2601 (1996).
Tang et al. "Emergence of new psychoactive substance 2-fluorodeschloroketamine: Toxicology and urinary analysis in a cluster of patients exposed to ketamine and multiple analogues", Forensic Sci Int. 312:110327 (2020).
Wang et al. "Halogen Substitution Influences Ketamine Metabolism by Cytochrome P450 2B6: In Vitro and Computational Approaches", Mol Pharm 16(2):898-906 (2019).
Wang, Shiyu; Li, Changxi "Synthesis of anesthetic compound 2-(o-fluorophenyl)-2-methylaminocyclohexanone hydrochloride (F-ketamine)", Beijing Daxue Xuebao, Ziran Kexueban (2), 116-19 (1987).
West et al. "Early Warning System for Illicit Drug Use at Large Public Events: Trace Residue Analysis of Discarded Drug Packaging Samples", J Am Soc Mass Spectrom. vol 32(10):2604-2614(2021).
Yang Xiaoyu et al., "Direct Asymmetric Amination of [alpha]-Branched Cyclic Ketones Catalyzed by a Chiral Phosphoric Acid", Journal of the American Chemical Society, vol. 137(9) 3205-3208 (2015).
Kuhnz et al., "Predicting the Oral Bioavailability of 19-nortestosterone Progestins in vivo from Their Metabolic Stability in Human Liver Microsomal Preparations in vitro", Drug Metabolism and Disposition, vol. 26 (11) 1120-1127 (1998).
Lipton, Stuart A, "Failures and Successes of NMDA Receptor Antagonists: Molecular Basis for the Use of Open-channel Blockers like Memantine in the Treatment of Acute and Chronic Neurologic Insults", NeuroRx, vol. 1(1) 101-110 (2004).
Olivares et al., "N-methyl D-aspartate (NMDA) Receptor Antagonists and Memantine Treatment for Alzheimer's Disease, Vascular Dementia and Parkinson's Disease", Curr Alzheimer Res, vol. 9 (6) 746-758 (2012).
Maurer et al., "Current Use of PSMA-PET in Prostate Cancer Management", Nat Rev Urol., vol. 13 (4) 226-235 (2016).
Obach, Scott R, "Prediction of Human Clearance of Twenty-nine Drugs from Hepatic Microsomal Intrinsic Clearance Data: An Examination of in vitro Half-life Approach and Nonspecific Binding to Microsomes", Drug Metab Dispos, vol. 27 (11) 1350-1359 (1999).
Hakkola, J., Hukkanen, J., Turpeinen, M et al. Inhibition and induction of CYP enzymes in humans: an update. Arch Toxicol 94, 3671-3722 (2020).
Setola, V., Roth, B.L. (2006). The Emergence of 5-HT2B Receptors as Targets to Avoid in Designing and Refining Pharmaceuticals. In: Roth, B.L. (eds) The Serotonin Receptors. The Receptors. Humana Press.

METHODS OF TREATING MOOD DISORDERS

CROSS-REFERENCE TO RELATED APPLICATIONS

This application is a continuation of U.S. application Ser. No. 17/404,923, filed Aug. 17, 2021, which is a continuation-in-part of International Application No. PCT/US2021/018534, filed Feb. 18, 2021, which claims the benefit of, and priority to, U.S. Provisional Application No. 62/978,075, filed on Feb. 18, 2020, the contents of each of which are incorporated herein by reference in their entirety.

BACKGROUND

Depression is a common psychological problem and refers to a mental state of low mood and aversion to activity. Various symptoms associated with depression include persistent anxious or sad feelings, feelings of helplessness, hopelessness, pessimism, and/or worthlessness, low energy, restlessness, irritability, fatigue, loss of interest in pleasurable activities or hobbies, excessive sleeping, overeating, appetite loss, Insomnia, thoughts of suicide, and suicide attempts. The presence, severity, frequency, and duration of the above-mentioned symptoms vary on a case-by-case basis.

Approximately one third of patients with major depressive disorder (MDD) fail to achieve remission of their symptoms, even after multiple rounds of treatment with several known classes of antidepressants, including selective serotonin reuptake inhibitors (SSRIs) (Rush et al. 2006). This high prevalence of treatment-resistant depression (TRD) makes clear the need for new, more efficacious pharmacotherapies for depression that will target new mechanisms and/or patient populations.

Tryptamines are monoamine alkaloids that contain an indole ring and are structurally similar to the amino acid tryptophan, from which the name derives.

There are a significant number of tryptamine compounds that include naturally occurring compounds and chemical derivatives with similar structure that may be ring unsubstituted or ring substituted. Many tryptamines are $5HT_{2A}$ receptor agonists and/or modulators of other serotonin receptors and are known to be psychoactive and, in many cases, cause prolonged hallucinations. The most well-known tryptamines are psychedelic compounds, including compounds derived from entheogenic fungi (psilocybin and psilocin), N,N-dimethyltryptamine (DMT), lysergic acid diethylamide (LSD), 5-methoxy-N,N-dimethyltryptamine (5-MeO-DMT), bufotenin, and ibogaine. These compounds are known to have significant effects on thought, perception, and behavior. However, these compounds are currently classified as Schedule I drugs under the Controlled Substances Act due to their high abuse potential, no accepted medical use, and lack of established safety. Moreover, tryptamines are metabolized by a number of pathways, in some cases including monoamine oxidase, limiting the oral bioavailability of some compounds and resulting in very short durations of action. Conversely, other tryptamines have very long durations of action, which makes them challenging to use in a guided therapy setting, where supervised sessions of many hours in duration are costly for patients and inconvenient for healthcare providers.

Accordingly, there remains a need for safe and effective tryptamine compounds that can reliably be used for the treatment of mood disorders.

SUMMARY

The present disclosure includes compound 2:

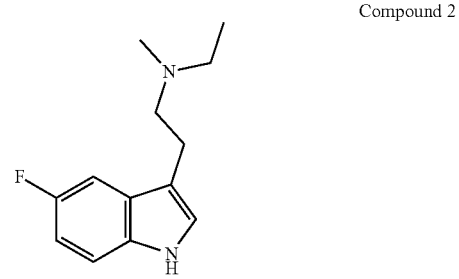 [SMILES: CCN(C)CCc1c[nH]c2ccc(F)cc12]

Compound 2 or a pharmaceutically acceptable salt thereof.

Additionally, the present disclosure includes pharmaceutical compositions of compound 2 and methods of using the same.

Additionally, the present disclosure includes methods of treating mood disorders in a patient in need thereof, comprising administering an effective amount of compound 2 or compound 4:

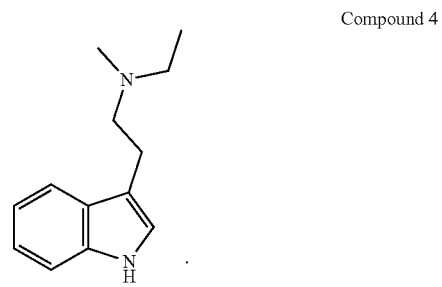

Compound 4 or a pharmaceutically acceptable salt thereof.

For example, provided herein are methods and compositions directed to treating a mood disorder by administering to a patient in need thereof a pharmaceutical composition comprising an effective amount of compound 2 or compound 4, or a pharmaceutically acceptable salt thereof. In embodiments, the methods and compositions may treat mood disorders that include depressive disorders, bipolar and related disorders, substance-related disorders, and/or anxiety disorders.

In embodiments, the methods and compositions may treat mood disorders that include obsessive-compulsive and related disorders. In embodiments, the methods and compositions may treat mood disorders that include trauma- and stressor-related disorders. In embodiments, the methods and compositions may treat mood disorders that include feeding and eating disorders. In embodiments, the methods and compositions may treat mood disorders that include neurocognitive disorders. In embodiments, the methods and compositions may treat mood disorders that include neurodevelopmental disorders. In embodiments, the methods and compositions may treat mood disorders that include personality disorders. In embodiments, the methods and compositions may treat mood disorders that include sexual dysfunctions. In embodiments, the methods and compositions may treat mood disorders that include gender dysphoria.

DETAILED DESCRIPTION

Figure 1:
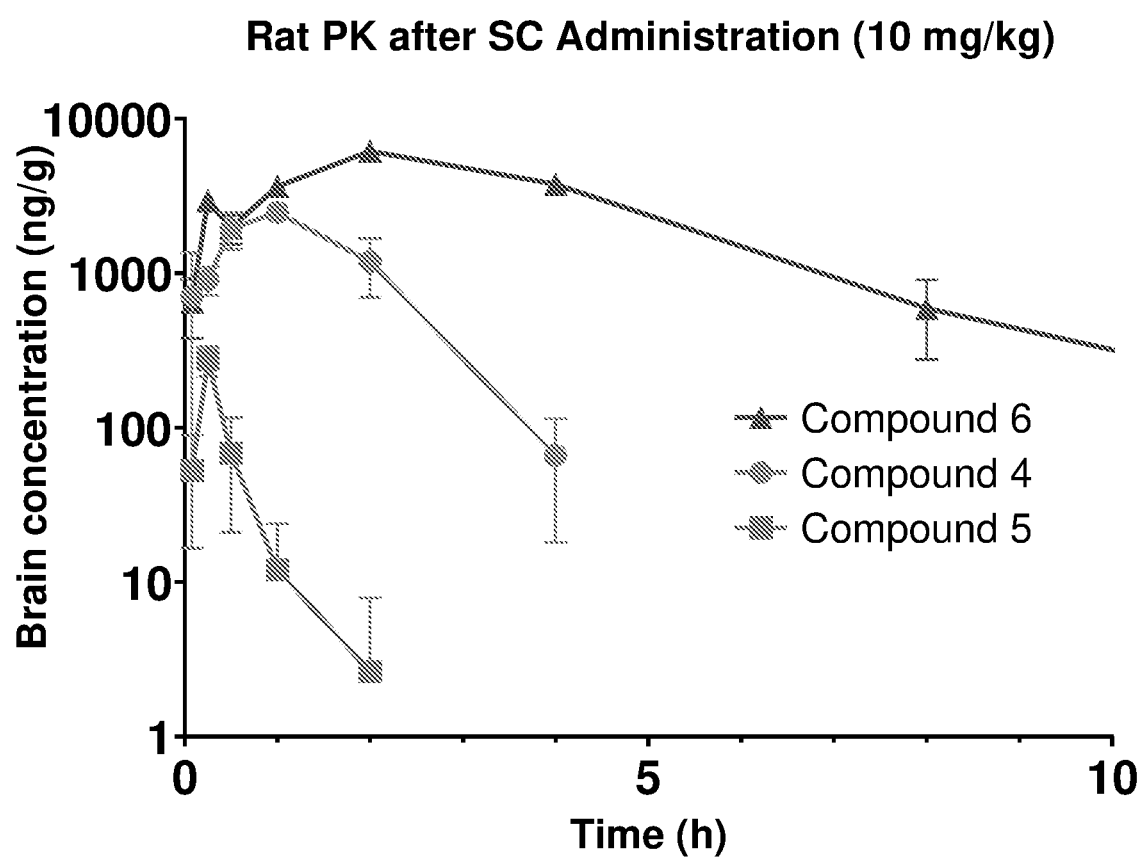
FIG. 1 depicts a graph of concentration versus time comparison for Compounds 4, 5, and 6 in rat brain after subcutaneous administration (dose 10 mg/kg). Values are expressed as mean+/− standard error of the mean.

The present disclosure includes a compound according to Formula I:

I or a pharmaceutically acceptable salt thereof, wherein $R_1$ is optionally substituted $C_1$-$C_4$ aliphatic;

$R_2$ is optionally substituted $C_1$-$C_4$ aliphatic;

$R_{26}$ is selected from the group consisting of hydrogen, halogen, —CN, —OH, $C_1$-$C_3$ alkoxy, $C_1$-$C_3$ haloalkyl, OAc, —OPO(OH)$_2$ and NH$_2$.

In some embodiments, $R_1$ is selected from the group consisting of Me, Et, nPr, iPr, cyclopropyl, allyl, isobutyl, cyclopropylmethyl. In some embodiments, $R_2$ is selected from the group consisting of Me, Et, nPr, iPr, cyclopropyl, allyl, isobutyl, cyclopropylmethyl.

In some embodiments, $R_{26}$ is selected from the group consisting of hydrogen, F, Cl, Br, I, CF$_3$, Me, CN, OMe, OH, OAc, and NH$_2$. In some embodiments, R26 is selected from the group consisting of F, Cl, Br, I, CF$_3$, Me, CN, OMe, OH, OAc, and NH$_2$. In some embodiments, R26 is halogen. In some embodiments, $R_{26}$ is fluoro. In some embodiments, $R_{26}$ is chloro. In some embodiments, $R_{26}$ is bromo. In some embodiments, $R_{26}$ is iodo.

In embodiments, the present disclosure includes a compound selected from the group consisting of:

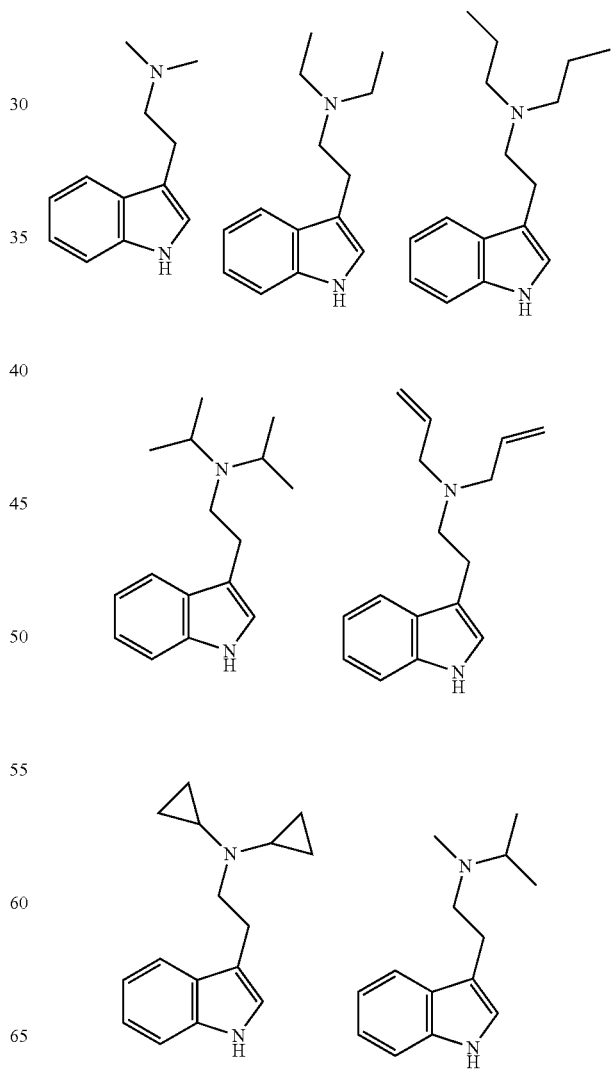

-continued
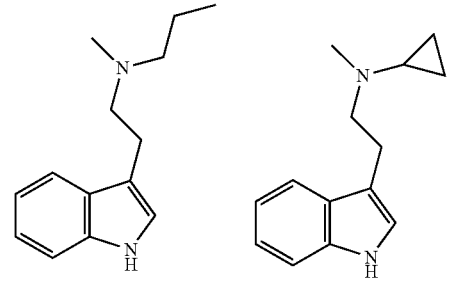
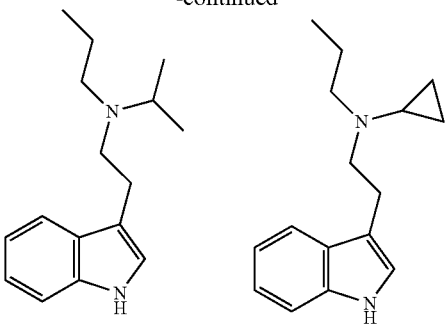
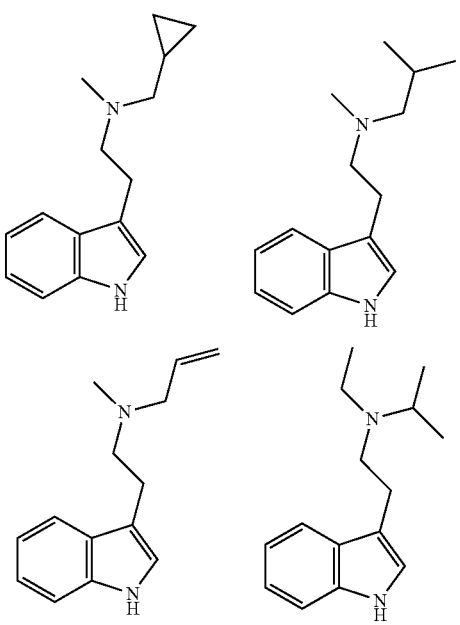
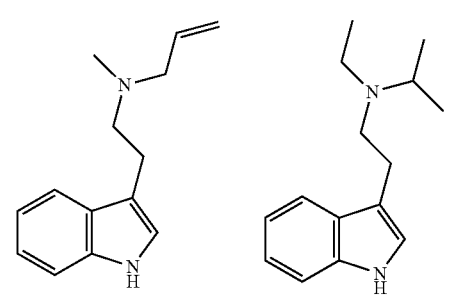
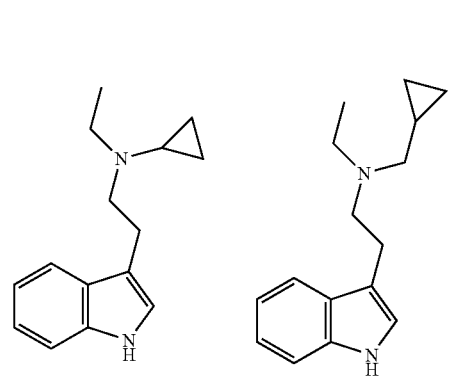
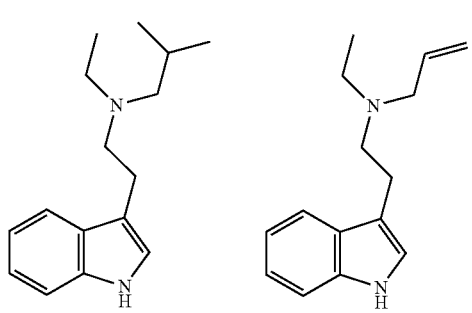
-continued
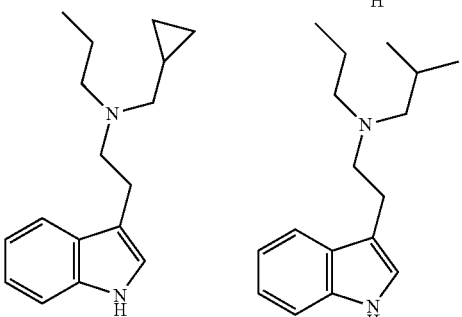
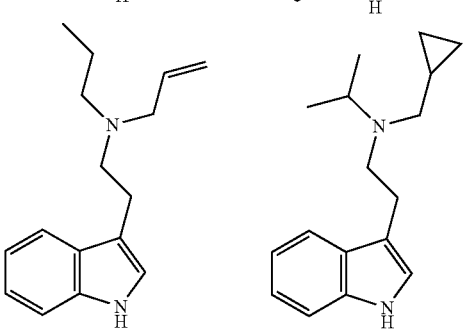
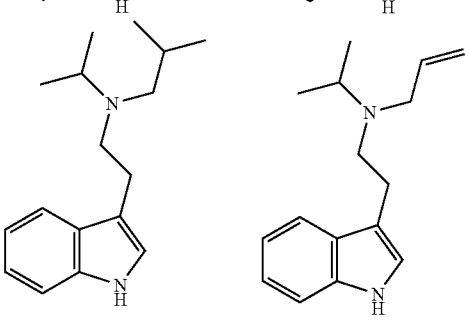
or a pharmaceutically acceptable salt thereof.
In embodiments, the present disclosure includes a compound selected from the group consisting of:
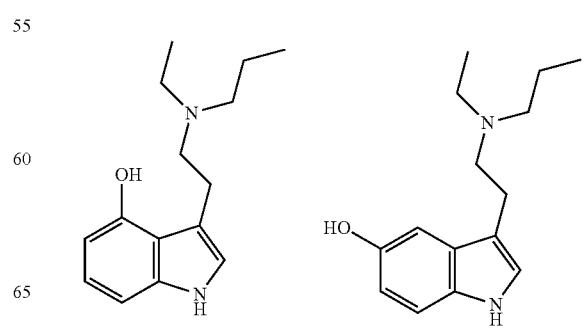

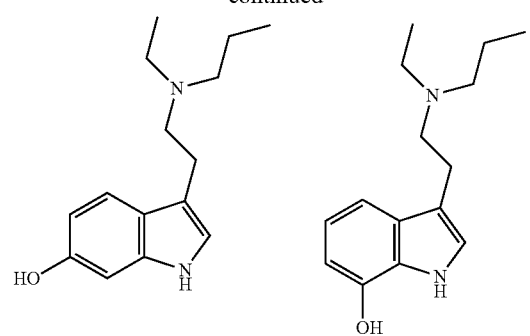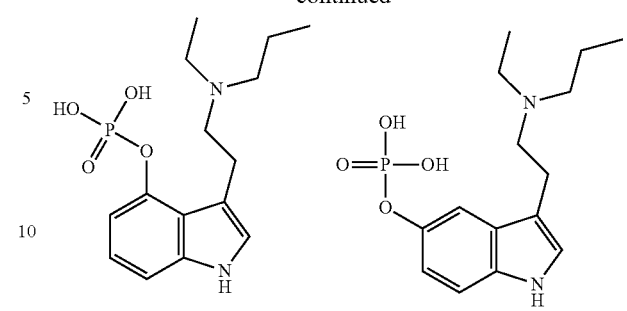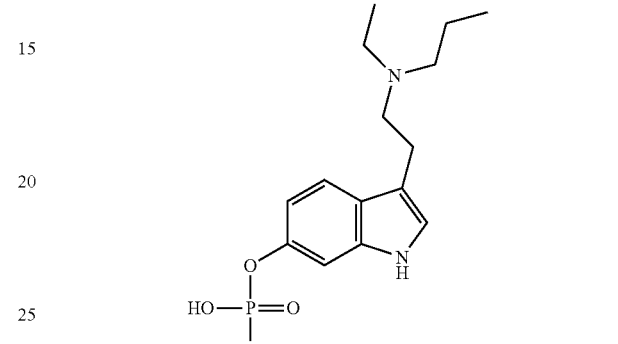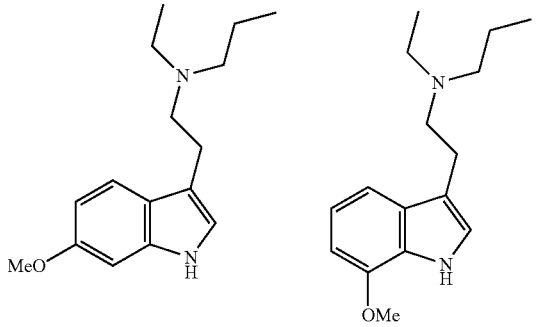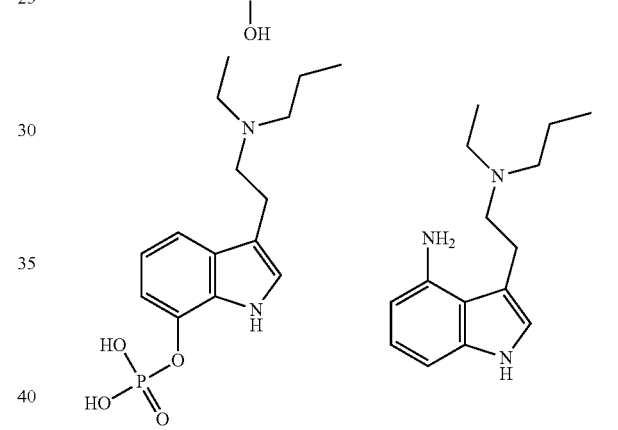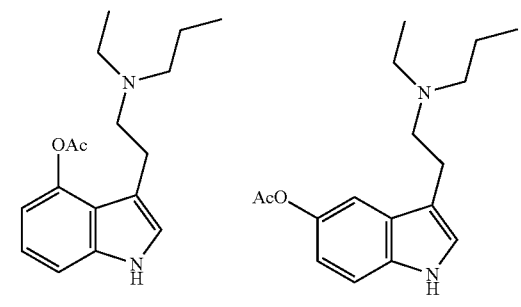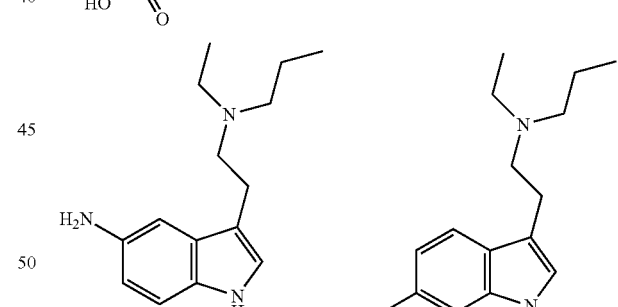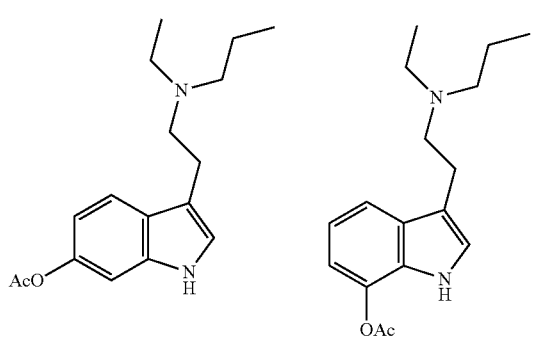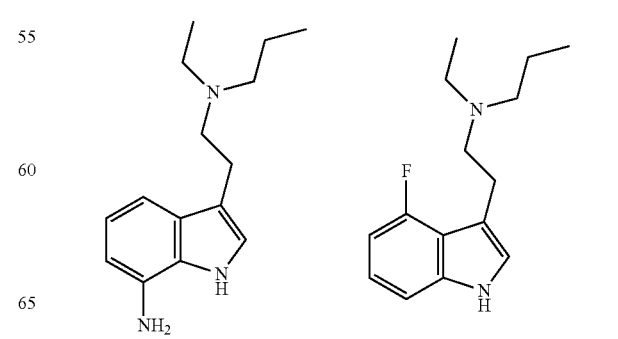

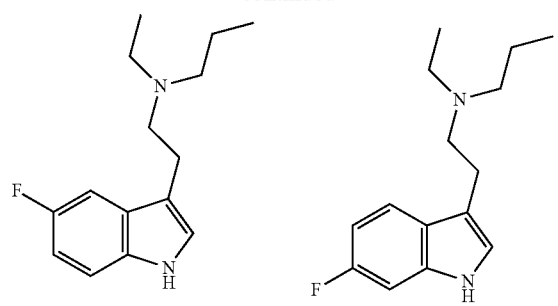
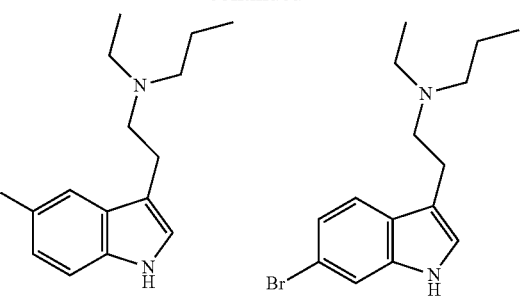
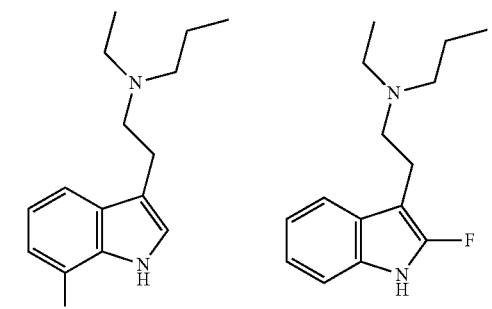
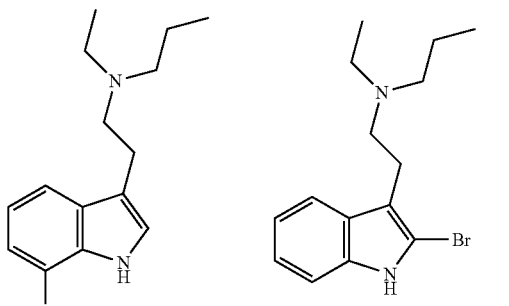
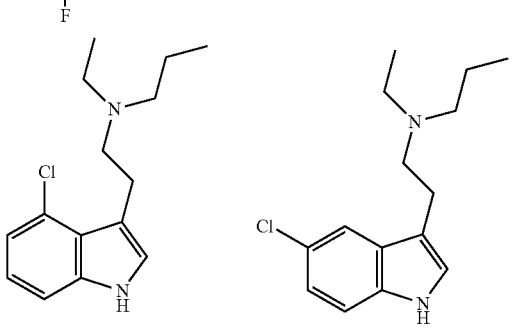
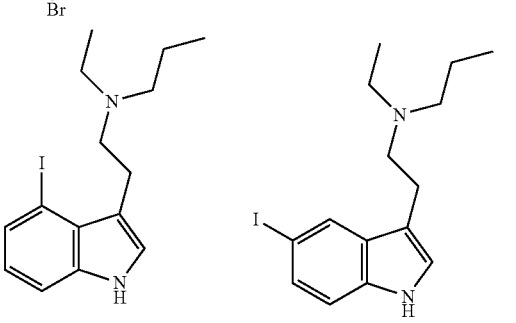
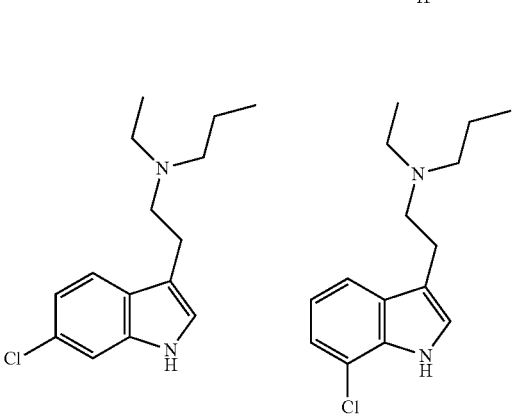
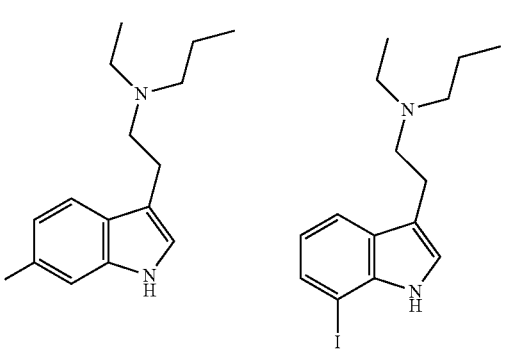
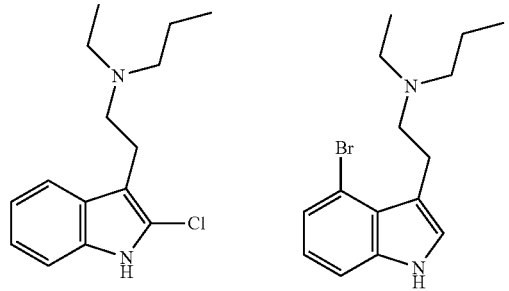
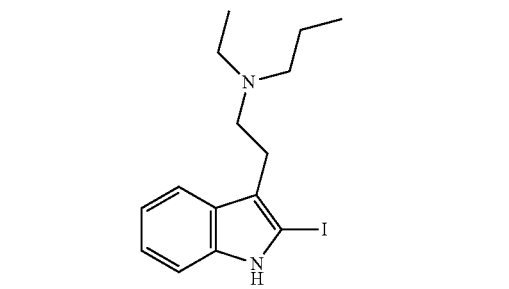

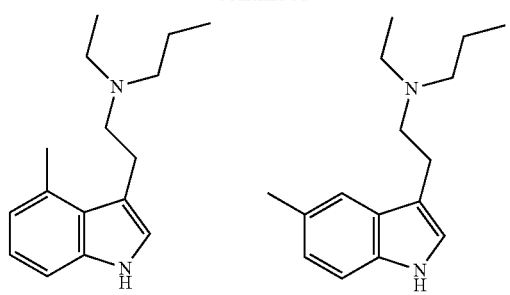
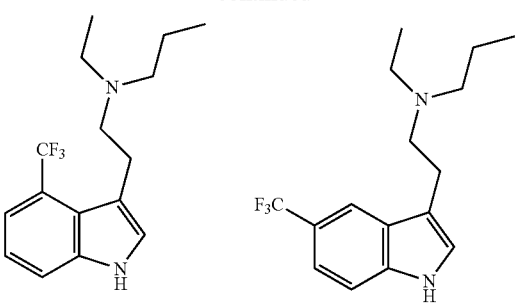
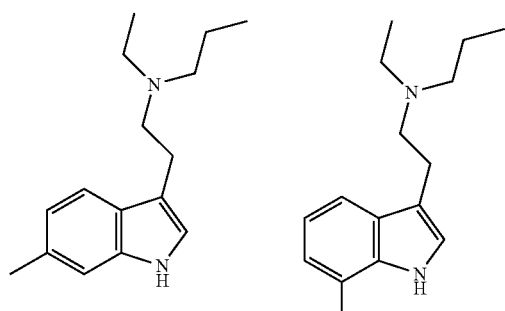
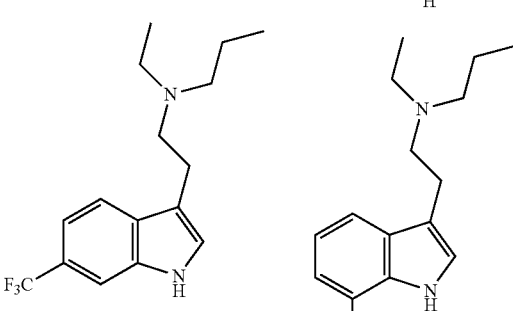
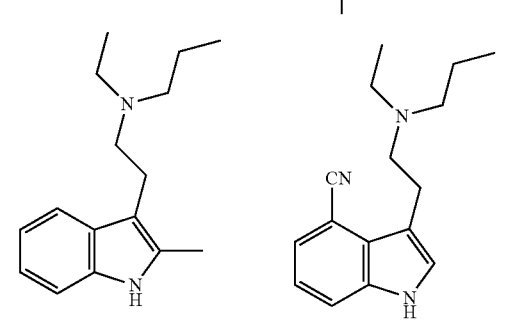
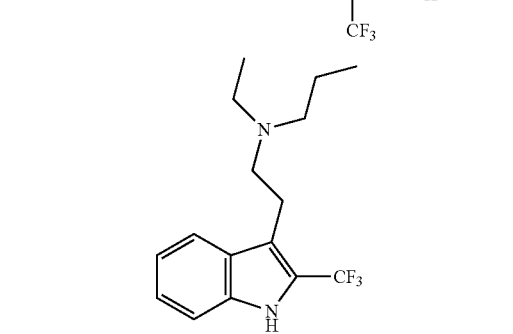
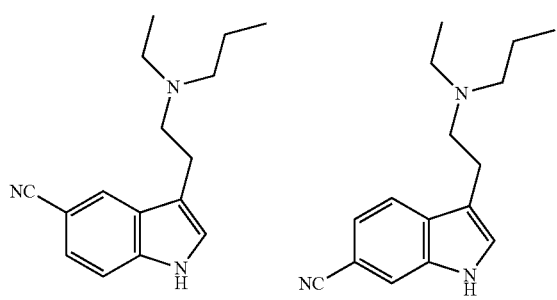
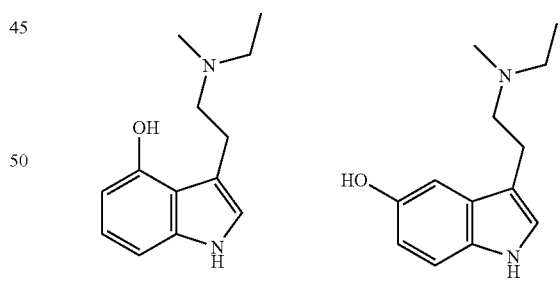
or a pharmaceutically acceptable salt thereof.
In embodiments, the present disclosure includes a compound selected from the group consisting of:
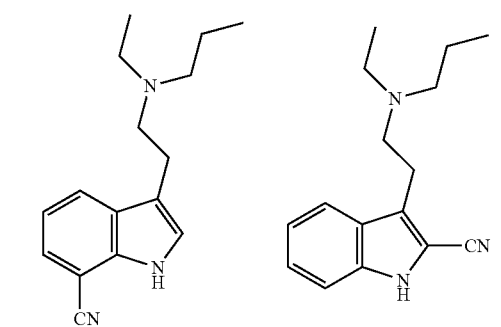
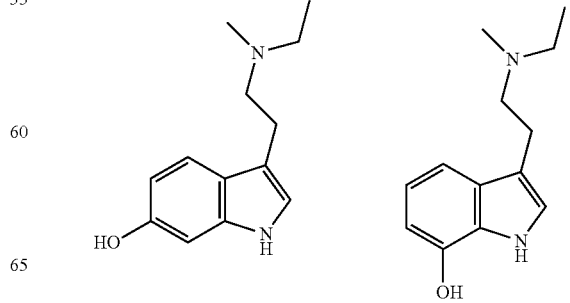

-continued
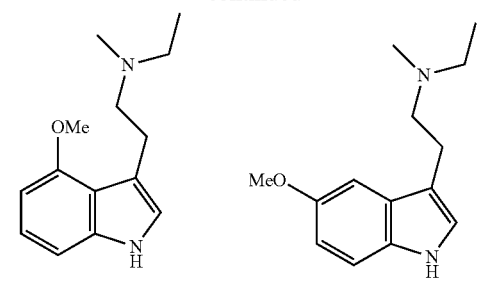
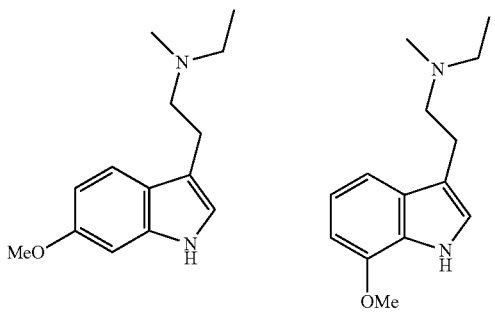
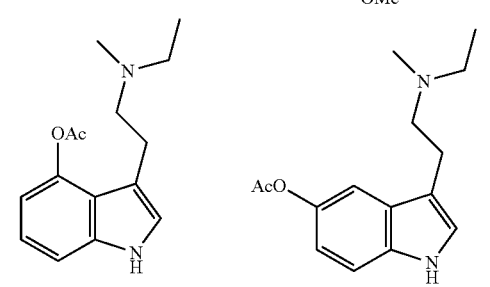
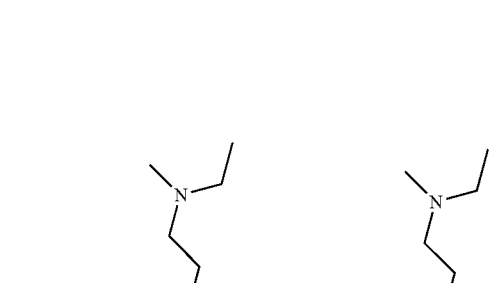
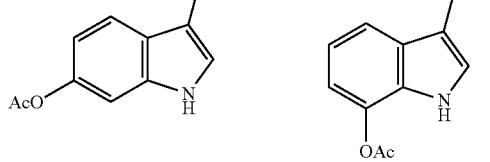
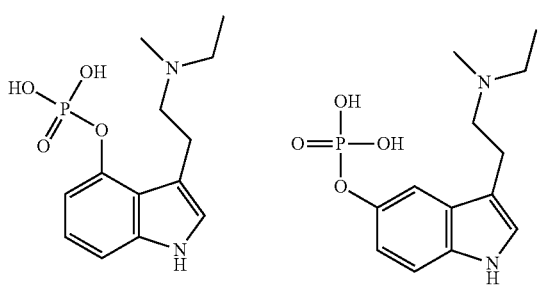
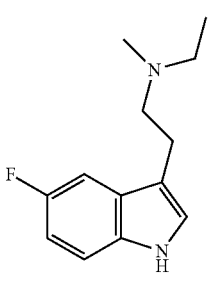
-continued
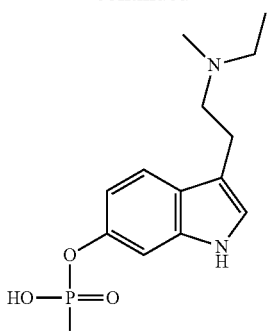
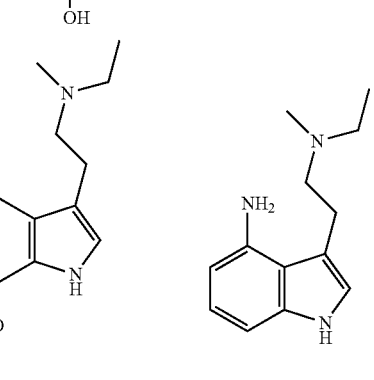
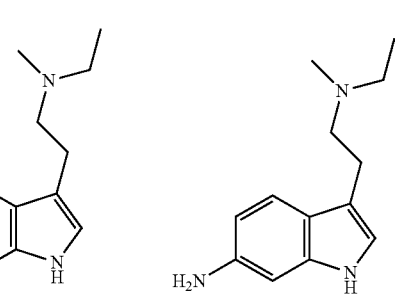
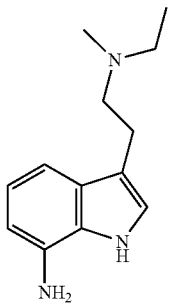
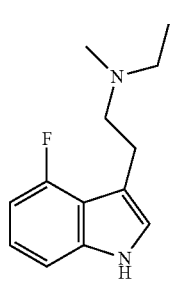
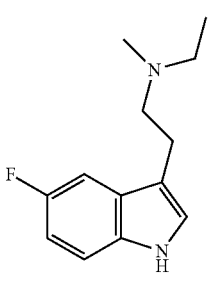
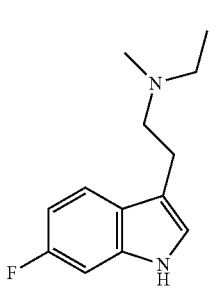

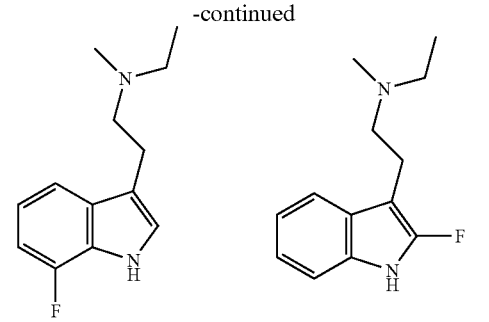
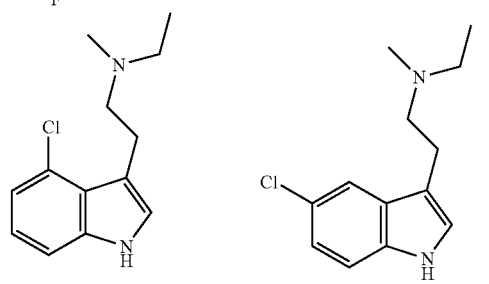
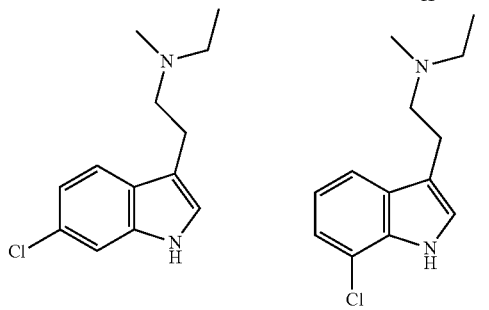
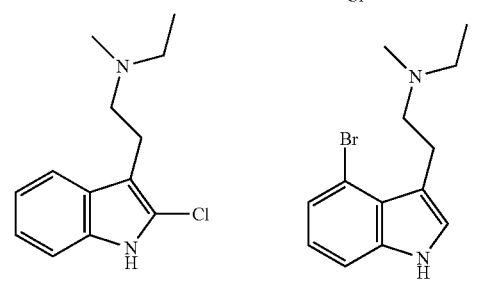
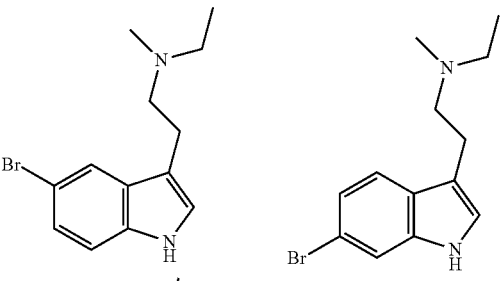
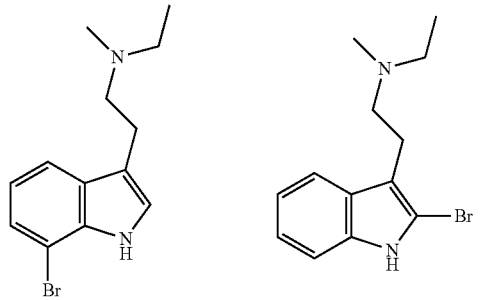
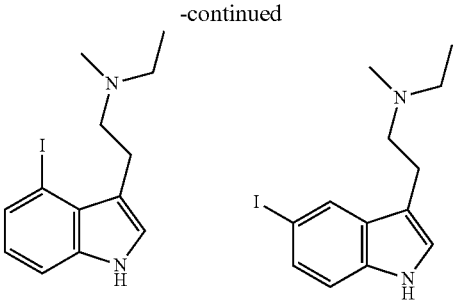
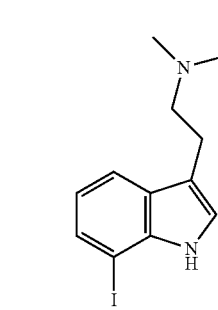
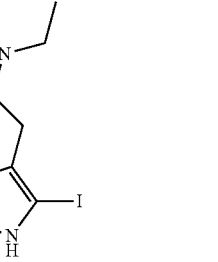
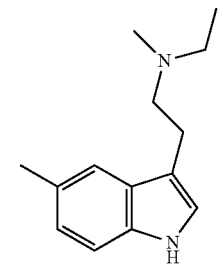
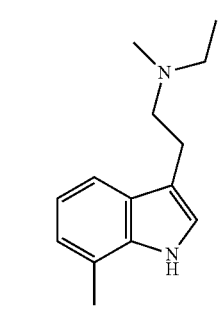
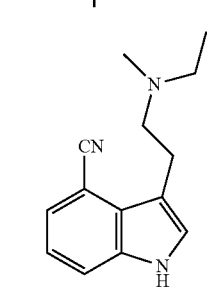

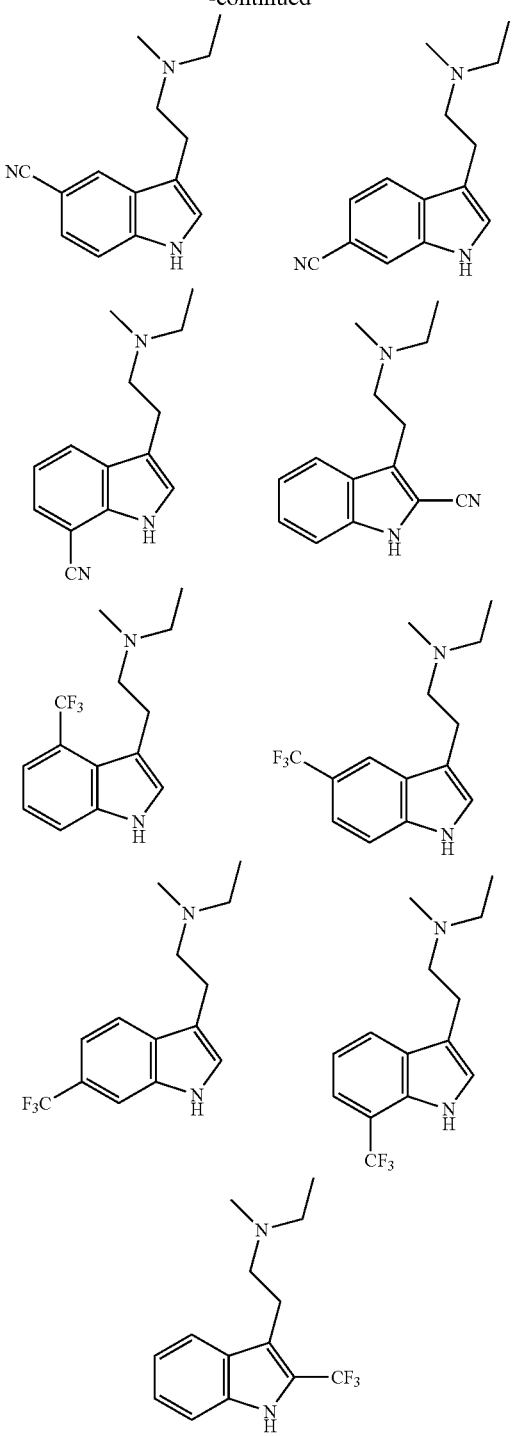

or a pharmaceutically acceptable salt thereof.

Described herein are methods and compositions for treating a mood disorder by administering to a patient in need thereof a compound disclosed herein. Also provided are pharmaceutical compositions that include a compound disclosed herein.

In embodiments, the methods and compositions may be used to treat a mood disorder including depressive disorders, e.g., major depressive disorder, persistent depressive disorder, postpartum depression, premenstrual dysphoric disorder, seasonal affective disorder, psychotic depression, disruptive mood dysregulation disorder, substance/medication-induced depressive disorder, and depressive disorder due to another medical condition.

In some embodiments, depression conditions include major depressive disorder and dysthymic disorder. In some embodiments, depression conditions develop under unique circumstances, including, but are not limited to, psychotic depression, postpartum depression, seasonal affective disorder (SAD), mood disorder, depressions caused by chronic medical conditions such as cancer or chronic pain, chemotherapy, chronic stress, post traumatic stress disorders, and bipolar disorder (or manic depressive disorder). In some embodiments, depression conditions that are expected to be treated according to this aspect of the present disclosure include, but are not limited to, major depressive disorder, dysthymic disorder, psychotic depression, postpartum depression, premenstrual syndrome, premenstrual dysphoric disorder, seasonal affective disorder (SAD), anxiety, mood disorder, depressions caused by chronic medical conditions such as cancer or chronic pain, chemotherapy, chronic stress, post traumatic stress disorders, and bipolar disorder (or manic depressive disorder).

Also provided herein are methods of treating refractory depression, e.g., patients suffering from a depressive disorder that does not, and/or has not, responded to adequate courses of at least one, or at least two, other antidepressant compounds or therapeutics. For example, provided herein is a method of treating depression in a treatment resistant patient, comprising a) optionally identifying the patient as treatment resistant and b) administering an effective dose of a disclosed compound. As used herein "depressive disorder" encompasses refractory depression. In some embodiments, refractory depression occurs in patients suffering from depression who are resistant to standard pharmacological treatments, including tricyclic antidepressants, MAOIs, SSRIs, and double and triple uptake inhibitors and/or anxiolytic drugs, as well non-pharmacological treatments such as psychotherapy, electroconvulsive therapy, vagus nerve stimulation and/or transcranial magnetic stimulation. In some embodiments, a treatment resistant-patient may be identified as one who fails to experience alleviation of one or more symptoms of depression (e.g., persistent anxious or sad feelings, feelings of helplessness, hopelessness, pessimism) despite undergoing one or more standard pharmacological or non-pharmacological treatment. In certain embodiments, a treatment-resistant patient is one who fails to experience alleviation of one or more symptoms of depression despite undergoing treatment with two different antidepressant drugs. In other embodiments, a treatment-resistant patient is one who fails to experience alleviation of one or more symptoms of depression despite undergoing treatment with four different antidepressant drugs. In some embodiments, a treatment-resistant patient may also be identified as one who is unwilling or unable to tolerate the side effects of one or more standard pharmacological or non-pharmacological treatment.

In some embodiments, symptoms associated with depression include, but are not limited to, persistent anxious or sad feelings, feelings of helplessness, hopelessness, pessimism, and/or worthlessness, low energy, restlessness, irritability, fatigue, loss of interest in pleasurable activities or hobbies, excessive sleeping, overeating, appetite loss, insomnia, thoughts of suicide, or suicide attempts. In some embodiments, various symptoms associated with anxiety include fear, panic, heart palpitations, shortness of breath, fatigue, nausea, and headaches among others. In addition, patients suffering from any form of depression often experience anxiety. It is expected that the methods of the present condition can be used to treat anxiety or any of the symptoms thereof. In some embodiments, presence, severity, frequency, and duration of symptoms of depression vary on a case to case basis.

In embodiments, the methods and compositions may be used to treat a mood disorder including bipolar and related disorders, e.g., bipolar I disorder, bipolar II disorder, cyclothymic disorder, substance/medication-induced bipolar and related disorder, and bipolar and related disorder due to another medical condition.

In embodiments, the methods and compositions may be used to treat a mood disorder including substance-related disorders, e.g., preventing a substance use craving, diminishing a substance use craving, and/or facilitating substance use cessation or withdrawal. Substance use disorders involve abuse of psychoactive compounds such as alcohol, caffeine, *cannabis*, inhalants, opioids, sedatives, hypnotics, anxiolytics, stimulants, nicotine and tobacco. As used herein "substance" or "substances" are psychoactive compounds which can be addictive such as alcohol, caffeine, *cannabis*, hallucinogens, inhalants, opioids, sedatives, hypnotics, anxiolytics, stimulants, nicotine and tobacco. For example, the methods and compositions may be used to facilitate smoking cessation or cessation of opioid use.

In embodiments, the methods and compositions may be used to treat a mood disorder including anxiety disorders, e.g., separation anxiety disorder, selective mutism, specific phobia, social anxiety disorder (social phobia), panic disorder, panic attack, agoraphobia, generalized anxiety disorder, substance/medication-induced anxiety disorder, and anxiety disorder due to another medical condition.

In embodiments, the methods and compositions may be used to treat a mood disorder including obsessive-compulsive and related disorders, e.g., obsessive-compulsive disorder, body dysmorphic disorder, hoarding disorder, trichotillomania (hair-pulling disorder), excoriation (skin-picking) disorder, substance/medication-induced obsessive-compulsive and related disorder, and obsessive-compulsive and related disorder due to another medical condition.

In embodiments, the methods and compositions may be used to treat a mood disorder including trauma- and stressor-related disorders, e.g., reactive attachment disorder, disinhibited social engagement disorder, posttraumatic stress disorder, acute stress disorder, and adjustment disorders.

In embodiments, the methods and compositions may be used to treat a mood disorder including feeding and eating disorders, e.g., anorexia nervosa, bulimia nervosa, binge-eating disorder, pica, rumination disorder, and avoidant/restrictive food intake disorder.

In embodiments, the methods and compositions may be used to treat a mood disorder including neurocognitive disorders, e.g., delirium, major neurocognitive disorder, mild neurocognitive disorder, major or mild neurocognitive disorder due to Alzheimer's disease, major or mild frontotemporal neurocognitive disorder, major or mild neurocognitive disorder with Lewy bodies, major or mild vascular neurocognitive disorder, major or mild neurocognitive disorder due to traumatic brain injury, substance/medication-induced major or mild neurocognitive disorder, major or mild neurocognitive disorder due to HIV infection, major or mild neurocognitive disorder due to prion disease, major or mild neurocognitive disorder due to Parkinson's disease, major or mild neurocognitive disorder due to Huntington's disease, major or mild neurocognitive disorder due to another medical condition, and major or mild neurocognitive disorder due to multiple etiologies.

In embodiments, the methods and compositions may be used to treat a mood disorder including neurodevelopmental disorders, e.g., autism spectrum disorder, attention-deficit/hyperactivity disorder, stereotypic movement disorder, tic disorders, Tourette's disorder, persistent (chronic) motor or vocal tic disorder, and provisional tic disorder. In some embodiments, a variety of other neurological conditions are expected to be treated according to the methods of the present disclosure. In some embodiments, neurological conditions include, but are not limited to, a learning disorder, autistic disorder, attention-deficit hyperactivity disorder, Tourette's syndrome, phobia, post-traumatic stress disorder, dementia, AIDS dementia, Alzheimer's disease, Parkinson's disease, spasticity, myoclonus, muscle spasm, bipolar disorder, a substance abuse disorder, urinary incontinence, and schizophrenia.

In embodiments, the methods and compositions may be used to treat a mood disorder including personality disorders, e.g., borderline personality disorder.

In embodiments, the methods and compositions may be used to treat a mood disorder including sexual dysfunctions, e.g., delayed ejaculation, erectile disorder, female orgasmic disorder, female sexual interest/arousal disorder, genito-pelvic pain/penetration disorder, male hypoactive sexual desire disorder, premature (early) ejaculation, and substance/medication-induced sexual dysfunction.

In embodiments, the methods and compositions may be used to treat a mood disorder including gender dysphoria.

In embodiments provided are methods and compositions for treating a mood disorder by administering to a subject in need thereof an effective amount of ethylpropyltryptamine (EPT; Compound 1) or a pharmaceutically acceptable salt thereof.

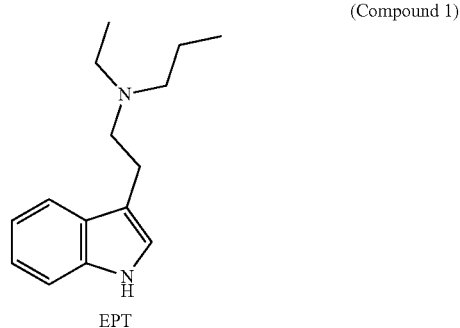 [SMILES: CCCN(CC)CCc1c[nH]c2ccccc12]

(Compound 1)

EPT

In other embodiments provided are methods and compositions for treating a mood disorder by administering to a subject in need thereof an effective amount of methylethyltryptamine (MET; Compound 2) or a pharmaceutically acceptable salt thereof.

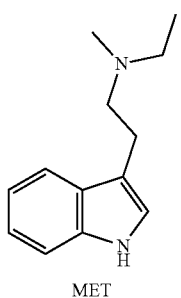
(Compound 2)
MET
In other embodiments provided are methods and compositions for treating a mood disorder by administering to a subject in need thereof an effective amount of a compound disclosed herein selected from the following structures:
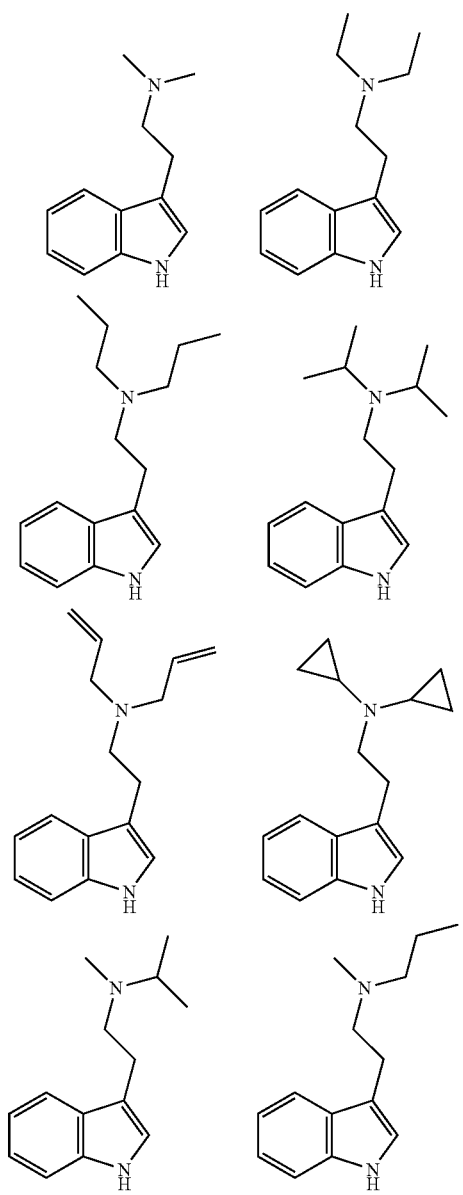

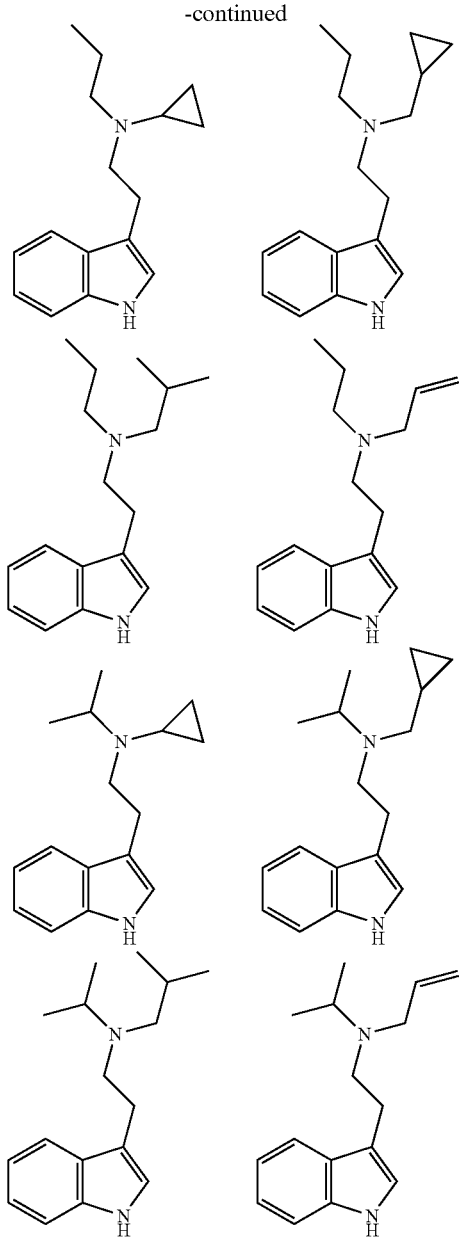
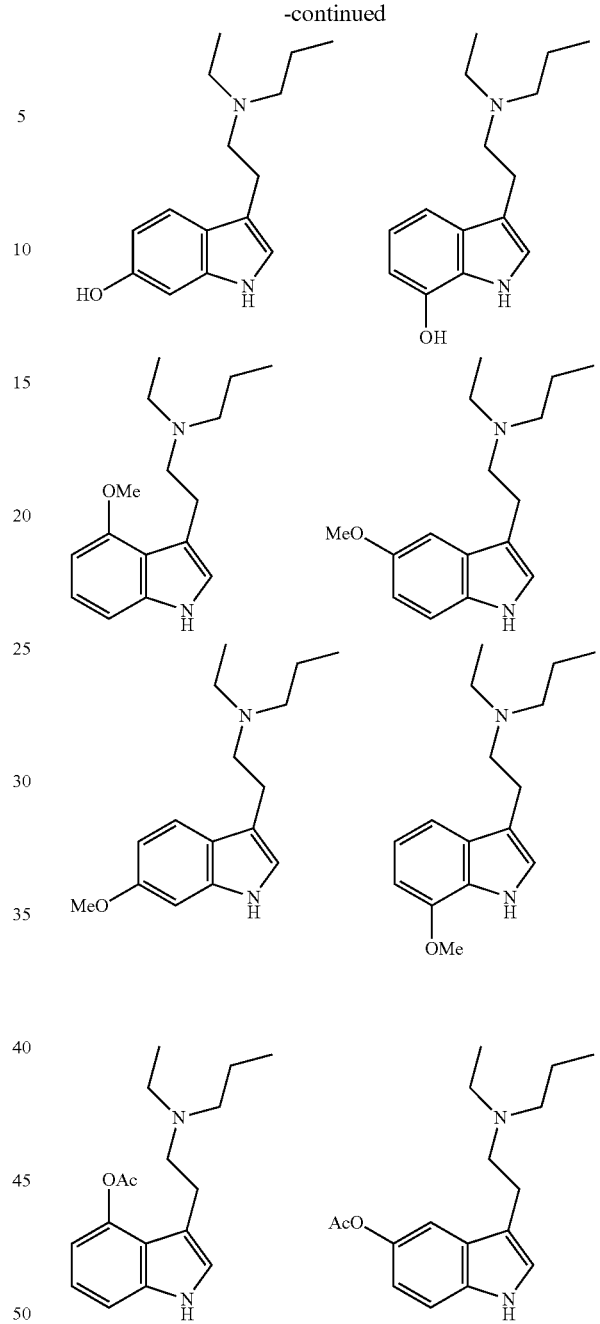
or a pharmaceutically acceptable salt thereof.
In other embodiments provided are methods and compositions for treating a mood disorder by administering to a subject in need thereof an effective amount of a compound disclosed herein selected from the following structures:
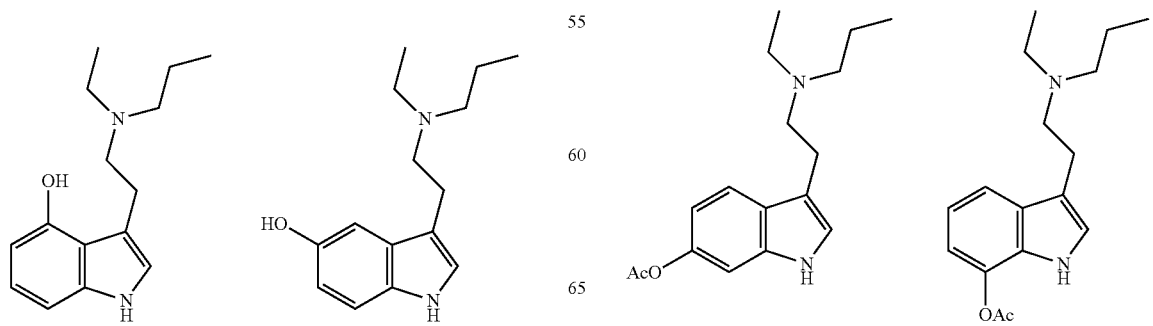

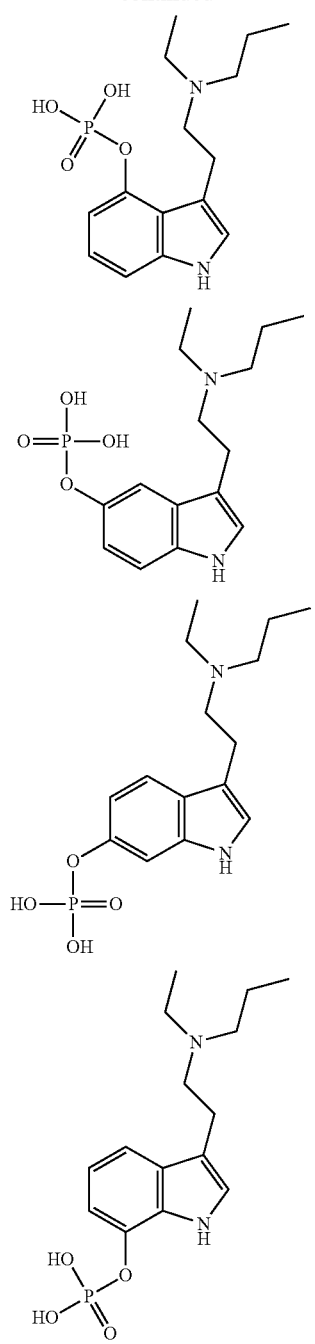
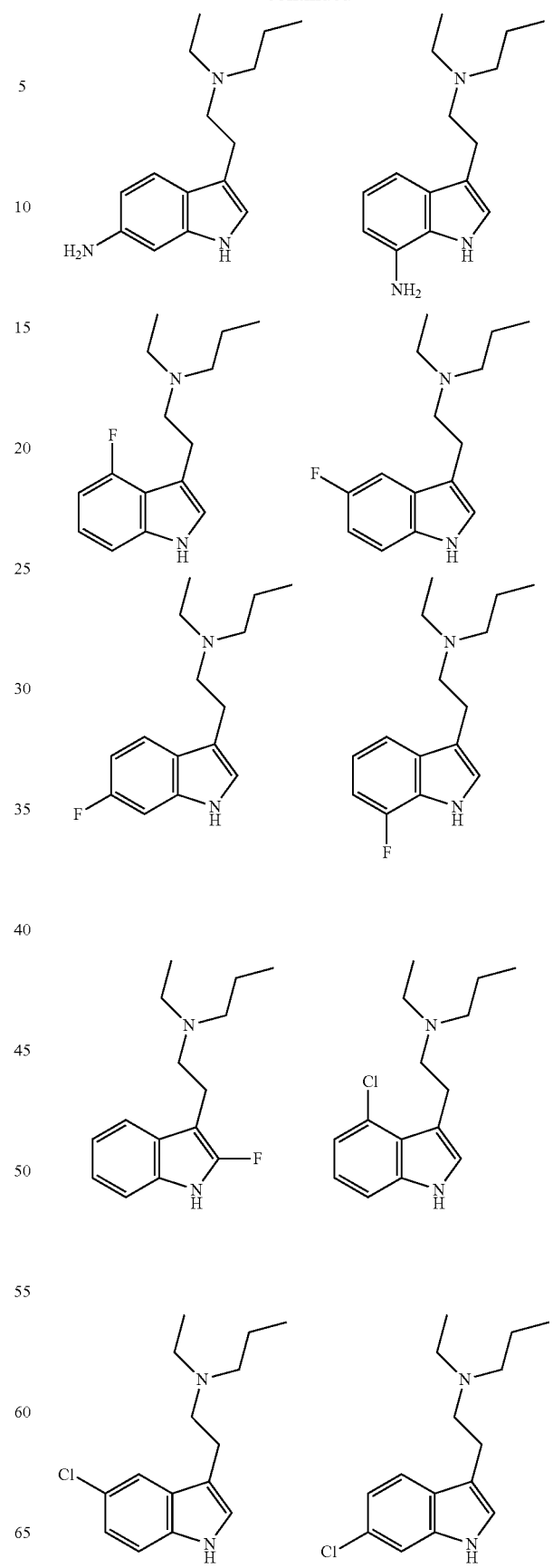

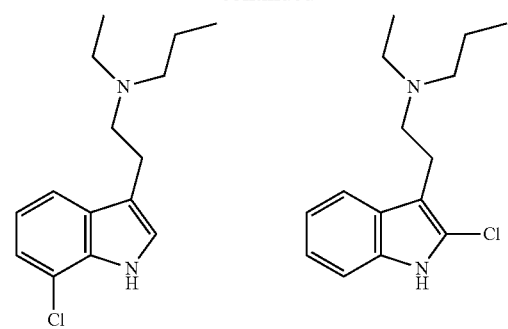
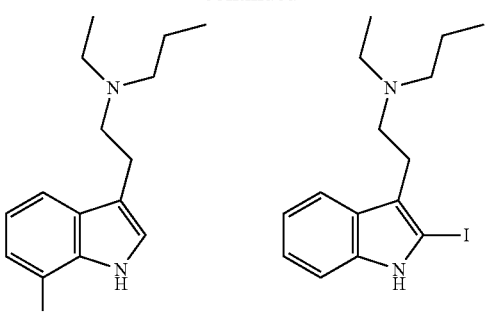
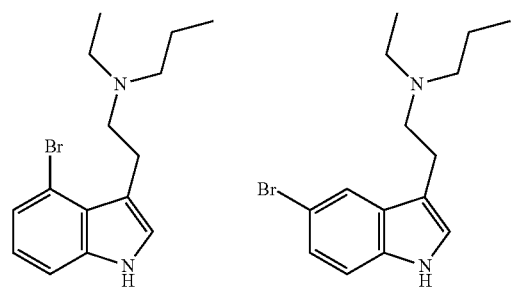
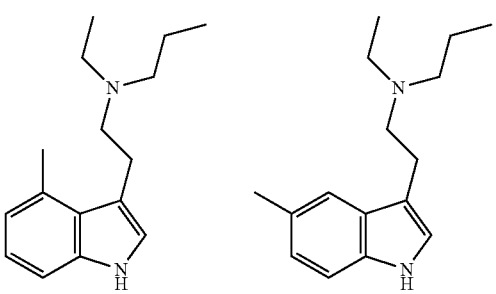
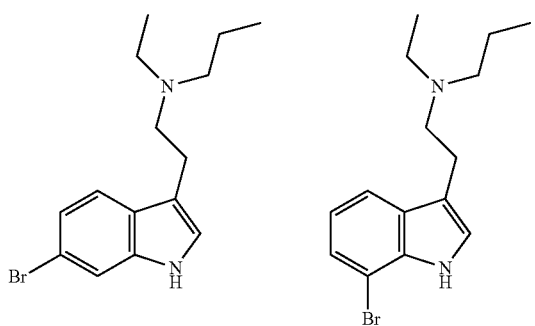
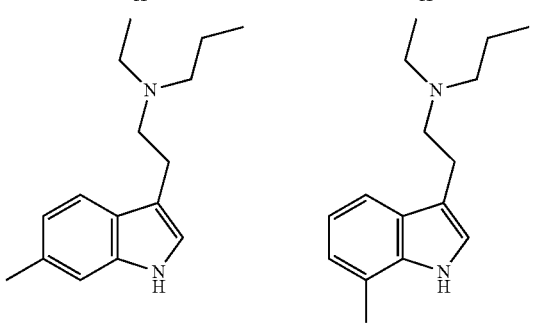
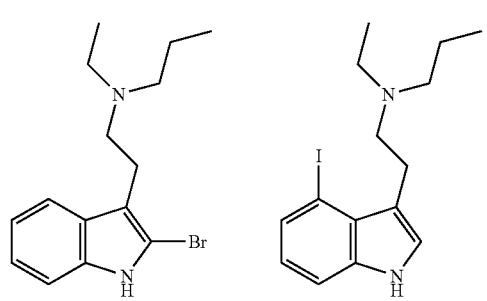
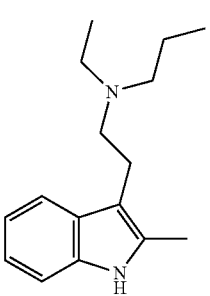
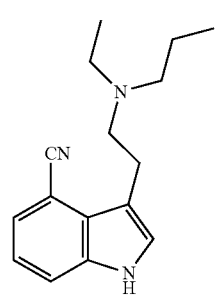
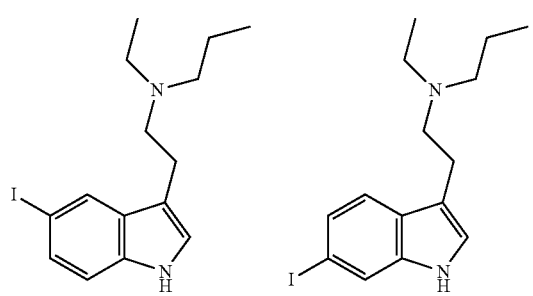
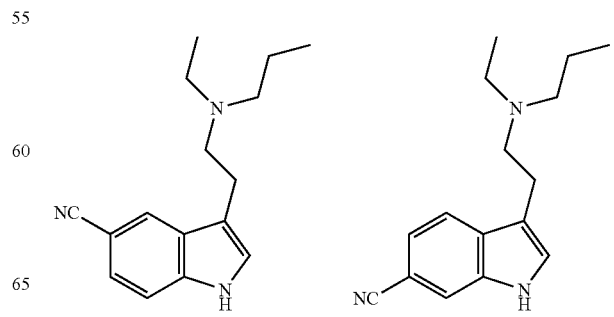

-continued
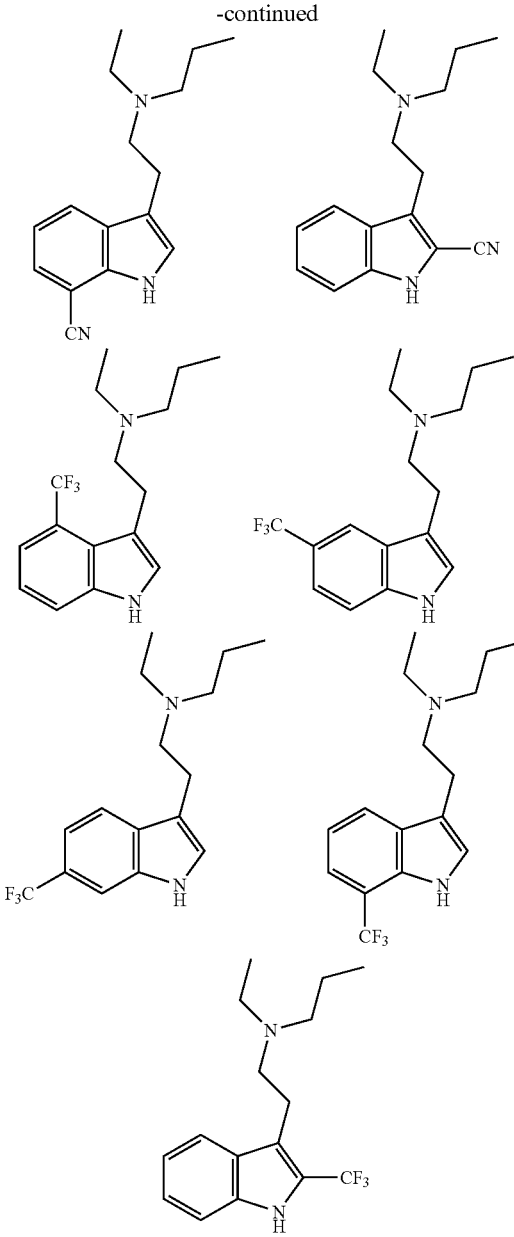
or a pharmaceutically acceptable salt thereof.
In other embodiments provided are methods and compositions for treating a mood disorder by administering to a subject in need thereof an effective amount of a compound disclosed herein selected from the following structures:
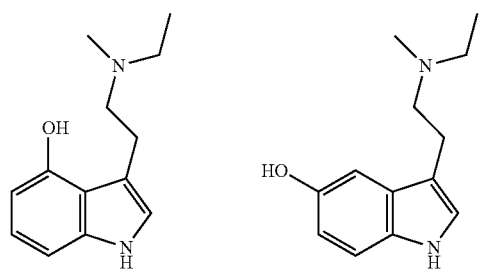
-continued
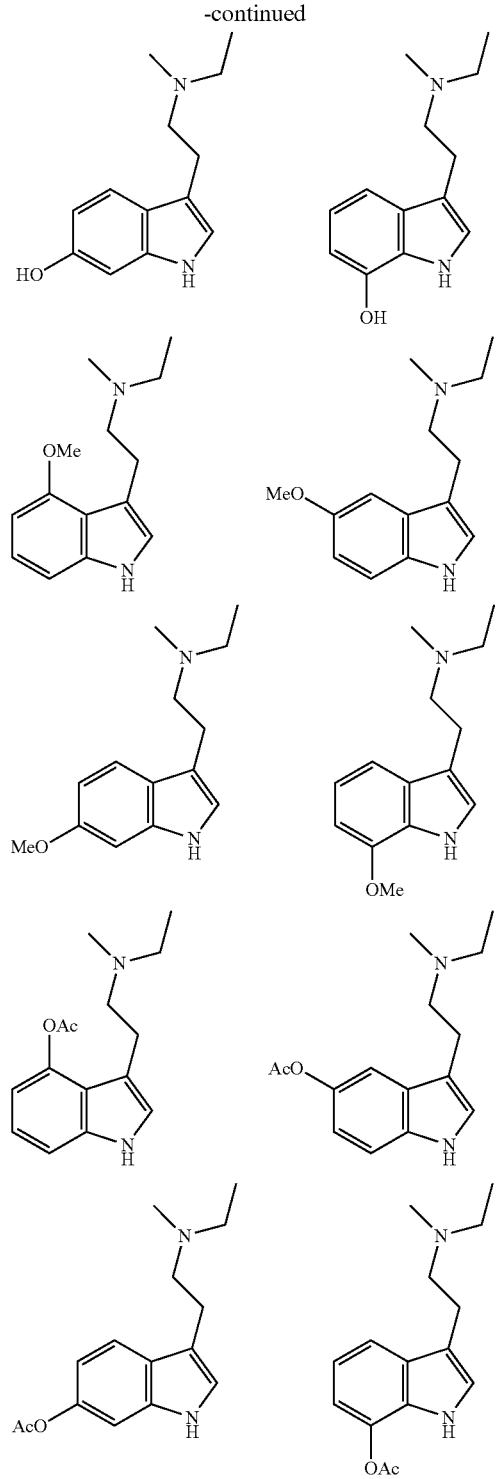
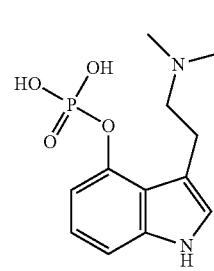

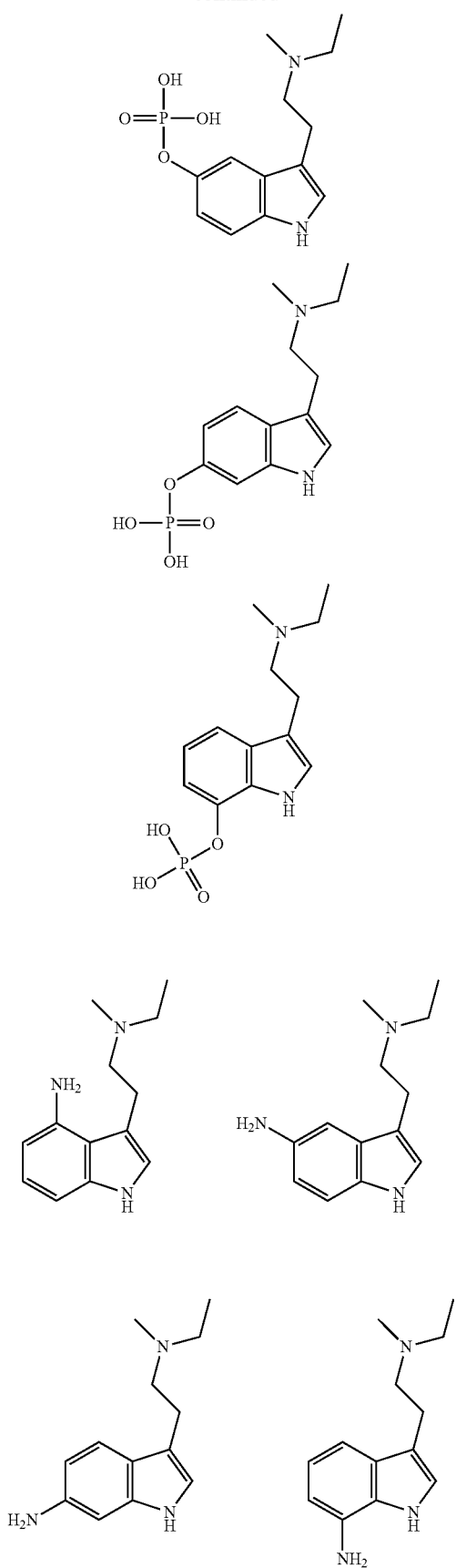
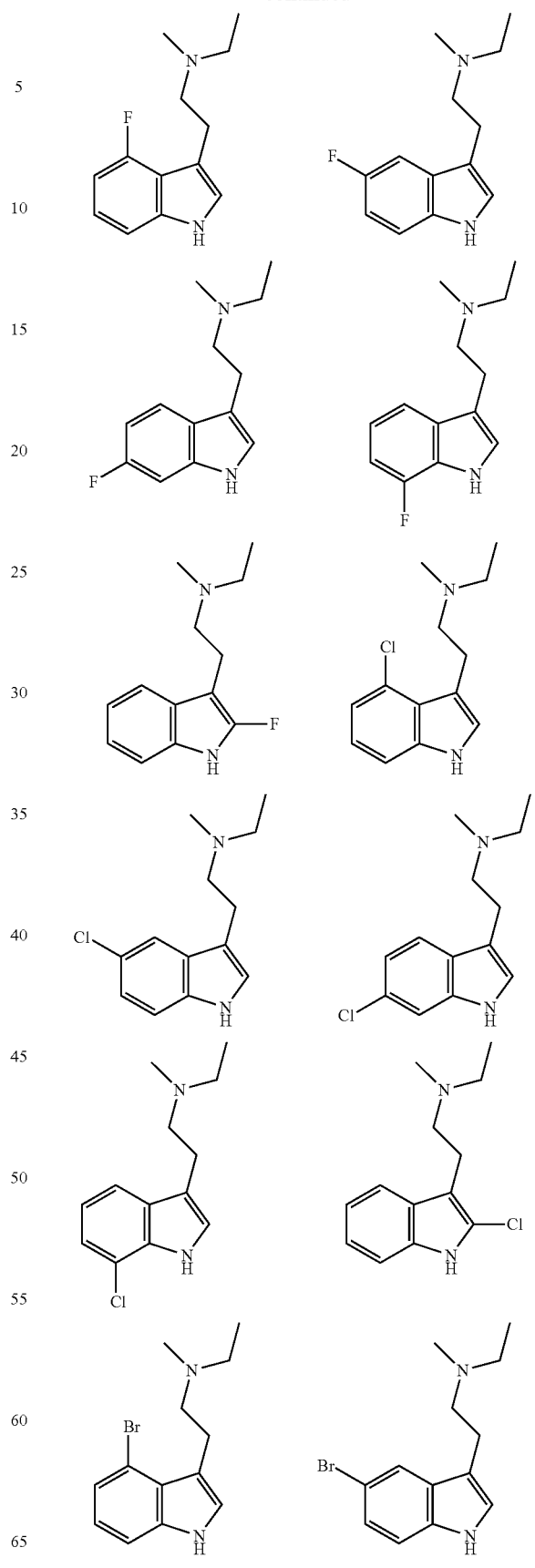

-continued
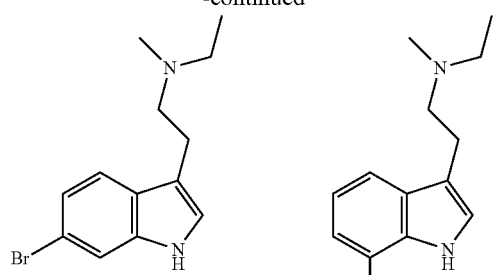
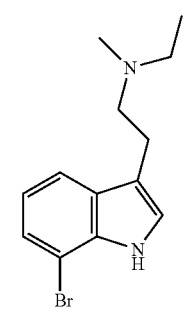
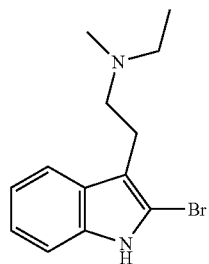
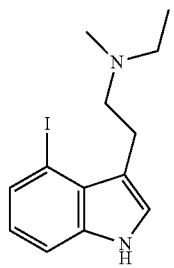
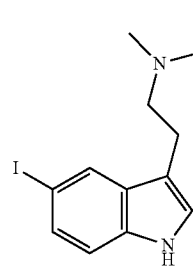
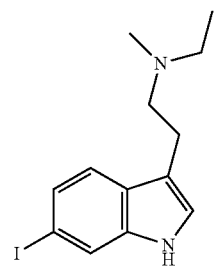
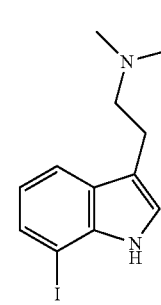
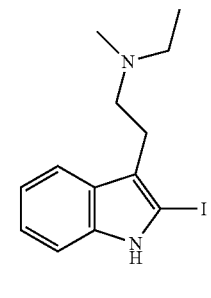
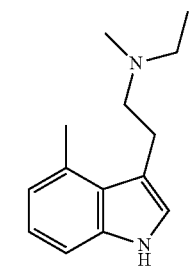
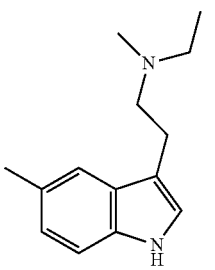
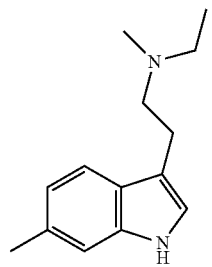
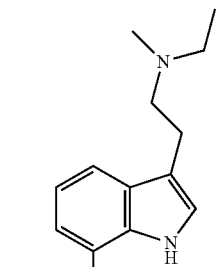
-continued
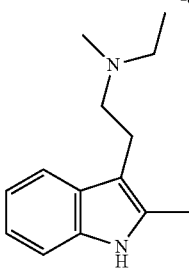
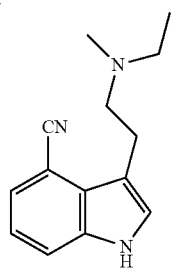
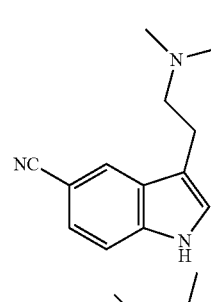
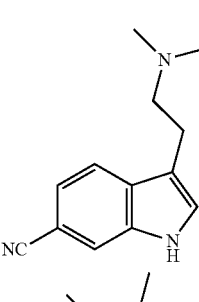
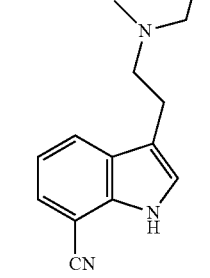
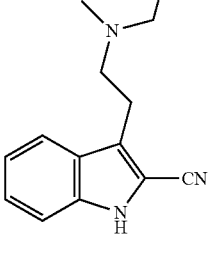
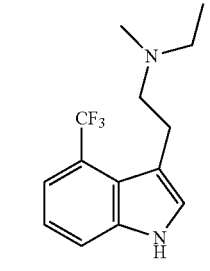
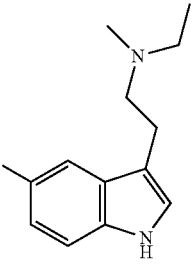
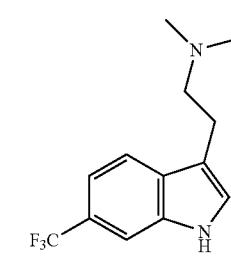
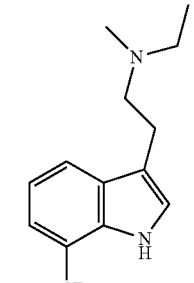
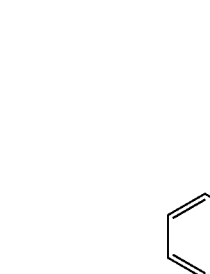
or a pharmaceutically acceptable salt thereof.

In other embodiments, provided herein are methods and compositions for treating migraine, cluster headache, or other headache disorders by administering to a patient in need thereof a compound of the present disclosure.

In other embodiments, provided herein are methods and compositions for treating inflammation by administering to a patient in need thereof a compound of the present disclosure.

In embodiments, methods include treating a mood disorder, e.g., a depressive disorder, by administering to a patient in need thereof a pharmaceutical composition including about 0.01 mg to about 400 mg of a compound disclosed herein. In embodiments, doses may be, e.g., in the range of about 0.01 to 400 mg, 0.01 to 300 mg, 0.01 to 250 mg, 0.01 to 200 mg, 0.01 to 150 mg, 0.01 to 100 mg, 0.01 to 75 mg, 0.01 to 50 mg, 0.01 to 25 mg, 0.01 to 20 mg, 0.01 to 15 mg, 0.01 to 10 mg, 0.01 to 5 mg, 0.01 to 1 mg, 0.01 to 0.5 mg, 0.01 to 0.1 mg, 0.1 to 300 mg, 0.1 to 250 mg, 0.1 to 200 mg, 0.1 to 150 mg, 0.1 to 100 mg, 0.1 to 75 mg, 0.1 to 50 mg, 0.1 to 25 mg, 0.1 to 20 mg, 0.1 to 15 mg, 0.1 to 10 mg, 0.1 to 5 mg, 0.1 to 1 mg, 10 to 300 mg, 10 to 250 mg, 10 to 200 mg, 10 to 150 mg, 10 to 100 mg, 10 to 50 mg, 10 to 25 mg, 10 to 15 mg, 20 to 300 mg, 20 to 250 mg, 20 to 200 mg, 20 to 150 mg, 20 to 100 mg, 20 to 50 mg, 50 to 300 mg, 50 to 250 mg, 50 to 200 mg, 50 to 150 mg, 50 to 100 mg, 100 to 300 mg, 100 to 250 mg, 100 to 200 mg, with doses of, e.g., about 0.25 mg, 0.5 mg, 0.75 mg, 1 mg, 1.25 mg, 1.5 mg, 1.75 mg, 2.0 mg, 2.5 mg, 3.0 mg, 3.5 mg, 4.0 mg, 4.5 mg, 5 mg, 10 mg, 15 mg, 20 mg, 25 mg, 30, mg, 35 mg, 40 mg, 45 mg, 50 mg, 75 mg, 100 mg, 125 mg, 150 mg, 175 mg, 200 mg, 225 mg, 250 mg, 275 mg, 300 mg, and 400 mg being examples.

In specific embodiments, dosages may include amounts of a compound disclosed herein in the range of about, e.g., 1 mg to 200 mg, 1 mg to 100 mg, 1 mg to 50 mg, 1 mg to 40 mg, 1 mg to 30 mg, 1 mg to 20 mg, 1 mg to 15 mg, 0.01 mg to 10 mg, 0.1 mg to 15 mg, 0.15 mg to 12.5 mg, or 0.2 mg to 10 mg, with doses of 0.1 mg, 0.2 mg, 0.3 mg, 0.4 mg, 0.5 mg, 0.6 mg, 0.7 mg, 0.8 mg, 0.9 mg, 1.0 mg, 1.5 mg, 1.75 mg, 2 mg, 2.5 mg, 2.75 mg, 3 mg, 3.5 mg, 3.75 mg, 4 mg, 4.5 mg, 4.75 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 15 mg, 20 mg, 25 mg, 30 mg, 35 mg, 40 mg, 45 mg, 50 mg, 60 mg, 75 mg, 80 mg, 90 mg, 100 mg, 125 mg, 150 mg, and 200 mg being specific examples of doses.

Typically, dosages of a compound disclosed herein are administered once, twice, three or four times daily, every other day, every three days, once weekly, twice monthly, once monthly, or 3-4 times yearly to a patient in need thereof. In embodiments, the dosage is about, e.g., 1-400 mg/day, or 1-300 mg/day, or 1-250 mg/day, or 1-200 mg/day, for example 300 mg/day, 250 mg/day, 200 mg/day, 150 mg/day, 100 mg/day, 75 mg/day, 50 mg/day, 40 mg/day, 30 mg/day, 25 mg/day, 20 mg/day, 15 mg/day, 10 mg/day, 5 mg/day, or 1 mg/day.

In embodiments, pharmaceutical compositions for parenteral administration or inhalation, e.g., a spray or mist, of a compound disclosed herein include a concentration of about 0.005 mg/ml to about 500 mg/mL. In embodiments, the compositions include a compound disclosed herein at a concentration of, e.g., about 0.05 mg/mL to about 50 mg/mL, about 0.05 mg/mL to about 100 mg/mL, about 0.005 mg/mL to about 500 mg/mL, about 0.1 mg/mL to about 50 mg/mL, about 0.1 mg/mL to about 10 mg/mL, about 0.05 mg/mL to about 25 mg/mL, about 0.05 mg/mL to about 10 mg/mL, about 0.05 mg/mL to about 5 mg/mL, or about 0.05 mg/mL to about 1 mg/mL.

In embodiments, the composition includes a compound disclosed herein at a concentration of, e.g., about 0.05 mg/mL to about 15 mg/mL, about 0.5 mg/mL to about 10 mg/mL, about 0.25 mg/mL to about 5 mg/mL, about 0.5 mg/mL to about 7 mg/mL, about 1 mg/mL to about 10 mg/mL, about 5 mg/mL to about 10 mg/mL, about 5 mg/mL to about 15 mg/mL, about 5 mg/mL to 25 mg/mL, about 5 mg/mL to 50 mg/mL, or about 10 mg/mL to 100 mg/mL. In embodiments, the pharmaceutical compositions are formulated as a total volume of about, e.g., 10 mL, 20 mL, 25 mL, 50 mL, 100 mL, 200 mL, 250 mL, or 500 mL.

Typically, dosages may be administered to a subject once, twice, three or four times daily, every other day, every three days, once weekly, twice monthly, once monthly, or 3-4 times yearly. In embodiments, a compound disclosed herein is administered to a subject once in the morning, or once in the evening. In embodiments, a compound disclosed herein is administered to a subject once in the morning, and once in the evening. In embodiments, a compound disclosed herein is administered to a subject three times a day (e.g., at breakfast, lunch, and dinner), at a dose, e.g., of 50 mg/administration (e.g., 150 mg/day).

In embodiments, a compound disclosed herein is administered to a subject 12.5 mg/day in one or more doses. In embodiments, a compound disclosed herein is administered to a subject 25 mg/day in one or more doses. In embodiments, a compound disclosed herein is administered to a subject 35 mg/day in one or more doses. In embodiments, a compound disclosed herein is administered to a subject 50 mg/day in one or more doses. In embodiments, a compound disclosed herein is administered to a subject 75 mg/day in one or more doses. In embodiments, a compound disclosed herein is administered to a subject 100 mg/day in one or more doses. In embodiments, a compound disclosed herein is administered to a subject 150 mg/day in one or more doses. In embodiments, a compound disclosed herein is administered to a subject 200 mg/day in one or more doses. In embodiments, a compound disclosed herein is administered to a subject 250 mg/day in one or more doses.

In embodiments, the dosage of a compound disclosed herein is 0.0005-5 mg/kg, 0.001-1 mg/kg, 0.01-1 mg/kg or 0.1-5 mg/kg once, twice, three times or four times daily. For example, in embodiments, the dosage is 0.0005 mg/kg, 0.001 mg/kg, 0.005 mg/kg, 0.01 mg/kg, 0.025 mg/kg, 0.05 mg/kg, 0.1 mg/kg, 0.15 mg/kg, 0.2 mg/kg, 0.25 mg/kg, 0.3 mg/kg, 0.4 mg/kg, 0.5 mg/kg, 0.75 mg/kg, 1 mg/kg, 2.5 mg/kg, or 5 mg/kg, once, twice, three or four times daily. In embodiments, a subject is administered a total daily dose of 0.01 mg to 500 mg of a compound disclosed herein once, twice, three times, or four times daily. In embodiments, the total amount administered to a subject in a 24-hour period is, e.g., 0.01 mg, 0.025 mg, 0.05 mg, 0.075 mg, 0.1 mg, 0.125 mg, 0.15 mg, 0.175 mg, 0.2 mg, 0.25 mg, 0.3 mg, 0.4 mg, 0.5 mg, 0.75 mg, 1 mg, 1.5 mg, 2 mg, 2.5 mg, 3 mg, 4 mg, 5 mg, 7.5 mg, 10 mg, 12.5 mg, 15 mg, 17.5 mg, 20 mg, 25 mg, 30 mg, 35 mg, 40 mg, 45 mg, 50 mg, 60 mg, 75 mg, 80 mg, 90 mg, 100 mg, 125 mg, 150 mg, 175 mg, 200 mg, 250 mg, 300 mg, 400 mg, or 500 mg. In embodiments, the subject may be started at a low dose and the dosage is escalated. In embodiments, the subject may be started at a high dose and the dosage is decreased.

In embodiments, a compound disclosed herein may be administered, e.g., via inhalation or orally, at specified intervals. For example, during treatment a patient may be administered a compound disclosed herein at intervals of every, e.g., 1 year, 6 months, 90 days, 60 days, 30 days, 14 days, 7 days, 3 days, 24 hours, 12 hours, 8 hours, 6 hours, 5 hours, 4 hours, 3 hours, 2.5 hours, 2.25 hours, 2 hours, 1.75 hours, 1.5 hours, 1.25 hours, 1 hour, 0.75 hour, 0.5 hour, or 0.25 hour.

In embodiments, a compound of the present disclosure or a pharmaceutically acceptable salt thereof is administered to a patient under the supervision of a healthcare provider.

In embodiments, a compound of the present disclosure or a pharmaceutically acceptable salt thereof is administered to a patient under the supervision of a healthcare provider at a clinic specializing in the delivery of psychoactive treatments.

In embodiments, a compound of the present disclosure is administered to a patient under the supervision of a healthcare provider at a high dose intended to induce a psychedelic experience in the subject, e.g., 12.5 mg, 15 mg, 17.5 mg, 20 mg, 25 mg, 30 mg, 35 mg, 40 mg, 45 mg, 50 mg, 60 mg, 70 mg, 80 mg, 90 mg, 100 mg, 125 mg, or 150 mg.

In some embodiments, the administration to a patient of a high dose under the supervision of a healthcare provider occurs periodically in order to maintain a therapeutic effect in the patient, e.g., every three days, twice weekly, once weekly, twice monthly, once monthly, thrice yearly, twice yearly, or once yearly.

In some embodiments, a compound of the present disclosure or a pharmaceutically acceptable salt thereof is administered by a patient on their own at home or otherwise away from the supervision of a healthcare provider.

In some embodiments, a compound of the present disclosure or a pharmaceutically acceptable salt thereof is administered by a patient on their own at home or otherwise away from the supervision of a healthcare provider at a low dose intended to be sub-perceptual or to induce threshold psychoactive effects, e.g., 0.1 mg, 0.25 mg, 0.5 mg, 0.75 mg, 1 mg, 1.5 mg, 2 mg, 2.5 mg, 3 mg, 4 mg, 5 mg, 7.5 mg, or 10 mg.

In some embodiments, the administration by a patient of a low dose on their own occurs periodically in order to maintain a therapeutic effect in the patient, e.g., daily, every other day, every three days, twice weekly, once weekly, twice monthly, or once monthly.

Suitable dosage forms for a compound disclosed herein include, but are not limited to, oral forms, such as tablets, hard or soft gelatin capsules, powders, granules and oral solutions, syrups or suspensions, troches, as well as sublingual, buccal, intratracheal, intraocular, or intranasal forms, forms adapted to inhalation, topical forms, transdermal forms, or parenteral forms, for example, forms adapted for intravenous, intra-arterial, intraperitoneal, intrathecal, intraventricular, intramuscular or subcutaneous administration. In embodiments, for such parenteral administration, it may be in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Pharmaceutical compositions herein may be provided with immediate release, delayed release, extended release, or modified release profiles. In embodiments, pharmaceutical compositions with different drug release profiles may be combined to create a two-phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, glidants, disintegrants, fillers, and coating compositions.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant. The compositions may be prepared by any method well known in the art of pharmacy.

Such methods include the step of bringing in association compounds used in the disclosure or combinations thereof with any auxiliary agent. The auxiliary agent(s), also named accessory ingredient(s), include those conventional in the art, such as carriers, fillers, binders, diluents, disintegrants, lubricants, colorants, flavoring agents, anti-oxidants, and wetting agents. Such auxiliary agents are suitably selected with respect to the intended form and route of administration and as consistent with conventional pharmaceutical practices.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

Tablets may contain the active ingredient compounds and suitable binders, lubricants, disintegrating agents, coloring agents, flavoring agents, flow-inducing agents, and melting agents. Gelatin capsules may contain the active ingredient compounds and powdered carriers, such as lactose, starch, cellulose derivatives, magnesium stearate, stearic acid, and the like. Similar diluents can be used to make compressed tablets. Compressed tablets can be sugar coated or film coated to mask any unpleasant taste and protect the tablet from the atmosphere, or enteric coated for selective disintegration in the gastrointestinal tract. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

For oral administration in liquid dosage form, the oral drug components are combined with any oral, non-toxic, pharmaceutically acceptable inert carrier such as ethanol, glycerol, water, and the like. Examples of suitable liquid dosage forms include, but are not limited to, solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Liquid dosage forms for oral administration can contain coloring and flavoring to increase patient acceptance.

For parenteral administration, suitable compositions include aqueous and non-aqueous sterile solutions. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. The compositions may be presented in unit-dose or multi-dose containers, for example sealed vials and ampoules, and may be stored in a freeze-dried (lyophilized) condition requiring only the addition of sterile liquid carrier, for example water, prior to use. For transdermal administration, e.g. gels, patches or sprays can be contemplated. Compositions or formulations suitable for pulmonary administration e.g. by nasal inhalation, include fine dusts or mists which may be generated by means of metered dose pressurized aerosols, nebulizers or insufflators. Parenteral and intravenous forms may also include minerals and other materials to make them compatible with the type of injection or delivery system chosen.

The compounds used in the method of the present disclosure may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present disclosure may also be coupled to soluble polymers as targetable drug carriers or as prodrugs. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Pharmaceutical compositions herein may be provided with immediate release, delayed release, extended release, or modified release profiles. In some embodiments, pharmaceutical compositions with different drug release profiles may be combined to create a two-phase or three-phase release profile. For example, pharmaceutical compositions may be provided with an immediate release and an extended-release profile. In some embodiments, pharmaceutical compositions may be provided with an extended release and delayed release profile. Such composition may be provided as pulsatile formulations, multilayer tablets, or capsules containing tablets, beads, granules, etc.

Pharmaceutical compositions herein may be provided with abuse deterrent features by techniques know in the art, for example, by making a tablet that is difficult to crush or to dissolve in water.

The disclosure further includes a pharmaceutical composition, as hereinbefore described, in combination with packaging material, including instructions for the use of the composition for a use as hereinbefore described.

The exact dose and regimen of administration of the composition will necessarily be dependent upon the type and magnitude of the therapeutic or nutritional effect to be achieved and may vary depending on factors such as the particular compound, formula, route of administration, or age and condition of the individual subject to whom the composition is to be administered.

The compounds used in the method of the present disclosure may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

In some embodiments, compounds disclosed herein may be administered in combination with one or more other antidepressant treatments, such as, tricyclic antidepressants, MAOIs, SSRIs, and double and triple uptake inhibitors and/or anxiolytic drugs for manufacturing a medicament for treating depression, anxiety, and/or other related diseases, including to provide relief from depression or anxiety and preventing recurrence of depression or anxiety. In some embodiments, therapeutics that may be used in combination with a compound of the present disclosure include, but are not limited to, Anafranil, Adapin, Aventyl, Elavil, Norpramin, Pamelor, Pertofrane, Sinequan, Surmontil, Tofranil, Vivactil, Parnate, Nardil, Marplan, Celexa, Lexapro, Luvox, Paxil, Prozac, Zoloft, Wellbutrin, Effexor, Remeron, Cymbalta, Desyrel (trazodone), and Ludiomill.

Definitions

In the context of the present disclosure the term "5-HT2a receptor agonist" is intended to mean any compound or substance that activates the 5-HT2a receptor. The agonist may be a partial or full agonist.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "alkyl" refers to a straight or branched alkyl group. Exemplary alkyl groups are methyl, ethyl, propyl, isopropyl, butyl, isobutyl, and tert-butyl.

The term "haloalkyl" refers to a straight or branched alkyl group that is substituted with one or more halogen atoms.

The term "halogen" means F, Cl, Br, or I.

As used herein, the term "pharmaceutically acceptable" refers to molecular entities and compositions that are "generally regarded as safe", e.g., that are physiologically tolerable and do not typically produce an allergic or similar untoward reaction when administered to a human. In embodiments, this term refers to molecular entities and compositions approved by a regulatory agency of the federal or a state government, as the GRAS list under sections 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH (OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$ N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N (R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O) (CH$_2$)$_{0-4}$SR°, SC(S)SR°; —(CH$_2$)$_{0-4}$SC(O)R°; —(CH$_2$)$_{0-4}$C (O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$ S(O)$_2$R°; —(CH$_2$)$_{0-4}$S(O)$_2$OR°; —(CH$_2$)$_{0-4}$OS (O)$_2$R°; —S(O)$_2$NR°$_2$; —(CH$_2$)$_{0-4}$S(O)R°; —N(R°) S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{0-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR°$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O) R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently CM aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salts" includes both acid and base addition salts, wherein the compound is modified by making acid or base salts thereof. Examples of pharmaceutically acceptable salts include but are not limited to mineral or organic acid salts of basic residues such as amines, and alkali or organic salts of acidic residues such as carboxylic acids. Pharmaceutically acceptable salts include conventional non-toxic salts or quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, and nitric acids; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, naphthalenesulfonic, methanesulfonic, ethane disulfonic, and oxalic acids. The pharmaceutically acceptable salts of a compound disclosed herein can be synthesized from the parent compound, which contains a basic or acidic moiety, by conventional chemical methods.

The terms "about" or "approximately" as used herein mean within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, a range up to 10%, a range up to 5%, and/or a range up to 1% of a given value. Alternatively, particularly with respect to biological systems or processes, the term can mean within an order of magnitude, e.g., within 5-fold, or within 2-fold, of a value. "About" and "approximately" are used interchangeably herein.

In embodiments, the terms "effective amount" or "therapeutically effective amount" refer to an amount of a compound, material, composition, medicament, or other material that is effective to achieve a particular pharmacological and/or physiologic effect including but not limited to reducing the frequency or severity of sadness or lethargy, depressed mood, anxious or sad feelings, diminished interest in all or nearly all activities, significant increased or decreased appetite leading to weight gain or weight loss, insomnia, irritability, fatigue, feelings of worthlessness, feelings of helplessness, inability to concentrate, and recurrent thoughts of death or suicide, or to provide a desired pharmacologic and/or physiologic effect, for example, reducing, inhibiting, or reversing one or more of the underlying pathophysiological mechanisms underlying the neurological dysfunction, modulating dopamine levels or signaling, modulating serotonin levels or signaling, modulating norepinephrine levels or signaling, modulating glutamate or GABA levels or signaling, modulating synaptic connectivity or neurogenesis in certain brain regions, or a combination thereof. The precise dosage will vary according to a variety of factors such as subject-dependent variables (e.g., age, immune system health, clinical symptoms etc.), the disease or disorder being treated, as well as the route of administration and the pharmacokinetics of the agent being administered.

In embodiments, deuterium-enriched compounds disclosed herein and their use are contemplated and within the scope of the methods and compositions described herein. Deuterium can be incorporated in any position in place of hydrogen (protium) synthetically, according to synthetic procedures known in the art. For example, deuterium may be incorporated to various positions having an exchangeable proton, such as an amine N—H, via proton-deuterium equilibrium exchange. Thus, deuterium may be incorporated selectively or non-selectively through methods known in the art.

In some embodiments, the level of deuterium at each deuterium-enriched —H site of the compound is 0.02% to 100%.

In some embodiments, the level of deuterium at each deuterium-enriched —H site of the compound is 50%-100%, 70%-100%, 90%-100%, 95%-100%, 96%-100%, 97%-100%, 98%-100%, or 99%-100%.

Exemplary deuterium-enriched compounds disclosed herein include:

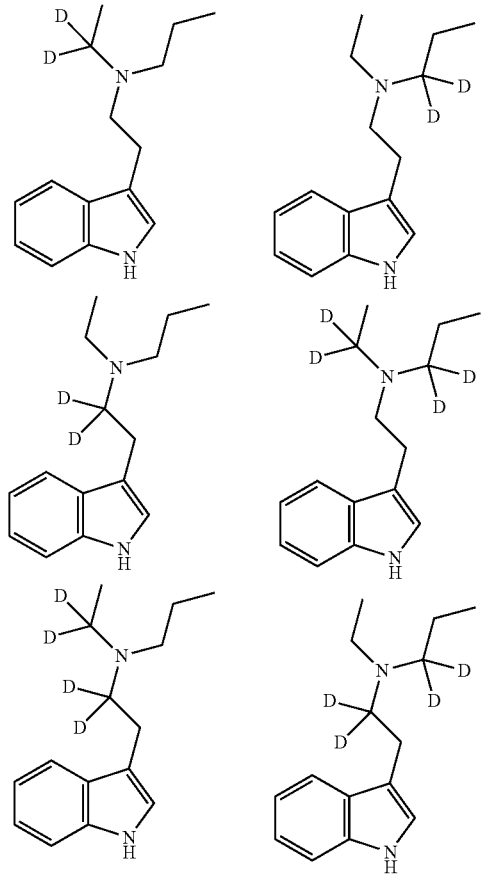

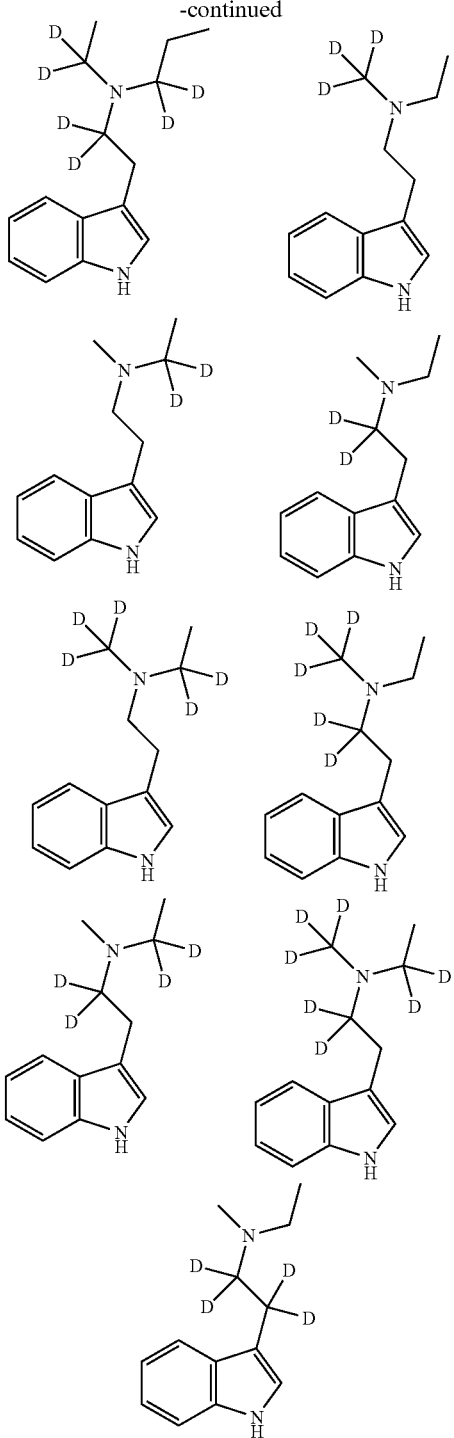

The compounds disclosed herein may be racemic and/or optically active isomers thereof. In this regard, some of the compounds can have asymmetric carbon atoms, and therefore, can exist either as racemic mixtures or as individual optical isomers (enantiomers). Compounds described herein that contain a chiral center include all possible stereoisomers of the compound, including compositions including the racemic mixture of the two enantiomers, as well as compositions including each enantiomer individually, substantially free of the other enantiomer. Thus, for example, contemplated herein is a composition including the S enantiomer of a compound substantially free of the R enantiomer, or the R enantiomer substantially free of the S enantiomer. If the named compound includes more than one chiral center, the scope of the present disclosure also includes compositions including mixtures of varying proportions between the diastereomers, as well as compositions including one or more diastereomers substantially free of one or more of the other diastereomers. By "substantially free" it is meant that the composition includes less than 25%, 15%, 10%, 8%, 5%, 3%, or less than 1% of the minor enantiomer or diastereomer (s). Enumerated Embodiments

EXEMPLIFICATION

Methods for synthesizing, isolating, preparing, and administering various stereoisomers are known in the art. Separation of diastereomers or cis and trans isomers may be achieved by conventional techniques, such as, for example, by fractional crystallization, chromatography or High-Performance Liquid Chromatography (HPLC) of a stereoisomeric mixture of the agent or a suitable salt or derivative thereof. An individual enantiomer of a compound disclosed herein may also be prepared from a corresponding optically pure intermediate or by resolution, such as by HPLC of the corresponding racemate using a suitable chiral support or by fractional crystallization of the diastereomeric salts formed by reaction of the corresponding racemate with a suitable optically active acid or base, as appropriate.

The compounds used in the method of the present disclosure may be prepared by techniques well known in organic synthesis and familiar to a practitioner ordinarily skilled in the art. For example, the compounds may be prepared by the synthetic transformations shown below under general procedures and further described in the specific examples that follow.

Abbreviations

ACN: Acetonitrile

DCM: Dichloromethane

DIPEA: Diisopropylethylamine

DMAc: Dimethylacetamide

DMSO: Dimethylsulfoxide

DMT: N,N-dimethyltryptamine

HLM: human liver micro somes

HPLC: High-performance liquid chromatography

LCMS: Liquid Chromatography-mass spectrometry

MAO: monoamine oxidase

5-MeO-DMT: 5-methoxy-N,N-dimethyltryptamine

MLM: mouse liver microsomes

NADPH: Nicotinamide adenine dinucleotide phosphate hydride

NMR: Nuclear magnetic resonance

PBS: phosphate buffered saline

Pd/C: Palladium on carbon

RLM: rat liver microsomes

R.T.: Room temperature/ambient temperature

THF: Tetrahydrofuran

General Procedures

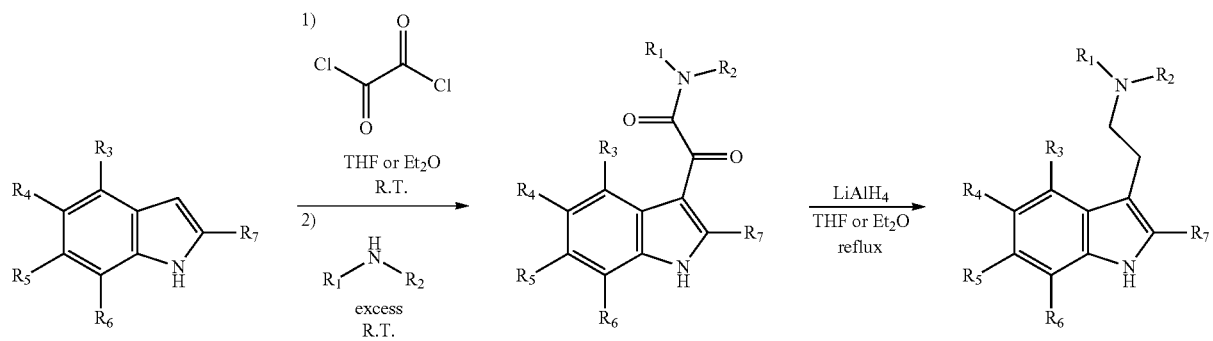
R₁, R₂ = Me, Et, nPr, iPr, cyclopropyl, allyl, isobutyl, cycloproylmethyl
R₃ - R₇ = H, F, Cl, Br, I, CF₃, Me
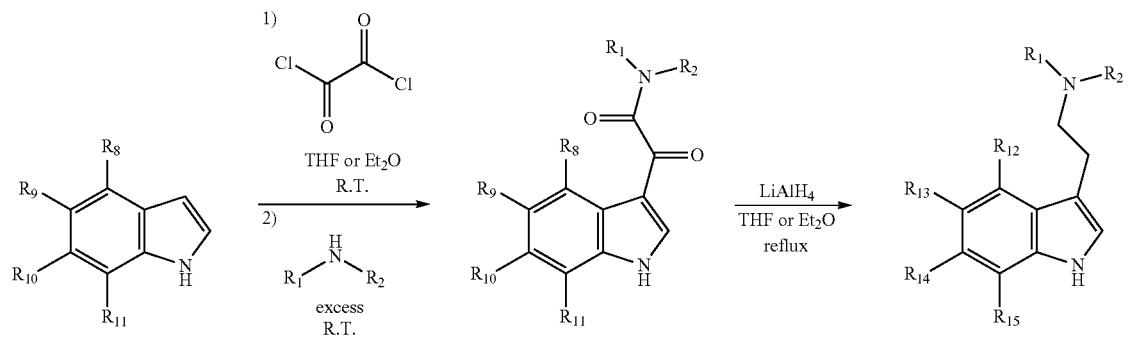
R₁, R₂ = Me, Et, nPr, iPr, cyclopropyl, allyl, isobutyl, cyclopropylmethyl
R₈ - R₁₁ = H, OAc, OMe
R₁₂ - R₁₅ = H, OH, OMe
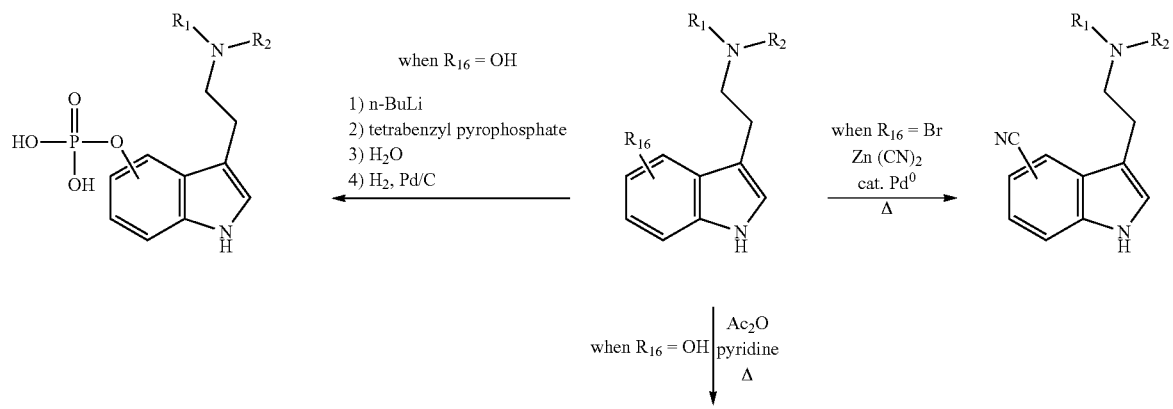
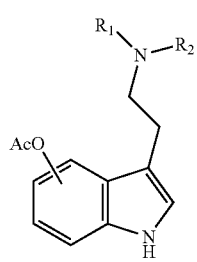
R₁, R₂ = Me, Et, nPr, iPr, cyclopropyl, allyl, isobutyl, cyclopropylmethyl

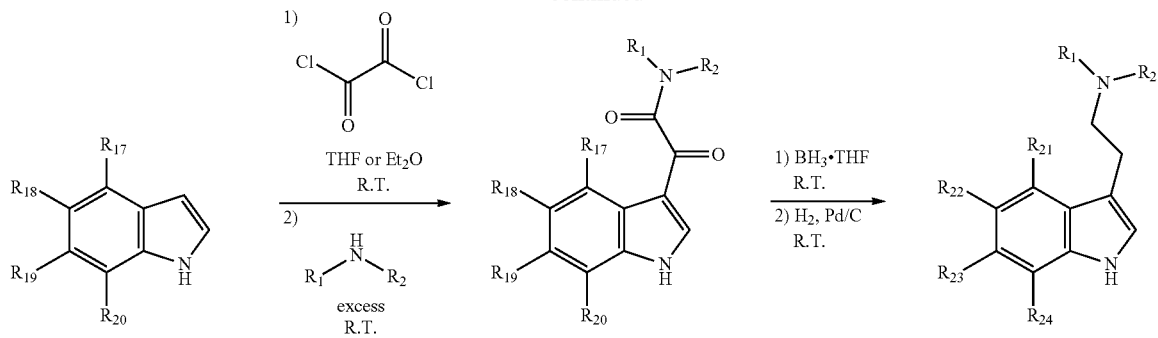

R$_1$, R$_2$ = Me, Et, nPr, iPr, cyclopropyl, allyl, isobutyl, cycloproylmethyl
R$_{17}$ - R$_{20}$ = NO$_2$
R$_{21}$ - R$_{24}$ = NH$_2$

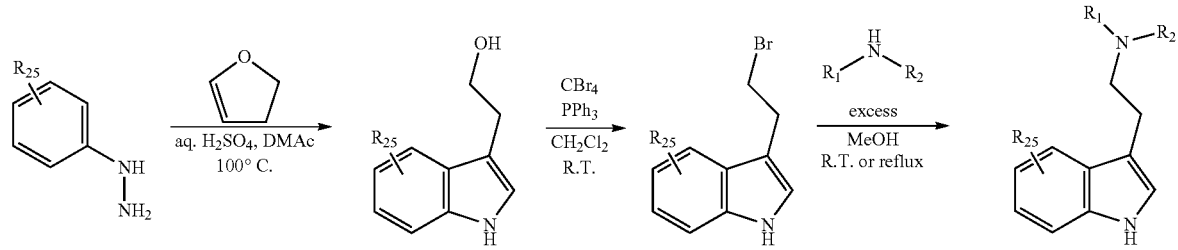

R$_1$, R$_2$ = Me, Et, nPr, iPr, cyclopropyl, allyl, isobutyl, cyclopropylmethyl
R$_{25}$ = H, F, Cl, Br, I, CF$_3$, Me, CN, OMe, OH, OAc, NH$_2$ However, these may not be the only means by which to synthesize or obtain the desired compounds.

The present disclosure provides a pharmaceutical composition comprising the compound of the present disclosure and a pharmaceutically acceptable carrier.

The subject disclosure is also intended to include all isotopes of atoms occurring in the compounds disclosed herein. Isotopes include those atoms having the same atomic number but different mass numbers. By way of general example and without limitation, isotopes of hydrogen include tritium and deuterium. Isotopes of carbon include $^{13}$C and $^{14}$C.

It will be noted that any notation of a carbon in structures throughout this application, when used without further notation, is intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, is intended to represent all isotopes of hydrogen, such as $^{1}$H, $^{2}$H, or $^{3}$H. Furthermore, any compounds containing $^{2}$H or $^{3}$H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

It should be understood that the examples and embodiments provided herein are exemplary. Those skilled in the art will envision various modifications of the examples and embodiments that are consistent with the scope of the disclosure herein. Such modifications are intended to be encompassed by the claims.

EXAMPLES

Example 1. Preparation of Compound 3

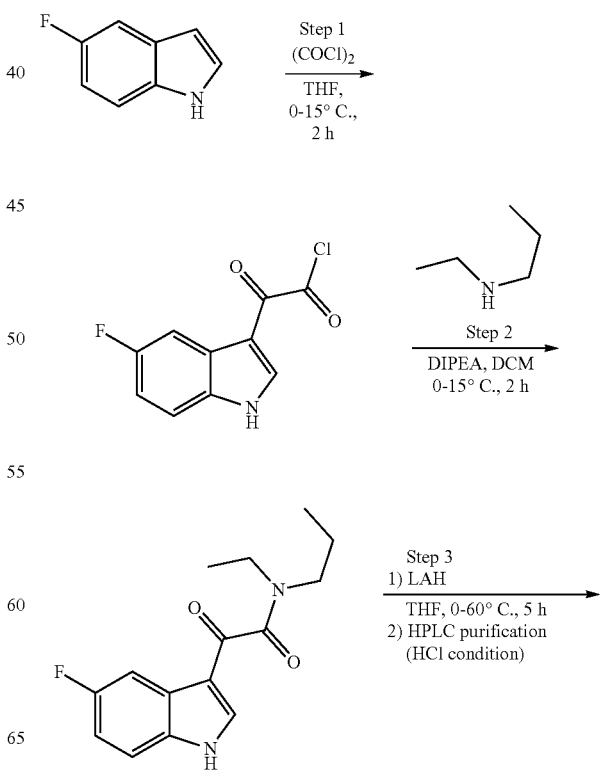

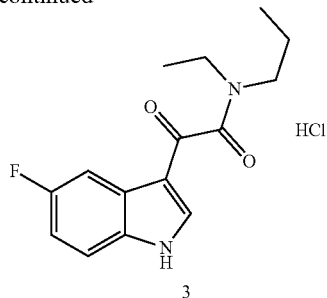

Step 1: Preparation of 2-(5-fluoro-1H-indol-3-yl)-2-oxoacetyl chloride.

To a mixture of 5-fluoro-1H-indole (3 g, 22.20 mmol, 1 eq) in THF (30 mL) was added oxalyl chloride (4.23 g, 33.30 mmol, 2.91 mL, 1.5 eq) in one portion at 0° C. under $N_2$. The mixture was stirred at 15° C. for 2 hours. On completion, the reaction mixture was concentrated to obtain 2-(5-fluoro-1H-indol-3-yl)-2-oxoacetyl chloride as a yellow solid (5.01 g, 22.21 mmol, 100% yield).

Step 2: Preparation of N-ethyl-2-(5-fluoro-1H-indol-3-yl)-2-oxo-N-propylacetamide.

To a solution of N-ethylpropan-1-amine (2.90 g, 33.32 mmol, 4.63 mL, 1.5 eq) in DCM (20 mL) was added N,N-diisopropylethylamine (5.74 g, 44.42 mmol, 7.74 mL, 2 eq). Then 2-(5-fluoro-1H-indol-3-yl)-2-oxoacetyl chloride (5.01 g, 22.21 mmol, 1 eq) in THF (30 mL) was added at 0° C. Then the mixture was stirred at 15° C. for 2 hours. On completion, aq. $NH_4Cl$ (30 mL) was added and the mixture was stirred for 5 min. The aqueous phase was extracted with DCM (50 mL×3). The combined organic phase was dried with anhydrous $Na_2SO_4$, filtered, and concentrated in vacuo. The residue was purified by column chromatography ($SiO_2$, petroleum ether/ethyl acetate=5/1 to 0/1) to obtain N-ethyl-2-(5-fluoro-1H-indol-3-yl)-2-oxo-N-propylacetamide as a white solid (5.28 g, 19.11 mmol, 86% yield). $^1$H NMR (400 MHz, $CDCl_3$) (partial integrals due to conformers) δ 10.80 (br s, 1H), 7.94 (dd, J=2.0, 9.3 Hz, 1H), 7.53 (d, J=3.2 Hz, 1H), 7.17 (ddd, J=1.2, 4.3, 8.9 Hz, 1H), 6.93 (dt, J=2.4, 9.0 Hz, 1H), 3.58-3.49 (m, 1H), 3.48-3.39 (m, 1H), 3.35 (q, J=7.2 Hz, 1H), 3.29-3.20 (m, 1H), 1.76-1.53 (m, 2H), 1.25 (t, J=7.2 Hz, 1.5H), 1.17 (t, J=7.2 Hz, 1.5H), 1.00 (t, J=7.6 Hz, 1.5H), 0.80 (t, J=7.2 Hz, 1.5H).

Step 3: Preparation of N-ethyl-N-(2-(5-fluoro-1H-indol-3-yl)ethyl)propan-1-amine hydrochloride (3)

To a solution of N-ethyl-2-(5-fluoro-1H-indol-3-yl)-2-oxo-N-propylacetamide (2 g, 7.24 mmol, 1 eq) in THF (30 mL) was added lithium aluminum hydride (824.18 mg, 21.72 mmol, 3 eq) at 0° C. The mixture was then stirred at 60° C. for 5 hours. On completion, the mixture was cooled to 0° C. Water (0.83 mL) was added and the reaction mixture was stirred for 5 min. Then 30% aq. NaOH (0.83 mL) was added and the mixture was stirred until the solids were white and free flowing. The mixture was filtered and the filtrate was concentrated in vacuo. The residue was purified by prep-HPLC (column=Phenomenex luna C18 (250*70 mm, 15 µm); mobile phase=water (0.05% HCl)-ACN, B %=10%-34%; $R_T$=22 min) to afford N-ethyl-N-[2-(5-fluoro-1H-indol-3-yl)ethyl]propan-1-amine hydrochloride (3) as a white solid (845.6 mg, 2.97 mmol, 41% yield). $^1$H NMR (400 MHz, DMSO-d6) δ 11.13 (br s, 1H), 10.53 (br s, 1H), 7.48-7.30 (m, 3H), 6.94 (dt, J=2.4, 9.2 Hz, 1H), 3.33-2.94 (m, 8H), 1.85-1.57 (m, 2H), 1.26 (t, J=7.2 Hz, 3H), 0.93 (t, J=7.2 Hz, 3H); $^{13}$C NMR (101 MHz, DMSO-d6) (extra peaks due to C-F coupling) δ 158.40, 156.10, 133.35, 127.51, 127.41, 126.00, 113.04, 112.94, 110.07, 110.03, 109.96, 109.70, 103.69, 103.46, 52.87, 52.06, 46.94, 19.87, 17.01, 11.45, 8.86; LCMS($R_T$=1.709 min, MS calc.: 248.17, [M+H]+=249.1).

Example 2. Preparation of Compound 4

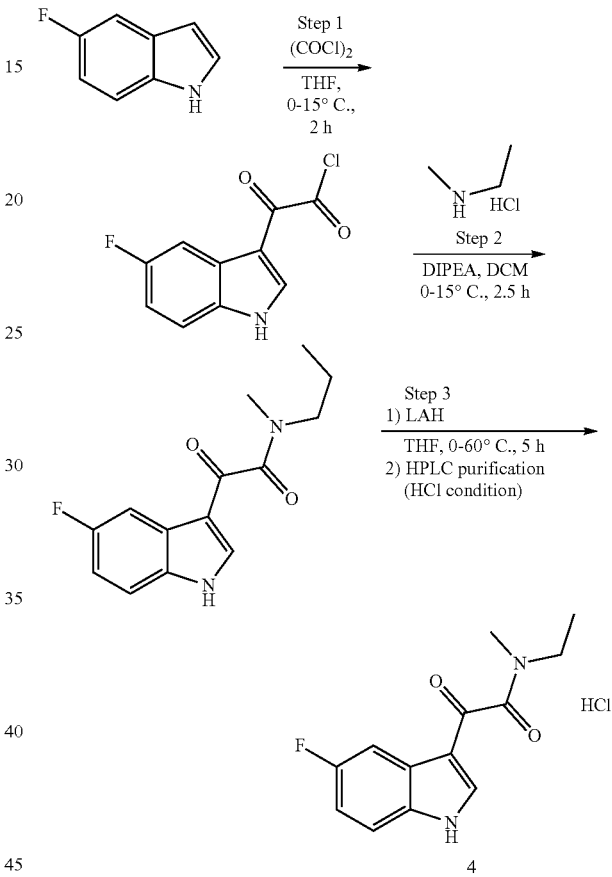

Step 1: Preparation of 2-(5-fluoro-1H-indol-3-yl)-2-oxoacetyl chloride

To a mixture of 5-fluoro-1H-indole (3 g, 22.20 mmol, 1 eq) in THF (30 mL) was added oxalyl chloride (4.23 g, 33.30 mmol, 2.91 mL, 1.5 eq) in one portion at 0° C. under $N_2$. The mixture was stirred at 15° C. for 2 hours. On completion, the reaction mixture was concentrated to obtain 2-(5-fluoro-1H-indol-3-yl)-2-oxoacetyl chloride as a yellow solid (5.01 g, 22.21 mmol, 100% yield).

Step 2: Preparation of N-ethyl-2-(5-fluoro-M-indol-3-yl)-N-methyl-2-oxoacetamide To a solution of N-methylethanamine hydrochloride (3.18 g, 33.31 mmol, 1.5 eq) in DCM (20 mL) was added N,N-diisopropylethylamine (11.48 g, 88.83 mmol, 15.47 mL, 4 eq). The mixture was stirred at 15° C. for 30 min. Then 2-(5-fluoro-1H-indol-3-yl)-2-oxoacetyl chloride (5.01 g, 22.21 mmol, 1 eq) in THF (30 mL) was added at 0° C. Then the mixture was stirred at 15° C. for 2.5 hours. On completion, aq. NH₄Cl (50 mL) was added and the mixture was stirred for 5 min. The aqueous phase was extracted with DCM (50 mL×3). The combined organic phase was dried with anhydrous Na₂SO₄, filtered, and concentrated in vacuo. The residue was purified by column chromatography (SiO₂, petroleum ether/ethyl acetate=15/1 to 0/1) to obtain N-ethyl-2-(5-fluoro-1H-indol-3-yl)-N-methyl-2-oxoacetamide as a white solid (4.30 g, 17.32 mmol, 78% yield). ¹H NMR (400 MHz, CDCl₃) (partial integrals due to conformers) δ 10.83-10.66 (m, 1H), 7.94 (dd, J=1.6, 9.2 Hz, 1H), 7.64-7.53 (m, 1H), 7.18 (dd, J=4.4, 8.9 Hz, 1H), 6.94 (dt, J=2.8, 9.0 Hz, 1H), 3.56 (q, J=7.2 Hz, 0.8H), 3.36 (q, J=7.2 Hz, 1.2H), 3.05 (s, 1.8H), 3.01 (s, 1.2H), 1.24 (t, J=7.2 Hz, 1.2H), 1.19 (t, J=7.2 Hz, 1.8H).

Step 3: Preparation of N-ethyl-2-(5-fluoro-M-indol-3-yl)-N-methylethan-1-amine hydrochloride (4)

To a solution of N-ethyl-2-(5-fluoro-1H-indol-3-yl)-N-methyl-2-oxoacetamide (1.73 g, 6.97 mmol, 1 eq) in THF (30 mL) was added lithium aluminum hydride (795.46 mg, 20.96 mmol, 3 eq) at 0° C. The mixture was then stirred at 60° C. for 5 hours. On completion, the mixture was cooled to 0° C. Water (0.8 mL) was added and the mixture was stirred for 5 min. Then 30% aq. NaOH (0.8 mL) was added and the mixture was stirred until the solids were white and free flowing. The mixture was filtered and the filtrate was concentrated in vacuo. The residue was purified by prep-HPLC (column=Phenomenex luna C18 (250*70 mm, 15 μm); mobile phase=water (0.04% HCl)-ACN, B %=10%-30%; R$_T$=20 min) to afford N-ethyl-2-(5-fluoro-1H-indol-3-yl)-N-methylethan-1-amine hydrochloride (4) as a white solid (670 mg, 2.61 mmol, 37% yield). ¹H NMR (400 MHz, DMSO-d6) δ 11.11 (br s, 1H), 10.46 (br s, 1H), 7.48-7.30 (m, 3H), 6.93 (dt, J=2.4, 9.2 Hz, 1H), 3.36-3.00 (m, 6H), 2.79 (d, J=5.2 Hz, 3H), 1.25 (t, J=7.2 Hz, 3H); ¹³C NMR (101 MHz, DMSO-d6) (extra peaks due to C-F coupling) δ 158.39, 156.09, 133.38, 127.49, 127.39, 125.96, 113.04, 112.94, 109.98, 109.94, 109.72, 103.74, 103.51, 54.87, 50.38, 38.60, 20.20, 9.32; LCMS (R$_T$=1.581 min, MS calc.: 220.14, [M+H]+=221.1).

Example 3. Preparation of Compound 5

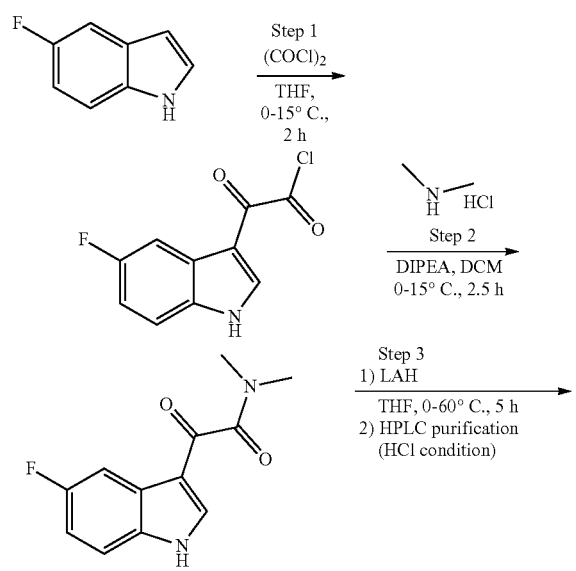

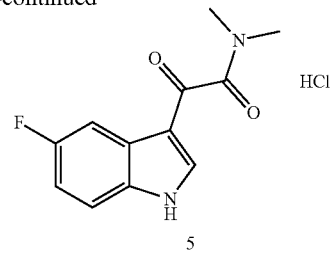

Step 1: Preparation of 2-(5-fluoro-1H-indol-3-yl)-2-oxoacetyl chloride

To a solution of 5-fluoro-1H-indole (5 g, 37.00 mmol, 1 eq) in THF (50 mL) was added oxalyl chloride (7.04 g, 55.50 mmol, 4.86 mL, 1.5 eq) at 0° C. The mixture was stirred at 15° C. for 2 hours. On completion, the reaction mixture was concentrated to obtain 2-(5-fluoro-1H-indol-3-yl)-2-oxoacetyl chloride (8.35 g, 37.01 mmol, 100% yield) as yellow solid.

Step 2: Preparation of 2-(5-fluoro-1H-indol-3-yl)-N,N-dimethyl-2-oxoacetamide

To a solution of N-methylmethanamine hydrochloride (4.53 g, 55.52 mmol, 5.09 mL, 1.5 eq) in DCM (50 mL) was added N,N-diisopropylethylamine (19.13 g, 148.05 mmol, 25.79 mL, 4 eq). The mixture was stirred at 15° C. for 0.5 h. Then a solution of 2-(5-fluoro-1H-indol-3-yl)-2-oxoacetyl chloride (8.35 g, 37.01 mmol, 1 eq) in THF (70 mL) was added at 0° C. and the mixture was stirred at 15° C. for 2 h. On completion, aq. NH₄Cl (100 mL) was added and the mixture was stirred for 5 min. The aqueous phase was extracted with DCM (60 mL×3) and the combined organic phase was dried with anhydrous Na₂SO₄, filtered, and concentrated in vacuo. The residue was purified by column chromatography (SiO₂, petroleum ether/ethyl acetate=5/1 to 0/1) to obtain 2-(5-fluoro-1H-indol-3-yl)-N,N-dimethyl-2-oxoacetamide as a yellow solid (6.67 g, 28.48 mmol, 77% yield). ¹H NMR (400 MHz, CDCl₃) δ 10.33 (br s, 1H), 7.96 (dd, J=2.0, 9.2 Hz, 1H), 7.69 (br d, J=1.6 Hz, 1H), 7.23 (dd, J=4.4, 8.8 Hz, 1H), 6.97 (dt, J=2.4, 9.0 Hz, 1H), 3.10 (s, 3H), 3.06 (s, 3H).

Step 3: Preparation of 2-(5-fluoro-1H-indol-3-yl)-N,N-dimethylethan-1-amine hydrochloride (5)

To a solution of 2-(5-fluoro-1H-indol-3-yl)-N,N-dimethyl-2-oxoacetamide (2 g, 8.54 mmol, 1 eq) in THF (30 mL) was added lithium aluminum hydride (972.25 mg, 25.62 mmol, 3 eq) at 0° C. The mixture was then stirred at 60° C. for 5 h. On completion, the mixture was cooled to 0° C. Water (1 mL) was added and the mixture was stirred for 5 min. Then 30% aq. NaOH (1 mL) was added and the mixture was stirred until the solids were white and free flowing. The mixture was filtered and the filtrate was concentrated in vacuo. The residue was purified by prep-HPLC (column=Phenomenex luna C18 (250*70 mm, 15 μm); mobile phase=water (0.04% HCl)-ACN, B %=1%-27%; R$_T$=20 min) to afford 2-(5-fluoro-1H-indol-3-yl)-N,N-dimethylethan-1-amine hydrochloride (5) as a white solid (1.22 g, 5.91 mmol, 69% yield). ¹H NMR (400 MHz, DMSO-d6) δ 11.12 (br s, 1H), 10.47 (br s, 1H), 7.43 (dd, J=2.4, 10.1 Hz, 1H), 7.39-7.30 (m, 2H), 6.93 (dt, J=2.4, 9.2 Hz, 1H), 3.32-3.22 (m, 2H), 3.14-3.05 (m, 2H), 2.81 (d, J=4.4 Hz, 6H); $^{13}$C NMR (101 MHz, DMSO-d6) (extra peaks due to C-F coupling) δ 158.39, 156.09, 133.40, 127.47, 127.38, 125.95, 113.05, 112.95, 109.98, 109.79, 109.73, 103.76, 103.53, 56.95, 42.44, 20.56; LCMS ($R_T$=2.559 min, MS cal.: 206.12, [M+1-1]+=207.1).

Example 4. Metabolic Stability in Human Liver Microsomes

Disclosed compounds were tested for stability in human liver microsomes (HLM), with the results summarized in Table 1. Compound 2 exhibited greater metabolic stability than Compound 1, N,N-dimethyltryptamine (DMT), 5-methoxy-N,N-dimethyltryptamine (5-MeO-DMT), and psilocin in this model. Compound 4 exhibited metabolic stability greater than its dimethyl analog Compound 5 and ethylpropyl analog Compound 3, and less than its 4-hydroxy analog Compound 6.

Test Compounds. Compounds 3, 4, and 5 were prepared as described above. All other compounds were commercially obtained.

HLM Stability. Pooled HLM from adult male and female donors (Corning 452117) were used. Microsomal incubations were carried out in multi-well plates. Liver microsomal incubation medium consisted of PBS (100 mM, pH 7.4), MgCl$_2$ (1 mM), and NADPH (1 mM), with 0.50 mg of liver microsomal protein per mL. Control incubations were performed by replacing the NADPH-cofactor system with PBS. Test compounds (1 μM, final solvent concentration 1.0%) were incubated with microsomes at 37° C. with constant shaking. Six time points over 60 minutes were analyzed, with 60 μL aliquots of the reaction mixture being drawn at each time point. The reaction aliquots were stopped by adding 180 μL of cold (4° C.) acetonitrile containing 200 ng/mL tolbutamide and 200 ng/mL labetalol as internal standards (IS), followed by shaking for 10 minutes, and then protein sedimentation by centrifugation at 4000 rpm for 20 minutes at 4° C. Supernatant samples (80 μL) were diluted with water (240 μL) and analyzed for parent compound remaining using a fit-for-purpose liquid chromatography-tandem mass spectrometry (LC-MS/MS) method.

Data Analysis. The elimination constant ($k_{el}$), half-life ($t_{1/2}$), and intrinsic clearance ($CL_{int}$) were determined in a plot of ln(AUC) versus time, using linear regression analysis.

TABLE 1

Intrinsic clearance ($CL_{int}$) and half-life ($t_{1/2}$) of compounds in the presence of HLM.

| Compound | Structure | $CL_{int}$ (μL/min/mg) | $t_{1/2}$ (min) |
|---|---|---|---|
| DMT | | 198.6 | 7.0 |
| Psilocin | 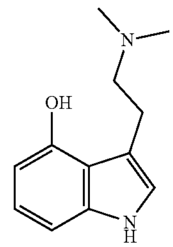 | 12.6 | 109.7 |
| 5-MeO-DMT | 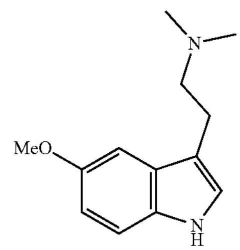 [SMILES: COc1ccc2[nH]cc(CCN(C)C)c2c1] | 101.9 | 13.6 |
| 1* | 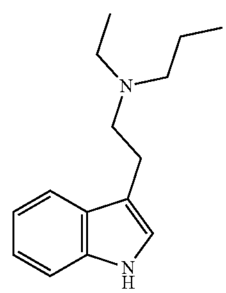 [SMILES: CCCN(CC)CCc1c[nH]c2ccccc12] | 64.3 | 21.7 |
| 2* | 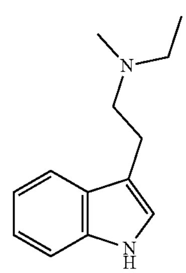 | 11.2 | 125.7 |
| 3 | 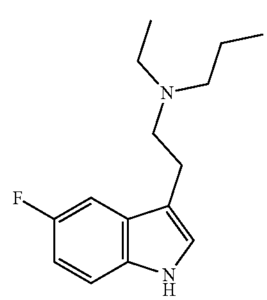 [SMILES: CCCN(CC)CCc1c[nH]c2ccc(F)cc12] | 106.4 | 13.0 |

TABLE 1-continued

Intrinsic clearance (CL$_{int}$) and half-life (t$_{1/2}$) of compounds in the presence of HLM.

| Compound | Structure | Cl$_{int}$ (µL/min/mg) | t$_{1/2}$ (min) |
|---|---|---|---|
| 4 | [5-fluoro-N-methyl-N-ethyl tryptamine structure] | 28.9 | 47.9 |
| 5 | [5-fluoro-N,N-dimethyl tryptamine structure] | 299.7 | 4.6 |
| 6 | [4-hydroxy-N-methyl-N-ethyl tryptamine structure] | <9.6 | >145 |

*Values are the average of two independent experiments.

Example 5. Metabolic Stability in Mouse Liver Microsomes

Disclosed compounds were tested for stability in mouse liver microsomes (MLM), with the results summarized in Table 2. Compound 2 exhibited metabolic stability greater than its dimethyl analog DMT and ethylpropyl analog Compound 1, and less than its 4-hydroxy analog psilocin in this model. Compound 4 exhibited metabolic stability greater than its dimethyl analog Compound 5 and ethylpropyl analog Compound 3, and less than its 4-hydroxy analog Compound 6.

Test Compounds. Compounds 3, 4, and 5 were prepared as described above. All other compounds were commercially obtained.

MLM Stability. Pooled MLM from CD-1 mice (BIOIVT M00501) were used. Microsomal incubations were carried out in multi-well plates. Liver microsomal incubation medium consisted of PBS (100 mM, pH 7.4), MgCl$_2$ (1 mM), and NADPH (1 mM), with 0.50 mg of liver microsomal protein per mL. Control incubations were performed by replacing the NADPH-cofactor system with PBS. Test compounds (1 µM, final solvent concentration 1.0%) were incubated with microsomes at 37° C. with constant shaking. Six time points over 60 minutes were analyzed, with 60 µL aliquots of the reaction mixture being drawn at each time point. The reaction aliquots were stopped by adding 180 µL of cold (4° C.) acetonitrile containing 200 ng/mL tolbutamide and 200 ng/mL labetalol as internal standards (IS), followed by shaking for 10 minutes, and then protein sedimentation by centrifugation at 4000 rpm for 20 minutes at 4° C. Supernatant samples (80 µL) were diluted with water (240 µL) and analyzed for parent compound remaining using a fit-for-purpose liquid chromatography-tandem mass spectrometry (LC-MS/MS) method.

Data Analysis. The elimination constant (k$_{el}$), half-life (t$_{1/2}$), and intrinsic clearance (CL$_{int}$) were determined in a plot of ln(AUC) versus time, using linear regression analysis.

TABLE 2

Intrinsic clearance (CL$_{int}$) and half-life (t$_{1/2}$) of compounds in the presence of MLM.

| Compound | Structure | Cl$_{int}$ (µL/min/mg) | t$_{1/2}$ (min) |
|---|---|---|---|
| DMT | [N,N-dimethyl tryptamine structure] | 20.1 | 69.1 |
| Psilocin | [4-hydroxy-N,N-dimethyl tryptamine structure] | 10.9 | 126.7 |
| 5-MeO-DMT | [5-methoxy-N,N-dimethyl tryptamine structure] | 28.4 | 48.8 |
| 1 | [N-ethyl-N-propyl tryptamine structure] | 231.3 | 6.0 |

TABLE 2-continued

Intrinsic clearance (CL$_{int}$) and half-life (t$_{1/2}$) of compounds in the presence of MLM.

| Compound | Structure | CL$_{int}$ (µL/min/mg) | t$_{1/2}$ (min) |
|---|---|---|---|
| 2 | (N-ethyl, N-methyl tryptamine) | 13.6 | 102.0 |
| 3 | (5-fluoro, N,N-dipropyl tryptamine) | 249.9 | 5.5 |
| 4 | (5-fluoro, N-ethyl, N-methyl tryptamine) | 29.1 | 47.6 |
| 5 | (5-fluoro, N,N-dimethyl tryptamine) | 50.8 | 27.3 |
| 6 | (4-hydroxy, N-ethyl, N-methyl tryptamine) | <9.6 | >145 |

Example 6. Metabolic Stability in Rat Liver Microsomes

Disclosed compounds were tested for stability in rat liver microsomes (RLM), with the results summarized in Table 3. Compounds bearing a 4-hydroxy group showed low to moderate clearance in this model, while all other compounds showed high clearance.

Test Compounds. Compounds 3, 4, and 5 were prepared as described above. All other compounds were commercially obtained.

RLM Stability. Pooled RLM from adult male and female donors (Xenotech R1000) were used. Microsomal incubations were carried out in multi-well plates. Liver microsomal incubation medium consisted of PBS (100 mM, pH 7.4), MgCl$_2$ (1 mM), and NADPH (1 mM), with 0.50 mg of liver microsomal protein per mL. Control incubations were performed by replacing the NADPH-cofactor system with PBS. Test compounds (1 µM, final solvent concentration 1.0%) were incubated with microsomes at 37° C. with constant shaking. Six time points over 60 minutes were analyzed, with 60 µL aliquots of the reaction mixture being drawn at each time point. The reaction aliquots were stopped by adding 180 µL of cold (4° C.) acetonitrile containing 200 ng/mL tolbutamide and 200 ng/mL labetalol as internal standards (IS), followed by shaking for 10 minutes, and then protein sedimentation by centrifugation at 4000 rpm for 20 minutes at 4° C. Supernatant samples (80 µL) were diluted with water (240 µL) and analyzed for parent compound remaining using a fit-for-purpose liquid chromatography-tandem mass spectrometry (LC-MS/MS) method.

Data Analysis. The elimination constant (k$_{el}$), half-life (t$_{1/2}$), and intrinsic clearance (CL$_{int}$) were determined in a plot of ln(AUC) versus time, using linear regression analysis.

TABLE 3

Intrinsic clearance (CL$_{int}$) and half-life (t$_{1/2}$) of compounds in the presence of RLM.

| Compound | Structure | CL$_{int}$ (µL/min/mg) | t$_{1/2}$ (min) |
|---|---|---|---|
| DMT | (N,N-dimethyl tryptamine) | 136.7 | 10.1 |
| Psilocin | (4-hydroxy, N,N-dimethyl tryptamine) | 18.3 | 75.6 |
| 5-MeO-DMT | (5-methoxy, N,N-dimethyl tryptamine) | 98.8 | 14.0 |

TABLE 3-continued

Intrinsic clearance (CL$_{int}$) and half-life (t$_{1/2}$) of compounds in the presence of RLM.

| Compound | Structure | CL$_{int}$ (µL/min/mg) | t$_{1/2}$ (min) |
|---|---|---|---|
| 1 | (N-ethyl, N-propyl tryptamine) | 970.3 | 1.4 |
| 2 | (N-methyl, N-ethyl tryptamine) | 1561.0 | 0.9 |
| 3 | (5-fluoro N-ethyl, N-propyl tryptamine) | 428.2 | 3.2 |
| 4 | (5-fluoro N-methyl, N-ethyl tryptamine) | 229.1 | 6.1 |
| 5 | (5-fluoro N,N-dimethyl tryptamine) | 150.7 | 9.2 |
| 6 | (4-hydroxy N-methyl, N-ethyl tryptamine) | 27.7 | 50.1 |

Example 7. Pharmacokinetics in Mice

The pharmacokinetics of disclosed compounds were studied in the plasma (Table 4) and brains (Table 5) of mice after intravenous (IV), subcutaneous (SC), and oral (PO) dosing. Compounds 2 and 4 demonstrated much improved absolute oral bioavailability (F) compared to the ethylpropyl analog Compound 1, consistent with the greater stability of Compounds 2 and 4 in mouse liver microsomes (see Example 5 above). Despite this much improved oral exposure, the half-life of Compounds 2 and 4 was relatively short. The half-life of Compound 4 was intermediate between its dimethyl analog Compound 5 and its 4-hydroxy analog Compound 6. Further, Compound 4 showed much greater brain exposure than its dimethyl analog Compound 5 after SC administration. Overall, the findings indicate that Compounds 2 and 4 may serve as orally active and short-acting therapeutic agents.

Animals. Male C57BL/6 mice, aged 8-12 weeks, were used in these studies. Four mice were housed in each cage. Temperature and humidity were maintained at 22±3° C. and 30-70%, respectively, and illumination was controlled to give a 12 h light and 12 h dark cycle. Temperature and humidity were recorded by an auto-controlled data logger system. All animals were provided laboratory rodent diet. Reverse osmosis water treated with ultraviolet light was provided ad libitum. Animals were randomly assigned to treatment groups.

Drugs. Compounds 4 and 5 were prepared as described above. All other compounds were commercially obtained. Test compounds were used as the hydrogen fumarate (1 and 2) or hydrochloride (3, 4, and 5) salts and were dissolved in a vehicle consisting of normal saline. They were then administered intravenously (IV) via the tail vein, subcutaneously (SC), or orally (PO) via gavage at a dose of 1 or 10 mg/kg (calculated based on the free base) and at a volume of 5 mL/kg body weight.

Sample Collection and Bioanalysis. Blood samples (approximately 60 µL) were collected under light isoflurane anesthesia (Surgivet®) from the retro orbital plexus at 0.08, 0.25, 0.5, 1, 2, 4, 8, and 24 h (4 animals per time point). Immediately after blood collection, plasma was harvested by centrifugation at 4,000 rpm for 10 min at 4° C. and samples were stored at −70±10° C. until bioanalysis. Following blood collection, animals were immediately sacrificed, the abdominal vena-cava was cut open, and the whole body was perfused from the heart using 10 mL of normal saline, and brain samples were collected from all animals. After isolation, brain samples were rinsed three times in ice-cold normal saline (for 5-10 seconds/rinse using ~5-10 mL normal saline in disposable petri dish for each rinse) and dried on blotting paper. Brain samples were homogenized using ice-cold phosphate-buffered saline (pH 7.4). Total homogenate volume was three times the tissue weight. All homogenates were stored at −70±10° C. until bioanalysis. For bioanalysis, 25 µL aliquots of plasma/brain study samples or spiked plasma/brain calibration standards were added to individual pre-labeled micro-centrifuge tubes followed by 100 µL of an internal standard solution (glipizide, 500 ng/mL in acetonitrile) except for blanks, where 100 µL of acetonitrile was added. Samples were vortexed for 5 minutes and then centrifuged for 10 minutes at 4,000 rpm at 4° C. Following centrifugation, 100 µL of each clear supernatant was transferred to a 96 well plate and analyzed with a fit-for-purpose LC-MS/MS method, with authentic samples of each analyte used for calibration and identification.

Data Analysis. Pharmacokinetic parameters were estimated using the non-compartmental analysis tool of Phoenix® WinNonlin software (Ver 8.0).

TABLE 4

Selected pharmacokinetic parameters of compounds in plasma of C57BL/6 mice (10 mg/kg unless otherwise indicated).

| Compound | Route | $T_{max}$ (h) | $C_{max}$* (ng/mL) | $AUC_{0-last}$ (h*ng/mL) | $t_{1/2}$ (h) | Cl (mL/min/kg) | F (%)** |
|---|---|---|---|---|---|---|---|
| Psilocin | oral | 0.17 | 85.9 | 51.1 | 1.96 | NC | 64 |
| (1 mg/kg) | IV | NA | 195 | 79.9 | 1.1 | 204 | NA |
| 1 | oral | 0.08 | 20.32 | 22.1 | 1.88 | NC | 2.6 |
|  | IV | NA | 3,820.7 | 844.34 | 1.9 | 197.39 | NA |
| 2 | oral | 0.25 | 102.32 | 238.21 | 1.37 | NC | 44 |
|  | IV | NA | 962.59 | 544.61 | 1.48 | 304.48 | NA |
| 4 | oral | 0.25 | 272.25 | 623.37 | 1.34 | NC | 35 |
|  | IV | NA | 2,913.74 | 1,793.37 | 0.86 | 92.85 | NA |
|  | SC | 0.5 | 631.13 | 1,173.65 | 0.9 | NC | 65 |
| 4 (1 mg/kg) | SC | 0.08 | 83.25 | 57.47 | 0.45 | NC | 32 |
| 5 | SC | 0.25 | 362.63 | 246.62 | 0.27 | NC | NC |
| 5 (1 mg/kg) | SC | 0.08 | 41.59 | 10.99 | NC | NC | NC |
| 6 | SC | 0.08 | 1,158.93 | 1,411.6 | 1.1 | NC | NC |

*For IV, $C_{max} = C_0$ values back-extrapolated to t = 0;
**Based on plasma $AUC_{0-last}$;
NC = not calculated;
NA = not applicable.

TABLE 5

Selected pharmacokinetic parameters of compounds in brains of C57BL/6 mice (10 mg/kg unless otherwise indicated).

| Compound | Route | $T_{max}$ (h) | $C_{max}$* (ng/g) | $AUC_{0-last}$ (h*ng/g) | $t_{1/2}$ (h) | Cl (mL/min/kg) | F (%)** |
|---|---|---|---|---|---|---|---|
| Psilocin | oral | 0.17 | 211 | 399 | 2.91 | NC | 57 |
| (1 mg/kg) | IV | NA | 1197 | 702 | 3.03 | 24.1 | NA |
| 1 | oral | 0.25 | 101.08 | 68.93 | 0.66 | NC | 1.4 |
|  | IV | NA | 15,380.61 | 4,754.52 | 1.73 | NC | NA |
| 2 | oral | 0.5 | 956.73 | 1,988.41 | 7.52 | NC | 51 |
|  | IV | NA | 6,250.81 | 3,923.27 | 1.54 | NC | NA |
| Psilocin | oral | 0.17 | 211 | 399 | 2.91 | NC | 57 |
| (1 mg/kg) | IV | NA | 1197 | 702 | 3.03 | 24.1 | NA |
| 4 | oral | 0.25 | 1,396.19 | 3,835.86 | 1.32 | NC | 37 |
|  | IV | NA | 7,976.02 | 10,471.19 | 0.94 | NC | NA |
|  | SC | 1 | 3,505.16 | 6,672.16 | 0.82 | NC | 64 |
| 4 (1 mg/kg) | SC | 0.25 | 460.84 | 320.97 | 0.37 | NC | 31 |
| 5 | SC | 0.25 | 777.92 | 376.09 | NC | NC | NC |
| 5 (1 mg/kg)# | SC | 0.08 | 22.04 | NC | NC | NC | NC |
| 6 | SC | 0.5 | 2,924.86 | 3,549.18 | 1.07 | NC | NC |

*For IV, $C_{max} = C_0$ values back-extrapolated to t = 0;
**Based on brain $AUC_{0-last}$;
Concentrations only quantifiable at 0.08 and 0.25 h so PK parameters not calculated;
NC = not calculated;
NA = not applicable.

Example 8. Pharmacokinetics in Rats

The pharmacokinetics of disclosed compounds were studied in the plasma (Table 6) and brains (Table 7) of rats after subcutaneous (SC) dosing. Compound 4 demonstrated an intermediate exposure and elimination rate in the plasma and brain compared to its dimethyl analog Compound 5 and its 4-hydroxy analog Compound 6 (FIG. 1), consistent with a favorable duration of action for therapeutic use intermediate between DMT-like compounds (very short duration) and psilocin-like compounds (long duration). Compound 4 also demonstrated much higher exposure in brain than its dimethyl analog Compound 5.

Animals. Male Sprague Dawley rats, aged 8-12 weeks, were used in these studies. Four rats were housed in each cage. Temperature and humidity were maintained at 22±3° C. and 30-70%, respectively, and illumination was controlled to give a 12 h light and 12 h dark cycle. Temperature and humidity were recorded by an auto-controlled data logger system. All animals were provided laboratory rodent diet and were fasted for 4 h pre-dose and 2 h post-dose. Reverse osmosis water treated with ultraviolet light was provided ad libitum. Animals were randomly assigned to treatment groups.

Drugs. Compounds 4 and 5 were prepared as described above. Compound 6 was commercially obtained. Test compounds were used as the hydrogen fumarate (6) or hydrochloride (4 and 5) salts and were dissolved in a vehicle consisting of normal saline. They were then administered subcutaneously (SC) at a dose of 1 or 10 mg/kg (calculated based on the free base) and at a volume of 5 mL/kg body weight.

Sample Collection and Bioanalysis. Blood samples (approximately 120 µL) were collected under light isoflurane anesthesia (Surgivet®) from the retro orbital plexus at 0.08, 0.25, 0.5, 1, 2, 4, 8, and 24 h (4 animals per time point). Immediately after blood collection, plasma was harvested by centrifugation at 4,000 rpm for 10 min at 4° C. and samples were stored at −70±10° C. until bioanalysis. Following blood collection, animals were immediately sacrificed, the abdominal vena-cava was cut open, and the whole body was perfused from the heart using 10 mL of normal saline, and brain samples were collected from all animals. After isolation, brain samples were rinsed three times in ice-cold normal saline (for 5-10 seconds/rinse using ~5-10 mL normal saline in disposable petri dish for each rinse) and dried on blotting paper. Brain samples were homogenized using ice-cold phosphate-buffered saline (pH 7.4). Total homogenate volume was three times the tissue weight. All homogenates were stored at −70±10° C. until bioanalysis. For bioanalysis, 25 µL aliquots of plasma/brain study samples or spiked plasma/brain calibration standards were added to individual pre-labeled micro-centrifuge tubes followed by 100 µL of an internal standard solution (glipizide, 500 ng/mL in acetonitrile) except for blanks, where 100 µL of acetonitrile was added. Samples were vortexed for 5 minutes and then centrifuged for 10 minutes at 4,000 rpm at 4° C. Following centrifugation, 100 µL of each clear supernatant was transferred to a 96 well plate and analyzed with a fit-for-purpose LC-MS/MS method, with authentic samples of each analyte used for calibration and identification.

Data Analysis. Pharmacokinetic parameters were estimated using the non-compartmental analysis tool of Phoenix® WinNonlin software (Ver 8.0).

TABLE 6

Selected pharmacokinetic parameters of compounds in plasma of Sprague Dawley rats (10 mg/kg unless otherwise indicated).

| Compound | Route | $T_{max}$ (h) | $C_{max}$ (ng/mL) | $AUC_{0-last}$ (h*ng/mL) | $t_{1/2}$ (h) |
|---|---|---|---|---|---|
| 4 | SC | 1 | 237.27 | 498.69 | NC |
| 4 (1 mg/kg) | SC | 0.5 | 41.26 | 46.80 | NC |
| 5 | SC | 0.25 | 242.52 | 266.26 | 0.55 |
| 6 | SC | 2 | 624.18 | 2,999.38 | NC |

NC = not calculated

TABLE 7

Selected pharmacokinetic parameters of compounds in brains of Sprague Dawley rats (10 mg/kg unless otherwise indicated).

| Compound | Route | $T_{max}$ (h) | $C_{max}$ (ng/g) | $AUC_{0-last}$ (h*ng/g) | $t_{1/2}$ (h) |
|---|---|---|---|---|---|
| 4 | SC | 1 | 2,478.8 | 4,710.96 | 0.52 |
| 4 (1 mg/kg) | SC | 0.25 | 187.99 | 197.70 | 0.39 |
| 5 | SC | 0.25 | 274.69 | 93.99 | 0.39 |
| 6 | SC | 2 | 6,158.42 | 30,638.13 | 2.09 |

Example 9. CYP Inhibition in Human Liver Microsomes

Inhibition of five major cytochrome P450 (CYP) enzymes (1A2, 2C9, 2C19, 2D6, and 3A4) by the disclosed compounds was determined in human liver microsomes (HLM) by using LC-MS/MS to monitor the metabolic conversion of a cocktail of reference CYP substrates in the presence and absence of the test compounds (Table 8). For indicated compounds, a fixed test concentration of 10 µM was used and inhibition expressed as a percentage. For the remainder, multiple concentrations were tested and an $IC_{50}$ was determined. The test compounds generally exhibited limited inhibition of CYPs. At most of the CYPs tested, Compounds 2 and 4 exhibited the least inhibition. In particular, Compounds 2 and 4 showed substantially less inhibition of CYP2D6 than their ethylpropyl analogs Compounds 1 and 3, respectively.

Test Compounds. Compounds 3 and 4 were prepared as described above. All other compounds were commercially obtained.

HLM Incubations. Pooled HLM from adult male and female donors (Corning 452117) were used. Microsomal incubations were carried out in multi-well plates. Liver microsomal incubation aliquots contained 1) PBS (100 mM, pH 7.4), $MgCl_2$ (3.3 mM), and NADPH (1 mM); 2) liver microsomal protein (0.2 mg/mL); 3) the reference CYP substrates: phenacetin for CYP1A2 (10 µM), diclofenac for CYP2C9 (5 µM), (S)-mephenytoin for CYP2C19 (30 µM), dextromethorphan for CYP2D6 (5 µM), and midazolam for CYP3A4 (2 µM); and 4) test compounds (10 µM), control inhibitors (3 µM α-naphthoflavone for CYP1A2, 3 µM sulfaphenazole for CYP2C9, 1 µM (+)-N-3-benzylnirvanol for 2C19, 3 µM quinidine for CYP2D6, or 3 µM ketoconazole for CYP3A4), or solvent (for uninhibited condition). Incubations were carried out at 37° C. with constant shaking for 10 minutes. The reaction aliquots were stopped by adding 400 µL of cold (4° C.) acetonitrile containing 200 ng/mL tolbutamide and 200 ng/mL labetalol as internal standards (IS), followed by protein sedimentation by centrifugation at 4,000 rpm for 20 minutes at 4° C.

Sample Analysis. Supernatant samples (200 μL) were diluted with water (100 μL) and the reference metabolites of each reference CYP substrate were quantified using a fit-for-purpose liquid chromatography-tandem mass spectrometry (LC-MS/MS) method. Percent inhibition by test compounds or control inhibitors was calculated by comparing the metabolite formation in the presence of the inhibitor compared to the metabolite formation in the absence of the inhibitor.

TABLE 8

$IC_{50}$ or % inhibition at 10 μM of indicated CYPs by test compounds.

| | CYP % Inhibition at 10 μM or ($IC_{50}$, μM)[#] | | | | |
|---|---|---|---|---|---|
| Compound | 3A4 | 2D6 | 1A2 | 2C19 | 2C9 |
| DMT | 5.5 | 5.8 | 7.3 | 0.0 | 2.7 |
| 5-MeO-DMT | 0.0 | 4.4 | 4.0 | 0.0 | 1.0 |
| Psilocin | 0.0 | 13.7 | 22.5 | 0.0 | 0.0 |
| 1* | 2.0 | 58.6 | 37.1 | 2.3 | 0.1 |
| 2 | 0.0 | 11.5 | 0.5 | 0.0 | 0.0 |
| | (>50) | (31.5) | (>50) | (>50) | (>50) |
| 3 | (>50) | (1.9) | (8.4) | (>50) | (>50) |
| 4 | (>50) | (>50) | (>50) | (>50) | (>50) |
| 6 | (>50) | (48.5) | (>50) | (>50) | (>50) |

[#]Values in parentheses are $IC_{50}$s; all other values are % inhibition at 10 μM; *Values are the average of two independent experiments.

Example 10. Stability in the Presence of Monoamine Oxidases

Disclosed compounds were tested for stability in the presence of monoamine oxidase A and B (MAO-A and MAO-B) in human liver mitochondria preparations, with the results summarized in Table 9. Disclosed compounds, with the exception of Compound 5, exhibited good MAO stability in this model. Compounds bearing two methyl substituents on the amine and lacking a 4-hydroxy substituent on the indole (DMT, 5-MeO-DMT, and 5) were highly metabolized by MAO. In contrast, compounds with bearing an ethyl and propyl substituent on the amine (1 and 3) or a 4-hydroxy substituent on the indole (psilocin and 6) were highly stable in the MAO preparation. Compounds 2 and 4 were of intermediate stability, consistent with their intermediate half-life and exposure in PK studies (see Examples 7 and 8).

Test Compounds. Compounds 3, 4, and 5 were prepared as described above. All other compounds were commercially obtained.

Liver Mitochondria Incubations. Human liver mitochondria (Xenotech H0610.M) were used. Mitochondrial incubations were carried out in multi-well plates. Liver mitochondrial incubation medium consisted of PBS (100 mM, pH 7.4) with 0.30 mg of liver mitochondrial protein per mL. Test compounds (1 μM, final solvent concentration 1.0%) were incubated with liver mitochondrial protein at 37° C. with constant shaking (total reaction volume 100 μL per well). Six time points over 60 minutes were analyzed. At each time point, reactions were stopped by adding 300 μL of cold (4° C.) acetonitrile containing 200 ng/mL tolbutamide and 200 ng/mL labetalol as internal standards (IS), followed by shaking for 10 minutes, and then protein sedimentation by centrifugation at 4000 rpm for 20 minutes at 4° C. Supernatant samples (100 μL) were diluted with 5% trichloroacetic acid in water (300 μL) and analyzed for parent compound remaining using a fit-for-purpose liquid chromatography-tandem mass spectrometry (LC-MS/MS) method.

Data Analysis. The elimination constant ($k_{el}$), half-life ($t_{1/2}$), and intrinsic clearance ($CL_{int}$) were determined in a plot of ln(AUC) versus time, using linear regression analysis.

TABLE 9

Intrinsic clearance ($CL_{int}$), half-life ($t_{1/2}$), and percent remaining of compounds in the presence of monoamine oxidases (human mitochondrial preparation).

| Compound | $t_{1/2}$ (min) | $CL_{int(MAO)}$ (μL/min/mg) | Remaining (t = 60 min) |
|---|---|---|---|
| DMT | 17.1 | 134.9 | 8.9% |
| Psilocin | >145 | <15.9 | 112.1% |
| 5-MeO-DMT | 52.9 | 43.6 | 47.1% |
| 1 | >145 | <15.9 | 95.1% |
| 2 | >145 | <15.9 | 84.5% |
| 3 | >145 | <15.9 | 97.7% |
| 4 | >145 | <15.9 | 75.0% |
| 5 | 8.7 | 266 | 0.9% |
| 6 | >145 | <15.9 | 112.3% |

Example 11. Functional Activity at Serotonin Receptors

Disclosed compounds were tested for agonist activity at several serotonin receptor subtypes (5-HT2A, 2-HT2B, 5-HT2C, and 5-HT1A) using $Ca^{2+}$ flux functional assays, with the results summarized in Table 10. All compounds exhibited potent agonist activity at 5-HT2A, suggestive of potential hallucinogenic activity as well as possible therapeutic effects. However, the signaling efficacy at 5-HT2A and the selectivity for this target over other serotonin receptors varied dramatically with even small changes to the chemical structure. For example, Compounds 1 and 3 showed little selectivity for 5-HT2A over 5-HT2B, whereas Compounds 2 and 4 were highly selective for 5-HT2A relative to 5-HT2B. At the same time, Compound 1 was a highly efficacious agonist at 5-HT2A ($E_{max}$=85.2%), whereas Compound 2 was a low efficacy partial agonist ($E_{max}$=36.2%). Fluorination at the 5 position of the indole ring also had unpredictable effects. For example, Compounds 3 and 4 were both significantly more potent at the 5-HT1A receptor than their non-fluorinated analogs Compounds 1 and 2, respectively. In the case of Compound 3, fluorination also increased potency at 5-HT2A relative to Compound 1. In the case of Compound 4, fluorination had little effect on potency at 5-HT2A, but dramatically increased the maximal efficacy compared to Compound 2, resulting in a high efficacy rather than partial agonist. Fluorination also decreased the maximal efficacy of signaling at 5-HT2B, as Compounds 3 and 4 induced lower maximal activation that Compounds 1 and 2, respectively, at this receptor.

Test Compounds. Compounds 3 and 4 were prepared as described above. All other compounds were commercially obtained.

Functional Assays at 5-HT2A, 5-HT2B, and 5-HT1A. Agonist activity at 5-HT2A, 5-HT2B, and 5-HT1A receptors was determined using a FLIPR $Ca^{2+}$ flux assay at WuXi AppTec (Hong Kong) Limited according to their standard protocols. Briefly, stably transfected cells expressing the receptor of interest (HEK293 for 5-HT2A and 5-HT2B; CHO cells for 5-HT1A) were grown and plated in a 384 well plate and incubated at 37° C. and 5% $CO_2$ overnight. A solution of 250 mM probenecid in 1 mL FLIPR assay buffer was prepared fresh. This was combined with a fluorescent dye (Fluo-4 Direct™) to make a final assay concentration of 2.5 mM. Compounds were diluted 1:3.16 for 10 points and 750 nL was added to a 384 well compound plate using ECHO along with 30 μL assay buffer. The fluorescent dye was then added to the assay plate along with assay buffer to a final volume of 40 μL. The cell plate was incubated for 50 min at 37° C. and 5% $CO_2$ and placed into the FLIPR Tetra along with the compound plate. 10 μL of references and compounds were then transferred from the compound plate into the cell plate and the fluorescent signal was read.

Functional Assays at 5-HT2C. Agonist activity at 5-HT2C was determined using a FLIPR $Ca^{2+}$ flux assay at Eurofins DiscoverX (Fremont, Calif.) according to their standard protocols. Briefly, stably transfected cells expressing the human 5-HT2C receptor were grown and plated in a 384 well plate and incubated at 37° C. and 5% $CO_2$ overnight. Assays were performed in 1× Dye Loading Buffer consisting of 1× Dye, 1× Additive A, and 2.5 mM Probenecid in HBSS/20 mM Hepes. Probenecid was prepared fresh. Cells were loaded with dye prior to testing and incubated at 37° C. for 30-60 minutes. After dye loading, cells were removed from the incubator and 10 μL HBSS/20 mM Hepes was added. 3× vehicle was included in the assay buffer. Cells were incubated for 30 mins at room temperature in the dark to equilibrate plate temperature. Intermediate dilution of sample stocks was performed to generate 4× sample in assay buffer. Compound agonist activity was measured on a FLIPR Tetra (MDS). Calcium mobilization was monitored for 2 minutes and 10 μL 4× sample in HBSS/20 mM Hepes was added to the cells 5 seconds into the assay.

Figure 2:
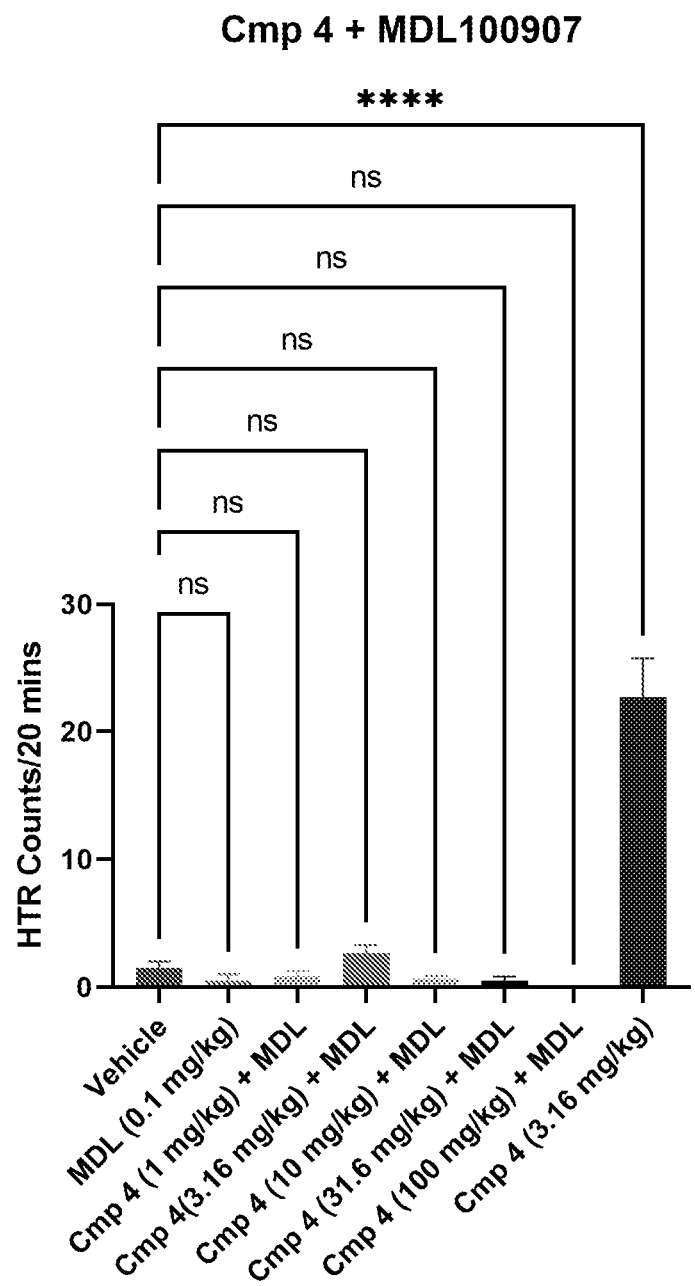
FIG. 2 depicts a bar graph of Blockade of the Head Twitch Response in Mice. A one-way ANOVA revealed a significant main effect of treatment ($F(7,32)=36.91$, $P<0.0001$) on the total number of HTR counts. Dunnett's multiple comparisons test was used to test if a group was significantly different from vehicle. Only Cmp 4 alone was significantly different from vehicle ($P<0.0001$). **** $P<0.0001$ vs. vehicle.

Compounds 3 and 4 as 5-HT2A agonists in vitro (see Example 11 above). The maximal HTR induced by Compounds 3 and 4 was similar to that of the prototype 5-HT2A agonist 4-iodo-2,5-dimethoxyamphetamine (DOI) (35.6 head twitches/20 min). Additionally, pretreatment with 0.1 mg/kg (SC) of the selective 5-HT2A antagonist MDL100907 completely blocked the HTR induced by Compound 4, even at very high doses (FIG. 2), demonstrating that the HTR induced by Compound 4 is dependent on 5-HT2A activation.

Animals. Adult male C57BL/6 mice, aged 8 weeks (body weight 20-25 g) were used in these experiments. Animals were housed under controlled temperatures and 12-hour light/dark cycles (lights on between 07:00-19:00 h), with ad libitum food and water. The protocol was approved by the Eurofins Advinus Institutional Animal Care and Use Committee. This study was carried out in strict accordance with the recommendations in the Guide for the Care and Use of Laboratory Animals of the National Institutes of Health. All efforts were made to minimize suffering.

Drugs and Drug administration. Compounds 3 and 4 were prepared as described above. All other compounds were commercially obtained. Test compounds were used as the hydrogen fumarate (1 and 2) or hydrochloride (DOI, 3, and 4) salts. Drugs were dissolved in a vehicle consisting of normal saline and administered subcutaneously (SC) in a volume of 10 mL/kg. Test compounds were administered at 5 doses per compound (0.1 to 100 mg/kg, as indicated, calculated based on the free base) using N=6 animals/group. The control compound DOI was administered at 1 dose

TABLE 10

Agonist activity of compounds at select serotonin receptors in $Ca^{2+}$ flux functional assays.

| Compound | 5-HT2A $EC_{50}$ (nM) | 5-HT2A % Act @ Max Dose | 5-HT2B $EC_{50}$ (nM) | 5-HT2B % Act @ Max Dose | 5-HT2C $EC_{50}$ (nM) | 5-HT2C % Act @ Max Dose | 5-HT1A $EC_{50}$ (nM) | 5-HT1A % Act @ Max Dose |
|---|---|---|---|---|---|---|---|---|
| 1 | 30.5 | 85.2 | 40.3 | 80.4 | 33.4 | 90.8 | 88,700 | 75.5 |
| 2 | 17.1 | 36.2 | >100,000 | 22.5 | 28.3 | 89.7 | 59,500 | 73.6 |
| 3 | 5.535 | 104.1 | 15.42 | 64.64 | NT | NT | 19,581 | 88.34 |
| 4 | 20.6 | 87.6 | >10,000 | 0.79 | 9.459 | 85.13 | 16,918 | 83.01 |
| 6 | 15.14 | 103.0 | >10,000 | 1.09 | NT | NT | 14,709 | 72.96 |
| DMT* | 22.2 | 93.4 | >31,600 | 10.4 | 31.3 | 92.0 | >100,000 | 68.1 |
| psilocin* | 6.50 | 95.6 | 4,290 | 1.44 | 30.3 | 95.1 | >3,160 | 0.720 |
| 5-MeO-DMT* | 1.76 | 106 | 30.1 | 20.5 | 10.1 | 89.8 | 280 | 78.8 |

*Values are the average of two or more independent experiments;
NT = not tested.

Example 12. Effects on the Head Twitch Response (HTR) in Mice

Disclosed compounds were tested for their ability to induce a head twitch response (HTR) in mice, with the results summarized in Table 11. Consistent with their agonist activity at the 5-HT2A receptor, all tested compounds induced the HTR. However, the disclosed compounds varied in their maximal effect in this assay. The maximal effects of fluorinated Compounds 3 (29.33 head twitches/20 min) and 4 (27.67 head twitches/20 min) were both much higher than those of their non-fluorinated counterparts Compounds 1 (14.7 head twitches/20 min) and 2 (6.00 head twitches/20 min), respectively, consistent with the higher efficacy of (3.16 mg/kg, calculated based on the HCl salt), using N=12 animals. For blockade experiments, MDL100907 (0.1 mg/kg, SC) was administered 10 mins prior to the test compound.

Procedure. Mice were administered one dose of a test drug (or vehicle) s.c. and immediately placed into a small open field for behavioral observation. Animals were observed continuously for 20 mins and the number of HTRs were counted by an observer blind to the treatment condition.

Statistical analysis. The data points shown in Table 11 are the mean±standard error of the mean (SEM). Analysis was performed using GraphPad Prism 9.

TABLE 11

HTR of compounds in mice.

| Compound | Dose (mg/kg) | Average HTR (SEM) |
|---|---|---|
| DOI | 3.16 | 35.583 (3.372) |
| 1 | 1 | 14.667 (2.848) |
| 1 | 3.16 | 12.167 (1.682) |
| 1 | 10 | 8.000 (1.966) |
| 1 | 31.6 | 4.750 (1.797) |
| 1 | 100 | 4.500 (0.866) |
| 2 | 1 | 3.667 (0.615) |
| 2 | 3.16 | 6.000 (0.632) |
| 2 | 10 | 2.500 (0.563) |
| 2 | 31.6 | 1.000 (0.408) |
| 2 | 100 | 0.500 (0.500) |
| 3 | 0.1 | 12.5 (0.671) |
| 3 | 0.316 | 15.667 (1.33) |
| 3 | 1 | 29.333 (2.186) |
| 3 | 3.16 | 22.167 (1.537) |
| 3 | 10 | 26.333 (1.667) |
| 4 | 0.1 | 5.00 (1.065) |
| 4 | 0.316 | 14.00 (0.816) |
| 4 | 1 | 18.333 (1.229) |
| 4 | 3.16 | 27.667 (1.626) |
| 4 | 10 | 9.333 (1.022) |

Example 13. Forced Swim Test in Rats

Figure 3:
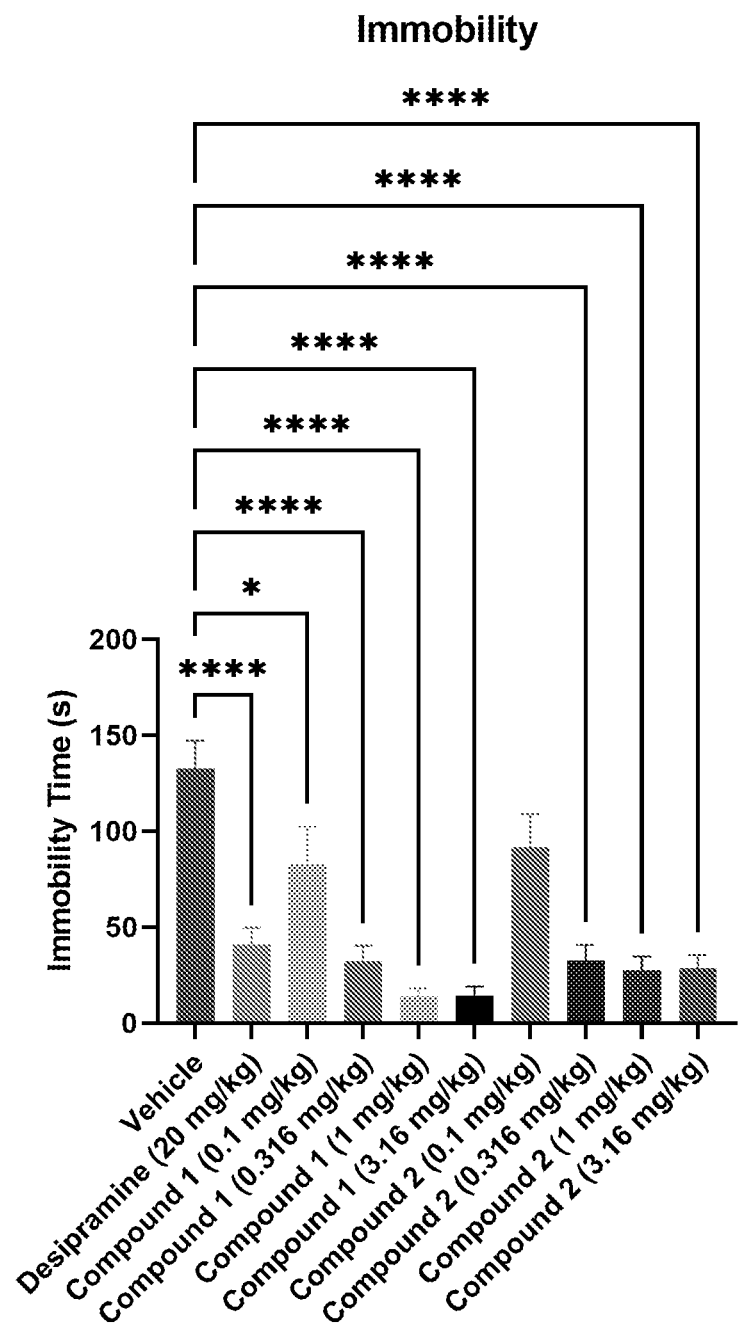
FIG. 3 depicts a bar graph of immobility time in the FST. A one-way ANOVA revealed a significant main effect of treatment ($F(9,99)=12.42$, $P<0.0001$) on the total time spent immobile in the FST. Dunnett's multiple comparisons test was used to test if a group was significantly different from vehicle. All treatments except for Compound 2 at 0.1 mg/kg were significantly different from vehicle. * $P<0.05$, **** $P<0.0001$ vs. vehicle.
Figure 4:
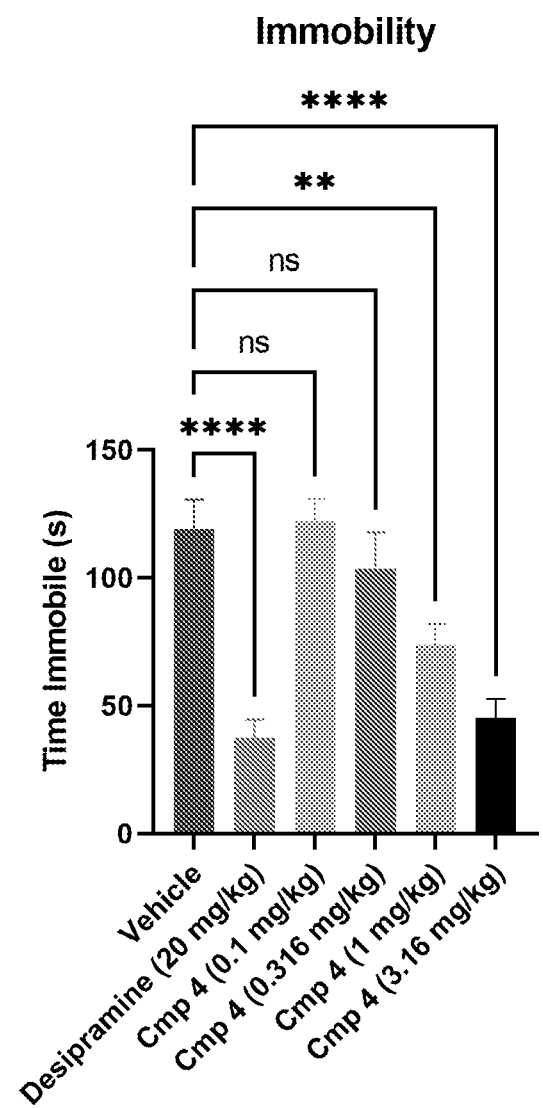
FIG. 4 depicts a bar graph of immobility time in the FST. A one-way ANOVA revealed a significant main effect of treatment ($F(5.54)=14.09$, $P<0.0001$) on the total time spent immobile in the FST. Dunnett's multiple comparisons test was used to test if a group was significantly different from vehicle.  $P<0.01$, ** $P<0.0001$ vs. vehicle.
Figure 5:
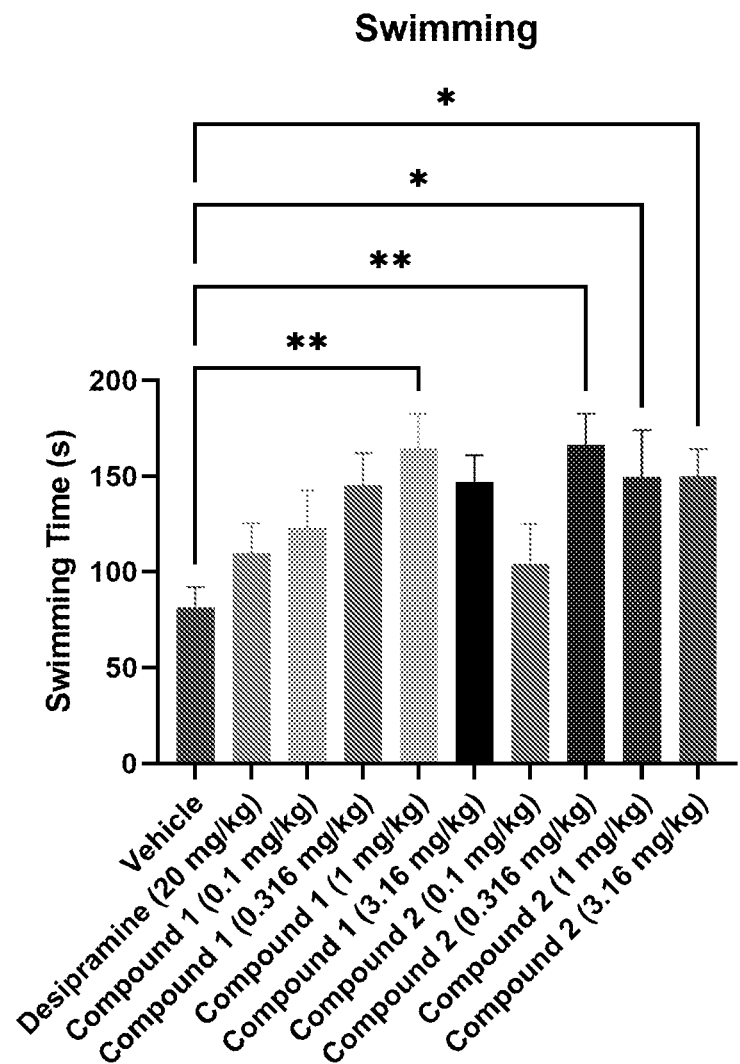
FIG. 5 depicts a bar graph of swimming time in the FST. A one-way ANOVA revealed a significant main effect of treatment ($F(9,99)=2.653$, $P=0.0090$) on the total time spent swimming in the FST. Dunnett's multiple comparisons test was used to test if a group was significantly different from vehicle. * $P<0.05$, ** $P<0.01$ vs. vehicle.

Disclosed compounds induced antidepressant-like effects in the forced swim test (FST) in rats with a 23.5-h pretreatment time. Specifically, the compounds reduced immobility time relative to vehicle control, indicative of an antidepressant-like effect (FIG. 3 and FIG. 4). These effects on immobility were observed 23.5 hours after a single compound administration, a time point at which most or all of the drug has been cleared from the systemic circulation, suggesting that the compounds have both rapid-acting and long-lasting antidepressant-like effects. Additionally, the compounds induced significant increases in swimming behavior during the test (FIG. 5). These effects on swimming were stronger than those induced by the control antidepressant desipramine.

Animals. Male Sprague Dawley rats, aged 8-10 weeks, were used in the experiments. Animals were housed in groups of 2 under controlled temperature (22±3° C.) and relative humidity (30-70%) conditions, with 12-hour light/dark cycles, and with ad libitum food and water. These studies were carried out in strict accordance with the requirements of the Committee for the Purpose of Control and Supervision of Experiments on Animals (CPCSEA), India. All efforts were made to minimize suffering.

Drugs and Drug Administration. Compound 4 was prepared as described above. All other compounds were commercially obtained. Test compounds, saline vehicle, and the positive control desipramine were administered subcutaneously (SC), with doses calculated based on the free base. Normal saline was used as the vehicle. All compounds were administered at a volume of 5 mL/kg. Test compounds and vehicle were administered 0.5 h after the start of the training swim (Swim 1) and 23.5 h before the test swim (Swim 2). Desipramine was administered 3 times, at 23.5 h, 5 h, and 1 h before the test swim (Swim 2), each time at a dose of 20 mg/kg.

Forced Swim Test (FST). Animals were randomized based on body weight, and it was ensured that inter-group variations were minimal and did not exceed ±20% of the mean body weight across the groups. Group size was N=10 per treatment, except for the vehicle and desipramine groups, which were N=20. Rats were handled for about 2 min daily for the 5 days prior to the beginning of the experimental procedure. On the first day of the experiment (i.e., Day 0), post randomization, training swim sessions (Swim 1) were conducted between 12:00 and 18:00 h with all animals by placing rats in individual glass cylinders (46 cm tall×20 cm in diameter) containing 23-25° C. water 30 cm deep for 15 minutes. At the conclusion of Swim 1, animals were dried with paper towels, placed in heated drying cages for 15 minutes, and then returned to their home cages. Animals were then administered the appropriate drug or vehicle treatment(s), as described above. For clarity, a compound administration time of 23.5 h before Swim 2 means 0.5 h after the start of Swim 1 and 0.25 h after the completion of Swim 1 (i.e., immediately after return to the home cage). On Day 1 (i.e., 24 h after start of Swim 1), animals performed the test swim (Swim 2) for a period of 5 min but otherwise under the same conditions as Swim 1. During all swim sessions, the water was changed between each animal.

Behavioral scoring was conducted by observers who were blind to the treatment groups. Animals were continuously observed during Swim 2 and the total time spent engaging in the following behaviors was recorded: immobile, swimming, and climbing. A rat was judged to be immobile when it remained floating in the water without struggling and was making only those movements necessary to keep its head above water. A rat was judged to be swimming when it made active swimming motions, more than necessary to merely maintain its head above water (e.g., moving around in the cylinder). A rat was judged to be climbing when it made active movements with its forepaws in and out of the water, usually directed against the walls.

Statistical Analysis. The data points shown in FIG. 3, FIG. 4, and FIG. 5 represent the mean±standard error of the mean (SEM). Analysis was performed using GraphPad Prism 9. Comparisons between groups were performed using the one-way analysis of variance (ANOVA), followed by Dunnett's test for comparisons to vehicle.

Example 14. Conditioned Place Preference in Mice

Figure 6:
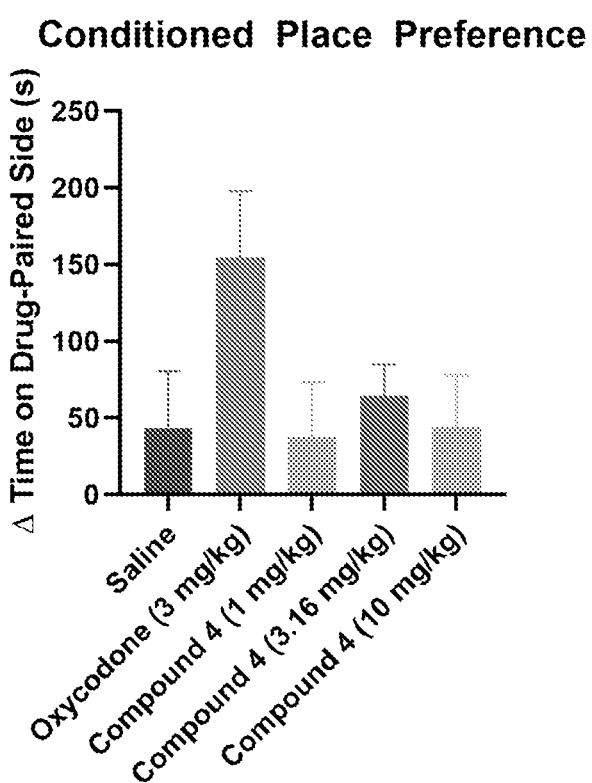
FIG. 6 depicts a bar graph of results of the conditioned place preference test. The effect of Compound 4 was not significantly different from vehicle.

In the conditioned place preference model of abuse liability in mice, Compound 4 did not induce any significant preference for the drug-paired compartment (FIG. 6).

Animals. Male C57BL/6 mice, 5-8 weeks of age, (body weight 25-30 g; Envigo, Indianapolis, Ind., USA) were housed 5 per polycarbonate tub with soft bedding in a temperature- and humidity-controlled vivarium. Mice were maintained under a 12-h light/dark cycle with lights on at 06:00. Food and water were available ad libitum. Animals acclimated to the vivarium for 1 week prior to experimental manipulations.

Drugs and Drug Administration. Compound 4 was prepared as described above. All other compounds were commercially obtained. Compound 4 and saline vehicle were administered subcutaneously (SC), with doses calculated based on the HCl salt, while the positive control oxycodone was administered intraperitoneally (IP), with the dose calculated based on the HCl salt. Normal saline was used as the vehicle. All compounds were administered at a volume of 10 mL/kg. Compound 4, positive control, or vehicle were administered immediately before the start of each conditioning session.

Conditioned Place Preference. Reward and/or aversion was assessed in conditioned place preference chambers (Model MED-CPP-3013; Med Associates, St. Albans, Vt.).

Each chamber (16.75×12.70 cm) has two stimulus-distinct conditioning chambers (wall color and flooring texture) separated by a third central start chamber. Manual guillotine doors permit confinement/access to individual chambers.

Group size was n=10 per treatment. Mice were habituated to the chambers for 15 minutes. The following day, the mice were placed back into the chambers for 15 minutes to establish baselines preferences. Drugs were then administered over a total of 6, 45-minute conditioning trials whereby the test drug was paired to the compartment less preferred (based on baseline score) during 3 conditioning trials (S+) and the vehicle was paired to the preferred compartment (based on baseline score) during 3 conditioning trials (S−). Final drug preference was assessed in a 15-minute post-conditioning trial and was calculated by subtracting the time in the drug-paired compartment at baseline from the time in the drug-paired compartment post-conditioning, with positive values reflecting reward and negative values reflecting aversion.

For all trials, time spent in chambers as well as movement was quantified by infrared photobeam detectors and calculated by Med-PC IV software. Movement was defined as consecutive beam breaks within a chamber to detect forward locomotion. The test apparatus was thoroughly cleaned with 70% ethanol solution after each trial.

Statistical Analysis. The data points shown are the mean±standard error of the mean (SEM). Analysis was performed using GraphPad Prism 9. Comparisons between groups were performed using the one-way analysis of variance (ANOVA), followed by Dunnett's test for comparisons to vehicle.

Example 15. Locomotor Activity in Mice

Figure 7:
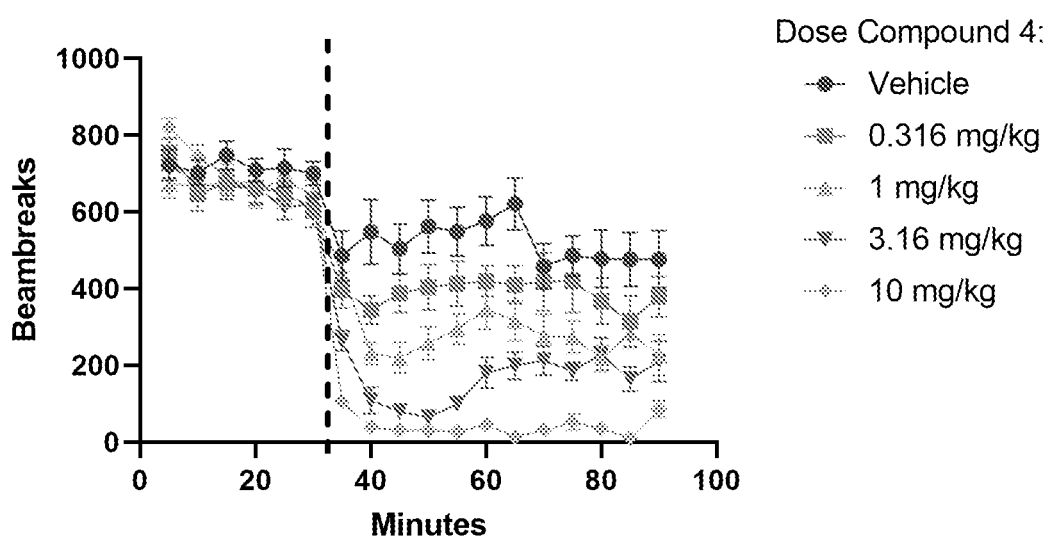
FIG. 7 depicts results of the open field locomotor activity assay. A two-way ANOVA revealed a significant main effect of time ($F(17,765)=189.4$, $P<0.0001$), a significant main effect of treatment ($F(4,45)=16.84$, $P<0.0001$), and a significant treatment×time interaction ($F(68,765)=9.366$, $P<0.0001$).

Compound 4 produced a dose-dependent decrease in total locomotor activity in the open field, indicative of a sedative-like effect. The highest dose group showed a near complete reduction in activity (FIG. 7).

Animals. Male C57BL/6 mice, 5-8 weeks of age, (body weight 25-30 g; Envigo, Indianapolis, Ind., USA) were housed 5 per polycarbonate tub with soft bedding in a temperature- and humidity-controlled vivarium. Mice were maintained under a 12-h light/dark cycle with lights on at 06:00. Food and water were available ad libitum. Animals acclimated to the vivarium for 1 week prior to experimental manipulations.

Drugs and Drug Administration. Compound 4 was prepared as described above. Compound 4 and saline vehicle were administered subcutaneously (SC), with doses calculated based on the HCl salt. Normal saline was used as the vehicle. All compounds were administered at a volume of 10 mL/kg. Compound 4 or vehicle were administered immediately before the start of the recording session.

Locomotor Activity. Locomotor activity was measured in experimental cages (length×width×height: 560×560×330 mm) by an animal movement analysis system SCANET MV-40 (MELQUEST Co., Ltd., Toyama, Japan). The cumulative activity was recorded for 30 minutes prior to drug administration to establish a baseline, and then animals were recorded for 60 minutes immediately after drug administration. Cages were cleaned between testing sessions.

Statistical Analysis. The total number of beam breaks were summed into 5-minute time bins. The data points shown are the mean±standard error of the mean (SEM). Analysis was performed using GraphPad Prism 9. Statistical analysis was performed using the two-way analysis of variance (ANOVA).

Example 16. Marble Burying in Mice

Figure 8:
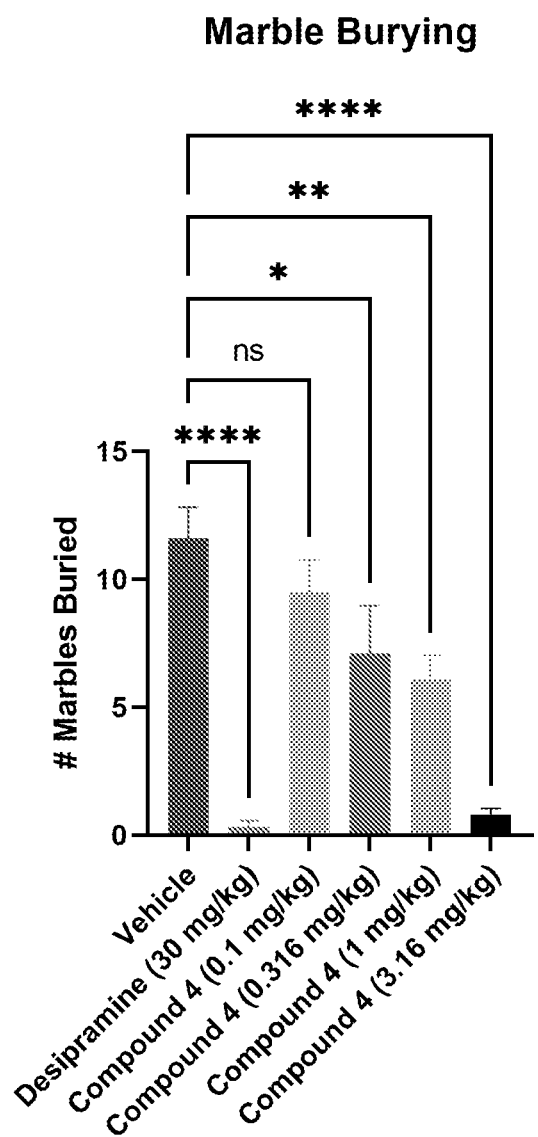
FIG. 8. depicts a bar graph of results of the marble burying test. A one-way ANOVA revealed a significant main effect of treatment ($F(5,53)=15.79$, $P<0.0001$). Dunnett's multiple comparisons test was used to test if a group was significantly different from vehicle. * $P<0.05$,  $P<0.01$, ** $P<0.0001$ vs. vehicle.

Compound 4 produced an anxiolytic-like effect in the marble burying test (MBT) in C57BL/6 mice (FIG. 8). Specifically, Compound 4 showed a dose-dependent reduction in the number of marbles buried in a 30-minute period compared to vehicle.

Animals. Adult male C57BL/6 mice, aged 8-10 weeks (body weight 20-25 g), were used in these experiments. Animals were housed under controlled temperatures and 12-hour light/dark cycles (lights on between 07:00-19:00 h), with ad libitum food and water. All efforts were made to minimize suffering.

Drugs and Drug Administration. Compound 4 was prepared as described above. Desipramine HCl was commercially obtained. The test compound, vehicle, and the positive control desipramine were administered subcutaneously (SC), with doses calculated based on the freebase. Normal saline was used as the vehicle. All compounds were administered at a volume of 10 mL/kg. All treatments were administered 30 minutes prior to the start of behavioral testing. Group size was n=9-10 per treatment.

Marble Burying Test (MBT). Animals were randomized based on body weight, and it was ensured that inter-group variations were minimal and did not exceed ±20% of the mean body weight across the groups. Mice were handled for about 2 min daily for the 3 days prior to the beginning of the experimental procedure. Twenty glass marbles (16 mm diameter) were placed at equal distances in a 5×4 pattern on a 5-cm layer of corn-cob bedding, with marbles at least 2 cm from the borders of the cage. The total number of marbles buried were counted in three 10-minute time bins (total 30 minutes). A marble was considered buried when it was >2/3 covered by bedding material.

Statistical Analysis. The data points shown are the mean±standard error of the mean (SEM). Analysis was performed using GraphPad Prism 6. Comparisons between groups were performed using the one-way analysis of variance (ANOVA), followed by Dunnett's test for comparisons to vehicle.

Example 17. Stability in Mouse Brain Homogenate

Disclosed compounds were tested for stability in mouse brain homogenate (Table 12). There was variable stability among the test compounds under the conditions of the experiment. Psilocin, 5-MeO-DMT, and Compounds 1 and 3 demonstrated high stability, Compounds 2, 4, and 6 demonstrated intermediate stability, and DMT and Compound 5 were highly unstable under the incubation conditions. Fluorinated Compounds 3 and 4 were less stable than their non-fluorinated counterparts Compounds 1 and 2, respectively. Methylethyl Compounds 2 and 4 were more stable than their dimethyl counterparts DMT and Compound 5, respectively.

Test Compounds. Compounds 3, 4, and 5 were prepared as described above. All other compounds were commercially obtained.

Mouse Brain Homogenate Stability. Frozen mouse brain homogenate (pooled from male CD-1 mice, Bioreclamation-IVT, MSEOOBRAINMZA) was thawed in a water bath at 37° C. immediately prior to use. Positive controls and test compounds (final concentration in incubation medium=1

μM for test compounds and 2 μM for controls, all with 2% DMSO) were incubated in duplicate for each time point (0, 10, 30, 60, and 120 min) in the mouse brain homogenate at a total reaction volume of 100 μL at 37° C. At the end of each incubation period, reactions were immediately quenched with 400 μL of acetonitrile containing internal standard (200 ng/mL tolbutamine and 200 ng/mL labetalol) and mixed thoroughly. Plates were then sealed, shaken for 20 min, and centrifuged at 4,000 rpm and 4° C. for 20 min. Aliquots of 50 μL of each supernatant were diluted into 100 uL of water and the mixtures were then shaken again for 10 min. The resulting mixtures were analyzed for parent compound remaining using a fit-for-purpose LC-MS/MS method.

TABLE 12

Stability of compounds in mouse brain homogenate.

| Compound | % Compound Remaining (after 120 min) | $t_{1/2}$ (min) |
|---|---|---|
| DMT | 0.0 | 6.4 |
| 5-MeO-DMT | 91.2 | >289.1 |
| psilocin | 97.6 | >289.1 |
| 1 | 113.8 | >289.1 |
| 2 | 47.8 | 123 |
| 3 | 76.7 | >289.1 |
| 4 | 20.7 | 54.3 |
| 5 | 0.0 | 3.1 |
| 6 | 16.7 | 45.8 |

Example 18. Stability in Rat Brain Homogenate

Disclosed compounds were tested for stability in rat brain homogenate (Table 13). There was variable stability among the test compounds under the conditions of the experiment. Compounds 1, 2, and 3 demonstrated high stability, psilocin and Compounds 4 and 6 demonstrated intermediate stability, and DMT, 5-MeO-DMT, and Compound 5 were highly unstable under the incubation conditions. Methylethyl Compounds 2 and 4 were more stable than their dimethyl counterparts DMT and Compound 5, respectively.

Test Compounds. Compounds 3, 4, and 5 were prepared as described above. All other compounds were commercially obtained.

Rat Brain Homogenate Stability. Frozen rat brain homogenate (pooled from male Sprague Dawley rats, BioreclamationIVT, RATOOBRAINMZA) was thawed in a water bath at 37° C. immediately prior to use. Positive controls and test compounds (final concentration in incubation medium=1 μM for test compounds and 2 μM for controls, all with 2% DMSO) were incubated in duplicate for each time point (0, 10, 30, 60, and 120 min) in the rat brain homogenate at a total reaction volume of 100 μL at 37° C. At the end of each incubation period, reactions were immediately quenched with 400 μL of acetonitrile containing internal standard (200 ng/mL tolbutamine and 200 ng/mL labetalol) and mixed thoroughly. Plates were then sealed, shaken for 20 min, and centrifuged at 4,000 rpm and 4° C. for 20 min. Aliquots of 50 μL of each supernatant were diluted into 100 uL of water and the mixtures were then shaken again for 10 min. The resulting mixtures were analyzed for parent compound remaining using a fit-for-purpose LC-MS/MS method.

TABLE 13

Stability of compounds in rat brain homogenate.

| Compound | % Compound Remaining (after 120 min) | $t_{1/2}$ (min) |
|---|---|---|
| DMT | 0.0 | 5.1 |
| 5-MeO-DMT | 0.3 | 14.4 |
| Psilocin | 46.1 | 114.8 |
| 1 | 86.9 | >289.1 |
| 2 | 76.5 | >289.1 |
| 3 | 103.3 | >289.1 |
| 4 | 62.0 | 182.9 |
| 5 | 0.0 | 2.7 |
| 6 | 20.9 | 53.0 |

Example 19. Inhibition of Serotonin Transporter

The ability of disclosed compounds to inhibit uptake of monoamines by the serotonin transporter (SERT) was measured using a fluorescent substrate uptake assay in transfected cells. Data are presented in Table 14. Compounds were of variable potency for inhibition of SERT. Fluorinated Compound 4 was the most potent of the compounds tested at SERT and much more potent than its non-fluorinated counterpart Compound 2 at this target.

Test Compounds. Compound 4 was prepared as described above. All other compounds were commercially obtained.

SERT Uptake Inhibition. The ability of test compounds to block monoamine uptake by SERT was determined using the Neurotransmitter Transporter Uptake Assay Kit manufactured by Molecular Devices (Cat #R8173). Briefly, stably transfected HEK293 cells expressing SERT were grown and plated into 384-well plates at a concentration of 20,000 cells per well. Plates were then incubated for 16-20 h at 37° C. and 5% $CO_2$. The medium was then aspirated and replaced with 25 μL of assay buffer (20 mM HEPES in HBSS, containing 0.1% BSA) containing the test compounds at the appropriate concentrations. Plates were then centrifuged at 300 rpm for 15 s and then incubated at 37° C. for 30 minutes. At this time, 25 μL of the proprietary fluorescent dye solution was added, the plates were incubated at 37° C. for 60 minutes, and then fluorescence was quantified on a plate reader (excitation wavelength=440 nm, emission wavelength=520 nm). The proprietary dye solution contains a mixture of 1) a fluorescent dye (dye 1) that mimics the endogenous substrate of SERT and is thereby actively transported to the intracellular compartment in the absence of an inhibitor and 2) a masking dye that inhibits the fluorescence of dye 1 in the extracellular compartment. Therefore, the overall fluorescence of the system increases as the fluorescent dye is transported into the cells. In the presence of an inhibitor of SERT, uptake of the dye is reduced, and therefore, the fluorescence is also decreased, allowing this inhibition to be quantified.

TABLE 14

Inhibition of SERT by compounds.

| Compound | SERT $IC_{50}$ (nM) | SERT % Inhibition @ Max Dose |
|---|---|---|
| DMT | 2,962 | 67.92 |
| 5-MeO-DMT | 7,020 | 68.07 |
| psilocin | 2,035 | 88.15 |
| 1 | 750.4 | 75.35 |
| 2 | 9,131 | 62.06 |

TABLE 14-continued

Inhibition of SERT by compounds.

| Compound | SERT IC$_{50}$ (nM) | SERT % Inhibition @ Max Dose |
|---|---|---|
| 4 | 418.9 | 77.45 |
| 6 | 3,268 | 84.02 |

Example 20. Serotonin Release Activity in Synaptosomes

Disclosed compounds were assessed for their ability to release serotonin (5-HT) from rat synaptic vesicles (Table 15). Fluorinated Compound 4 was a much more potent serotonin releaser than its non-fluorinated counterpart Compound 2.

Test Compounds. Compound 4 was prepared as described above. All other compounds were commercially obtained.

Synaptosome 5-HT Release Assay. Synaptosome release assays were conducted according to modifications of previously described procedures (Partilla et al. (2016). Interrogating the Activity of Ligands at Monoamine Transporters in Rat Brain Synaptosomes. In Neurotransmitter Transporters (pp. 41-52). Springer). Briefly, synaptosomes were prepared from rat brains. Male Sprague-Dawley rats were rendered unconscious with $CO_2$ and their brains were immediately removed. The cerebella were discarded and the whole brains (minus striatum) were placed in ice-cold 0.32 M sucrose (10 mL per brain) and gently homogenized by hand. The homogenate of each brain was centrifuged at 1,000×g at 4° C. for 10 mins and the resulting supernatant was diluted with ice-cold 0.32 M sucrose to a total volume of 10 mL to provide the synaptosome solution. Synaptosomes were then preloaded with 5 nM [$^3$H]5-HT in the presence of selective uptake inhibitors of DAT (50 nM GBR12935), NET (100 nM nomifensine), and VMAT2 (1 µM reserpine) in Krebs phosphate buffer (KPB). The incubations were allowed to reach equilibrium for 2 h at 25° C. For the release reactions, 425 µL of preloaded synaptosomes were added to test tubes containing 75 µL of test drugs diluted in KPB containing 1 mg/mL BSA. After 10 mins, the release reaction was stopped using a cell harvester by rapid vacuum filtration over GF/B filter paper presoaked in wash buffer (10 mM Tris-HCl, pH 7.4, 150 mM NaCl) and the filters were washed with additional wash buffer. Filters were dried for 1 h at 60° C. and retained radioactivity was quantified using a MicroBeta 2 liquid scintillation counter. The amount of retained radioactivity was inversely proportional to the extent of release.

TABLE 15

Effect of compounds on 5-HT release from rat synaptosomes.

| Compound | 5-HT Release EC$_{50}$ (nM) | % Release @ Max Dose (10 µM) |
|---|---|---|
| DMT | 80.76 | 80.77 |
| 2 | 182.7 | 71 |
| 4 | 8.426 | 71.36 |

Example 21. Synthesis of Additional Compounds

Additional disclosed compounds may be prepared by standard methods known to those skilled in the art of organic synthesis, for example, those presented in Examples 1-3 and described elsewhere herein.

The invention claimed is:
1. A compound represented by:

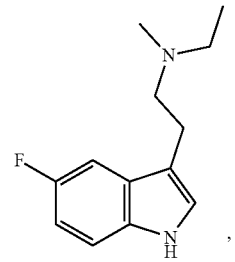

or a pharmaceutically acceptable salt thereof.
2. A pharmaceutical composition comprising a compound of claim 1 and a pharmaceutically acceptable excipient.

* * * * *

UNITED STATES PATENT AND TRADEMARK OFFICE
CERTIFICATE OF CORRECTION

PATENT NO. : 11,440,879 B2
APPLICATION NO. : 17/510080
DATED : September 13, 2022
INVENTOR(S) : Andrew Carry Kruegel Page 1 of 1

It is certified that error appears in the above-identified patent and that said Letters Patent is hereby corrected as shown below:

In the Specification

Column 52, Lines 26-36 should read:

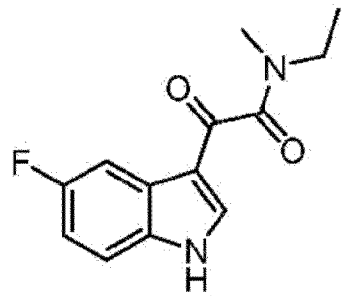

Signed and Sealed this
Twelfth Day of September, 2023

Katherine Kelly Vidal
Director of the United States Patent and Trademark Office